(12) United States Patent  
Suzuki et al.

(10) Patent No.: US 9,537,109 B2  
(45) Date of Patent: *Jan. 3, 2017

(54) LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hiroki Suzuki, Kanagawa (JP); Satoshi Seo, Kanagawa (JP); Sachiko Kawakami, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,799

(22) Filed: Feb. 3, 2016

(65) Prior Publication Data

US 2016/0233437 A1 Aug. 11, 2016

Related U.S. Application Data

(63) Continuation of application No. 14/101,623, filed on Dec. 10, 2013, now Pat. No. 9,257,655.

(30) Foreign Application Priority Data

Dec. 11, 2012 (JP) .................................. 2012-270021

(51) Int. Cl.
*H01L 51/00* (2006.01)
*C07D 209/86* (2006.01)
(Continued)

(52) U.S. Cl.
CPC ......... *H01L 51/0072* (2013.01); *C07D 209/86* (2013.01); *C09K 11/025* (2013.01);
(Continued)

(58) Field of Classification Search
CPC ........................ H01L 51/0072; H01L 51/0052
See application file for complete search history.

(56) References Cited

U.S. PATENT DOCUMENTS 8,084,146 B2 12/2011 Murase et al.
8,183,793 B2 5/2012 Egawa et al.
(Continued)

FOREIGN PATENT DOCUMENTS

CN 101506163 A 8/2009
CN 101970448 A 2/2011
(Continued)

OTHER PUBLICATIONS

Goldsmith, C.R. et al., "C—H Bond Activation by a Ferric Methoxide Complex: Modeling the Rate-Determining Step in the Mechanism of Lipoxygenase," Journal of the American Chemical Society, 2002, vol. 124, No. 1, pp. 83-96.
(Continued)

*Primary Examiner* — Lex Malsawma
(74) *Attorney, Agent, or Firm* — Husch Blackwell LLP

(57) ABSTRACT

Provided is a light-emitting element which has high emission efficiency and a long lifetime and is driven at low voltage. The light-emitting element includes an EL layer between a pair of electrodes. The EL layer includes a compound which gives a first peak at a m/z of around 266.10 in a mass spectrum.

14 Claims, 31 Drawing Sheets

(51) Int. Cl.
*C09K 11/02* (2006.01)
*C09K 11/06* (2006.01)
*H01L 51/50* (2006.01)

(52) U.S. Cl.
CPC ............ *C09K 11/06* (2013.01); *H01L 51/006* (2013.01); *H01L 51/0052* (2013.01); *H01L 51/0058* (2013.01); *C09K 2211/1029* (2013.01); *H01L 51/5012* (2013.01); *H01L 51/5028* (2013.01)

(56) References Cited

U.S. PATENT DOCUMENTS

| | | | |
|---|---|---|---|
| 8,471,248 | B2 | 6/2013 | Schmidhalter et al. |
| 8,986,857 | B2 | 3/2015 | Suzuki et al. |
| 9,240,558 | B2 | 1/2016 | Suzuki et al. |
| 9,257,655 | B2 * | 2/2016 | Suzuki ................ H01L 51/0072 |
| 2002/0093005 | A1 | 7/2002 | Sohn et al. |
| 2003/0186077 | A1 | 10/2003 | Chen |
| 2007/0247063 | A1 | 10/2007 | Murase et al. |
| 2008/0107918 | A1 | 5/2008 | Egawa et al. |
| 2008/0122344 | A1 | 5/2008 | Shin et al. |
| 2011/0068683 | A1 | 3/2011 | Kawamura et al. |
| 2012/0138907 | A1 | 6/2012 | Murase et al. |
| 2013/0020561 | A1 * | 1/2013 | Suzuki ................ C07D 209/60 257/40 |
| 2014/0034925 | A1 | 2/2014 | Osaka et al. |
| 2014/0070204 | A1 | 3/2014 | Nagao et al. |

FOREIGN PATENT DOCUMENTS

| | | |
|---|---|---|
| CN | 103052624 A | 4/2013 |
| EP | 1 748 045 A1 | 1/2007 |
| EP | 2 450 356 A1 | 5/2012 |
| TW | 201105774 | 2/2011 |
| WO | WO 03/059014 A1 | 7/2003 |
| WO | WO 2005/113531 A1 | 12/2005 |
| WO | WO 2008/026614 A1 | 3/2008 |
| WO | WO 2009/100991 A1 | 8/2009 |
| WO | WO 2010/114264 A2 | 10/2010 |
| WO | WO 2011/010842 A2 | 1/2011 |
| WO | WO 2013/015144 A1 | 1/2013 |

OTHER PUBLICATIONS

Onishi, T. et al., "A Method of Measuring an Energy Level," High Molecular EL Materials—Development of Light-Emitting High Molecular Compounds, Dec. 25, 2004, pp. 64-67, Kyoritsu Shuppan.

Zander, M. et al., "Note on the Dehydration of Di-β-naphthylamine and Di-β-anthrylamine with Copper Powder," Chemische Berichte, 1964, vol. 97, No. 1, pp. 304-306.

International Search Report re Application No. PCT/JP2012/068049, dated Sep. 25, 2012.

Written Opinion re Application No. PCT/JP2012/068049, dated Sep. 25, 2012.

Chinese Office Action re Application No. CN 201310675766.5, dated Oct. 9, 2016.

* cited by examiner

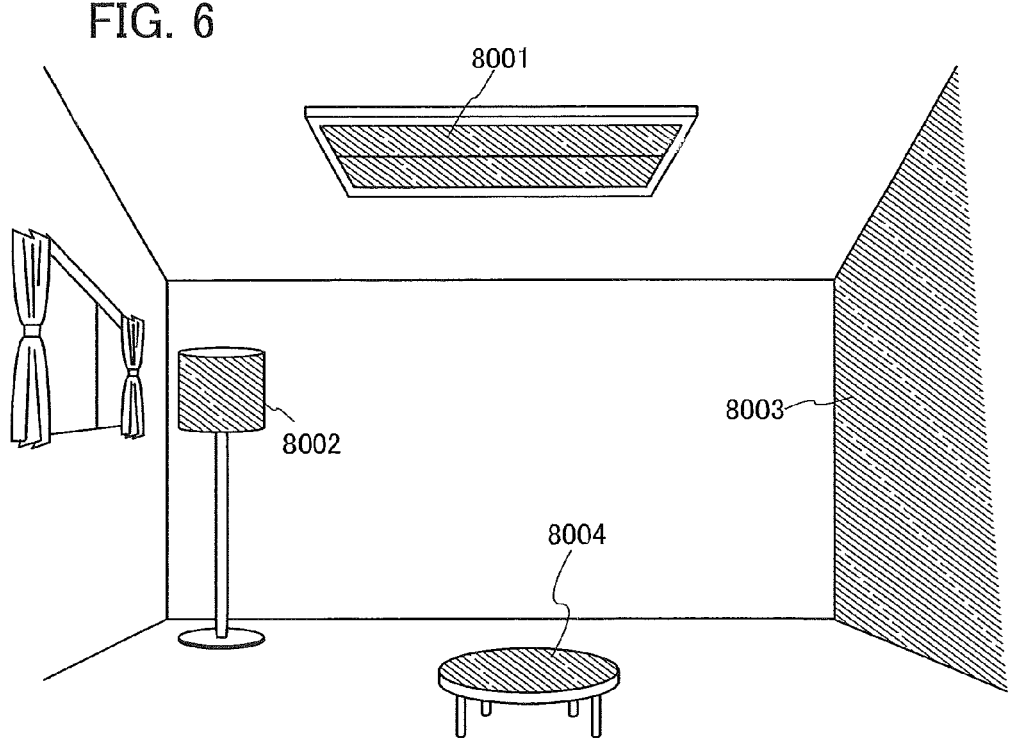

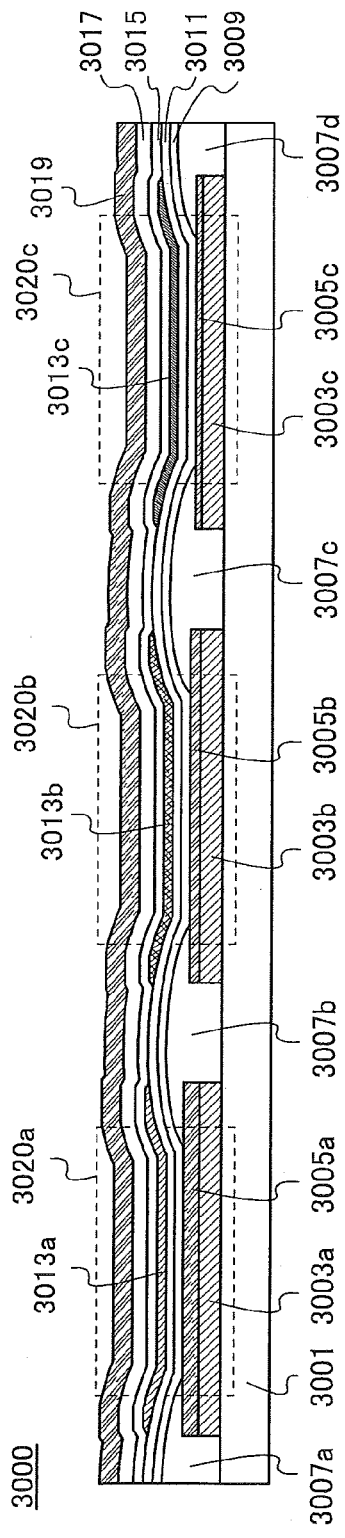
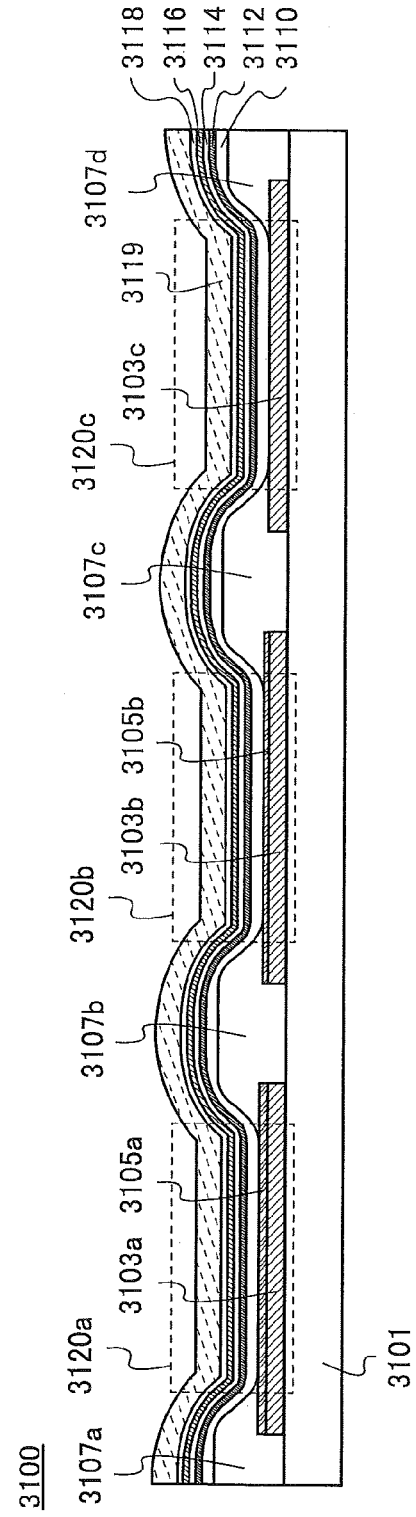
FIG. 35A
FIG. 35B

LIGHT-EMITTING ELEMENT, LIGHT-EMITTING DEVICE, ELECTRONIC DEVICE, AND LIGHTING DEVICE

This application is a continuation of copending U.S. application Ser. No. 14/101,623, filed on Dec. 10, 2013 which is incorporated herein by reference.

BACKGROUND OF THE INVENTION

1. Field of the Invention

The present invention relates to, for example, a semiconductor device, a display device, a light-emitting device, a driving method thereof, and a manufacturing method thereof. In particular, the present invention relates to a light-emitting element, a light-emitting device, an electronic device, and a lighting device each using a dibenzo[c,g] carbazole compound.

2. Description of the Related Art

A light-emitting element (organic EL element) in which an organic compound is used as a light-emitting substance has been progressed because it has advantages that such a light-emitting element can be formed to be thin and lightweight, has very high response speed for input signals, and has low power consumption.

In a light-emitting element, when a voltage is applied between electrodes with a light-emitting layer interposed therebetween, electrons and holes injected from the electrodes recombine to form an excited state, and when the excited state returns to a ground state, light emission is obtained. Since the wavelength of light emitted from a light-emitting substance depends on the light-emitting substance, use of different types of organic compounds for light-emitting substances makes it possible to provide light-emitting elements which exhibit various wavelengths, i.e., various colors.

Light emitted from a light-emitting substance is peculiar to the substance, as described above. However, important performances as a light-emitting element, such as lifetime and power consumption, are not only dependent on the light-emitting substance but also greatly dependent on layers other than a light-emitting layer including the light-emitting substance, an element structure, properties of a light-emitting substance (a guest material) and a host material, compatibility between them, and the like. Thus, many kinds of light-emitting element materials are necessary. For the above-described reasons, light-emitting element materials with a variety of molecular structures have been proposed (e.g., Patent Documents 1 to 4).

REFERENCES

[Patent Document 1] United States Published Patent Application No. 2008/0122344
[Patent Document 2] PCT International Publication No. 2010/114264
[Patent Document 3] PCT International Publication No. 2011/010842

SUMMARY OF THE INVENTION

Although many light-emitting element materials have been proposed so far as described above, there is room for improvement in characteristics of the light-emitting elements, such as emission efficiency, driving voltage, and lifetime. In view of the above background, one embodiment of the present invention provides a light-emitting element having high emission efficiency. Another embodiment of the present invention provides a light-emitting element that can be driven at low voltage. Another embodiment of the present invention provides a light-emitting element having a long lifetime. Another embodiment of the present invention provides a light-emitting element having high heat resistance. Another embodiment of the present invention provides a light-emitting element for which film formation can be performed at a fairly low temperature. Another embodiment of the present invention provides a light-emitting element material having an excellent carrier-transport property. Another embodiment of the present invention provides a light-emitting element material having a high electrochemical stability. Another embodiment of the present invention provides a novel light-emitting element.

Note that the descriptions of these objects do not disturb the existence of other objects. Note that in one embodiment of the present invention, there is no need to achieve all of the objects. Note that other objects will be apparent from the description of the specification, the drawings, the claims, and the like and other objects can be derived from the description of the specification, the drawings, the claims, and the like.

One embodiment of the present invention is a light-emitting element including an EL layer containing a dibenzo[c,g]carbazole compound between a pair of electrodes, in which the dibenzo[c,g]carbazole compound includes at least a dibenzo[c,g]carbazole skeleton and an anthracene skeleton. Note that the dibenzo[c,g]carbazole compound is preferably bonded to an aryl group containing an anthracene skeleton at the 7-position of the dibenzo[c,g]carbazole skeleton. Such a structure includes a structure in which the 7-position of the dibenzo[c,g]carbazole skeleton is bonded to the 9-position of the anthracene skeleton through an arylene group such as a phenylene group or a naphthylene group.

One embodiment of the present invention is a light-emitting element including an EL layer between a pair of electrodes. In LC/MS analysis of a substance contained in the EL layer, when a precursor ion is accelerated with an energy of greater than or equal to 30 eV and less than or equal to 70 eV to collide with an argon gas, product ions derived by cleavage of a bond between the 7-position of the dibenzo[c,g]carbazole skeleton and the anthracene skeleton or a bond between the 7-position of the dibenzo[c,g]carbazole skeleton and the arylene group are detected.

One embodiment of the present invention is a light-emitting element including an EL layer between a pair of electrodes, and the EL layer contains a dibenzo[c,g]carbazole compound. The dibenzo[c,g]carbazole compound gives a component which exhibits a mass-to-charge ratio m/z of 596.24 in LC/MS analysis, and when the component is accelerated with an energy of greater than or equal to 30 eV and less than or equal to 70 eV to collide with an argon gas, product ions are detected at least around m/z=266.10 and around m/z=330.14. Here, the expression "around" indicates that the mass-to-charge ratio of the product ions could vary due to the addition or elimination of protons or the presence of isotope. Alternatively, the expression "around" is used when the mass-to-charge ratio is expressed after rounding off, cutting off, or cutting up a certain decimal place.

From the dibenzo[c,g]carbazole compound with any of the above structures (e.g., 7-[4-(10-phenyl-9-anthryl)phenyl]-7H-dibenzo[c,g]carbazole (abbreviated to cgDBCzPA), a product ion which is derived from a 7H-dibenzo[c,g] carbazole skeleton and detected around m/z=266.10 and a product ion which is derived from a 9,10-diphenyl anthracene skeleton and detected around m/z=330.14 are obtained.

One embodiment of the present invention is a light-emitting element including an EL layer between a pair of electrodes, and the EL layer contains a dibenzo[c,g]carbazole compound represented by a general formula (G1) below. In LC/MS analysis of the dibenzo[c,g]carbazole compound in which a precursor ion is accelerated with an energy of greater than or equal to 30 eV and less than or equal to 70 eV to collide with an argon gas, at least one of a product ion derived from Ar and a product ion derived from the dibenzo[c,g]carbazole compound is detected. The product ions are obtained by a cleavage of a bond between Ar and a nitrogen atom of the dibenzo[c,g]carbazole skeleton.

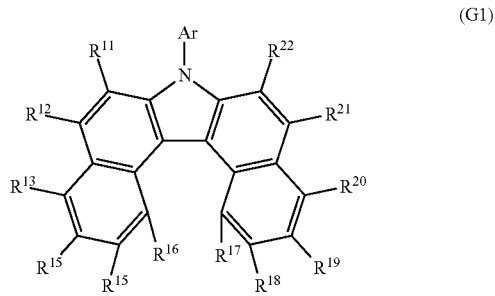

(G1)

In the above general formula (G1), Ar represents a substituted or unsubstituted aryl group having 14 to 30 carbon atoms and including at least an anthracene skeleton. In the case where the anthracene skeleton has a substituent, the substituent can be an alkyl group having 1 to 4 carbon atoms. Other than such a substituent, an aryl group having 6 to 10 carbon atoms can also be selected as the substituent at the 10-position of the anthracene skeleton. Throughout the specification, the "alkyl group having 1 to 4 carbon atoms" means a methyl group, an ethyl group, a propyl group, an isopropyl group, an n-butyl group, an s-butyl group, an isobutyl group, and a tert-butyl group. Throughout the specification, as the "aryl group having 6 to 10 carbon atoms", a phenyl group and a naphthyl group are exemplified, and as the "aryl group having 6 to 12 carbon atoms", a phenyl group, a naphthyl group, a biphenyl group, and the like are exemplified. Note that in this specification, when the number of carbon atoms is defined, this number means the total number of carbon atoms including those of the specified structure and its substituent. Therefore, an anthracene skeleton having 15 carbon atoms is exemplified by a methyl-substituted anthryl group.

Further, $R^{11}$ to $R^{22}$ each independently represent any of hydrogen, an alkyl group having 1 to 4 carbon atoms, and an aryl group having 6 to 12 carbon atoms.

In the dibenzo[c,g]carbazole compound described above, the aryl group (Ar) is bonded to the 7-position of the dibenzo[c,g]carbazole skeleton and the aryl group has 14 to 30 carbon atoms and includes at least an anthracene skeleton. Since the number of carbon atoms of the aryl group is featured to be 14 to 30, the dibenzo[c,g]carbazole compound has a relatively low molecular weight and accordingly has a structure suitable for vacuum evaporation (capable of being vacuum-evaporated at relatively low temperature). In general, a compound with a lower molecular weight tends to give a film with diminished heat resistance. However, even with a low molecular weight, the dibenzo[c,g]carbazole compound has an advantage that sufficient heat resistance of its film can be ensured because of the rigidity of the dibenzo[c,g]carbazole skeleton.

Another embodiment of the present invention is a light-emitting element including, between a pair of electrodes, an EL layer which includes a dibenzo[c,g]carbazole compound represented by a following general formula (G5). An LC/MS analysis of the dibenzo[c,g]carbazole compound in which a precursor ion is accelerated with an energy of greater than or equal to 30 eV and less than or equal to 70 eV to collide with an argon gas allows the detection of at least one of a product ion which originates from the α-containing anthracene skeleton and a product ion which originates from the dibenzo[c,g]carbazole skeleton, where the product ions are derived from the bond cleavage between Ar and nitrogen atom (note that the α-containing anthracene skeleton includes an anthrylphenyl group).

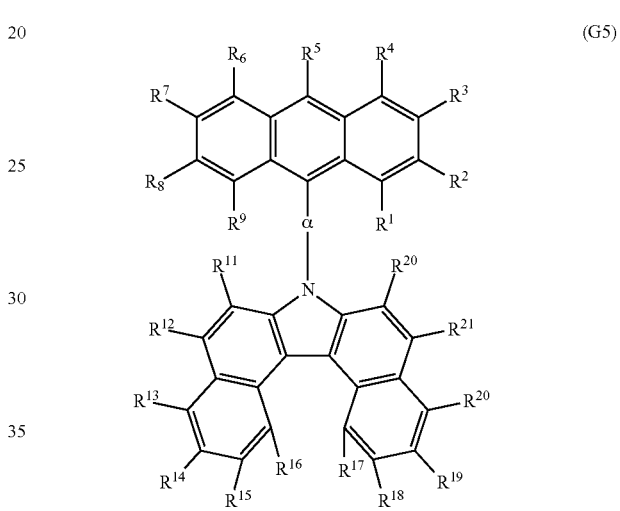

(G5)

In the general formula (G5), $R^5$ represents any of hydrogen, an alkyl group having 1 to 4 carbon atoms, and an aryl group having 6 to 10 carbon atoms. Further, $R^1$, $R^2$, $R^3$, $R^4$, $R^6$, $R^7$, $R^8$, and $R^9$ each independently represent any of hydrogen or an alkyl group having 1 to 4 carbon atoms. Further, $R^{11}$ to $R^{22}$ each independently represent any of hydrogen, an alkyl group having 1 to 4 carbon atoms, and an aryl group having 6 to 12 carbon atoms, and a represents a substituted or unsubstituted arylene group. Note that the total number of carbon atoms of $R^1$ to $R^9$ and α is greater than or equal to 6 and less than or equal to 16.

In the case where the dibenzo[c,g]carbazole compound has a structure in which an anthracene skeleton is bonded to a dibenzo[c,g]carbazole skeleton through an arylene group as represented by the general formula (G5), the compound especially has the advantage in lifetime and an excellent carrier-transport property; thus, a light-emitting element using the compound can be driven at extremely low voltage.

Additionally, in the case where the dibenzo[c,g]carbazole compound has a structure in which the 7-position of a dibenzo[c,g]carbazole skeleton is bonded to the 9-position of an anthracene skeleton through an arylene group such as a phenylene group and a naphthylene group as represented by the general formula (G5), the compound especially has a wide band gap and thus is useful.

That is, in the case where the dibenzo[c,g]carbazole compound has a structure in which a substituted or unsubstituted anthrylphenyl group having 20 to 30 carbon atoms is bonded to the 7-position of a dibenzo[c,g]carbazole skeleton, a light-emitting element using the compound can have favorable stability of element characteristics and reliability and can be driven at low voltage. This is because the dibenzo[c,g]carbazole compound has a wide band gap due to the effect of the skeleton of the 9-anthryl group, in addition to the facility in evaporation and a high carrier-transport property described above. Hence, a structure of a light-emitting element is also preferable in which the dibenzo[c,g]carbazole compound is used as a host material of a light-emitting layer in an EL layer and a light-emitting material is combined with a guest material.

Other embodiments of the present invention are not only a light-emitting device including the light-emitting element but also an electronic device and a lighting device each including the light-emitting device. Accordingly, a light-emitting device in this specification refers to an image display device or a light source (including a lighting device). In addition, the light-emitting device includes, in its category, all of a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

In one embodiment of the present invention, a light-emitting element having high emission efficiency, low driving voltage, and a long lifetime can be provided. Furthermore, a light-emitting device, an electronic device, or a lighting device in which power consumption is reduced with the use of the light-emitting element of one embodiment of the present invention can be provided.

BRIEF DESCRIPTION OF THE DRAWINGS

FIG. 6 illustrates lighting devices.
FIGS. 35A and 35B each illustrate a light-emitting device of one embodiment of the present invention.

DETAILED DESCRIPTION OF THE INVENTION

Figure 1:
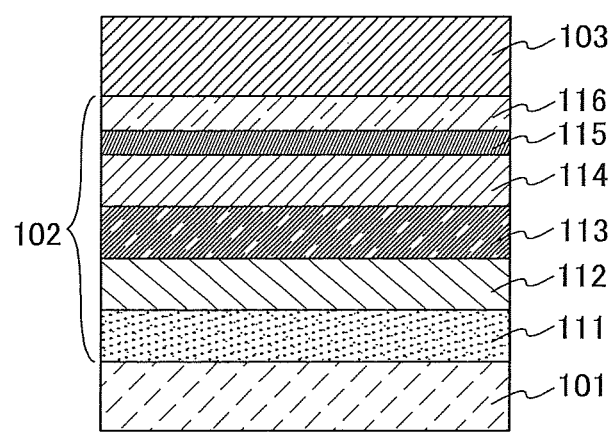
FIG. 1 illustrates a structure of a light-emitting element.

Hereinafter, embodiments of the present invention are described. Note that the present invention can be implemented in various modes, and it is easily understood by those skilled in the art that modes and details disclosed herein can be modified in various ways without departing from the spirit and the scope of the present invention. Therefore, the present invention is not construed as being limited to description of the embodiments.

(Embodiment 1)

In this embodiment, a light-emitting element which is one embodiment of the present invention is described.

The light-emitting element of this embodiment includes an EL layer containing a dibenzo[c,g]carbazole compound between a pair of electrodes, and the dibenzo[c,g]carbazole compound includes at least a dibenzo[c,g]carbazole skeleton and an aryl group containing an anthracene skeleton. Note that the 7-position of the dibenzo[c,g]carbazole skeleton may be bonded to the 9-position of the anthracene skeleton through an arylene group. Since the dibenzo[c,g]carbazole compound has an excellent carrier-transport property, the light-emitting element can be driven at low voltage. Furthermore, since the dibenzo[c,g]carbazole compound has high electrochemical stability, the light-emitting element can have a long lifetime. Furthermore, since the dibenzo[c,g]carbazole compound has a wide band gap, the light-emitting element can have high emission efficiency. As described above, the light-emitting element of this embodiment is a high-performance light-emitting element excellent in various characteristics.

Note that when the number of carbon atoms of the aryl group is 14 to 30, the dibenzo[c,g]carbazole compound has a relatively low molecular weight and accordingly has a structure suitable for vacuum evaporation (capable of being vacuum-evaporated at relatively low temperature). In general, a compound with a lower molecular weight tends to give a film with diminished heat resistance. However, even with a low molecular weight, the dibenzo[c,g]carbazole compound has an advantage that sufficient heat resistance of its film can be ensured because of the rigidity of the dibenzo[c,g]carbazole skeleton. Note that the anthracene skeleton and the dibenzo[c,g]carbazole skeleton described above may be bonded with an arylene group, such as a phenylene group or a naphthylene group, interposed therebetween.

Further, a light-emitting element using a dibenzo[c,g]carbazole compound in which an anthracene skeleton is bonded to the 7-position of a dibenzo[c,g]carbazole skeleton through a phenylene group especially has the advantage in lifetime. The dibenzo[c,g]carbazole compound has a particularly excellent carrier-transport property and a light-emitting element using this compound can be driven at very low voltage.

The above light-emitting element can be rephrased as a light-emitting element containing a dibenzo[c,g]carbazole compound in which an anthrylphenyl group is bonded to a dibenzo[c,g]carbazole skeleton. For example, a dibenzo[c,g]carbazole compound is exemplified in which a 9-anthrylphenyl group is bonded to the 7-position of the dibenzo[c,g]carbazole skeleton. Note that the dibenzo[c,g]carbazole compound can be easily synthesized with high purity, so that deterioration of the light-emitting element due to impurities can be suppressed. Note that the number of carbon atoms of the anthrylphenyl group (including the 9-anthrylphenyl group) is preferably 20 to 30 in terms of the stability and reliability of element characteristics. In this case, the dibenzo[c,g]carbazole compound can be vacuum-evaporated at lower temperature and accordingly is less likely to deteriorate due to thermal decomposition or the like at evaporation. In addition, the light-emitting element is excellent in not only reliability but also driving voltage. This is because of high electrochemical stability and an excellent carrier-transport property of the dibenzo[c,g]carbazole compound.

Note that a dibenzo[c,g]carbazole compound in which an anthracene skeleton is bonded to the 7-position of a dibenzo[c,g]carbazole skeleton through an arylene group or a dibenzo[c,g]carbazole compound in which an anthrylphenyl group is bonded to a dibenzo[c,g]carbazole skeleton is particularly suitable as a light-emitting element which exhibits light emission with large energy such as blue fluorescence.

The aforementioned dibenzo[c,g]carbazole compound has a wide band gap which is a feature due to the steric hindrance between the 9-anthryl group and the arylene group, in addition to the high suitability for evaporation, electrochemical stability, and carrier-transport property described above. Hence, this compound is effective in a structure of a light-emitting element in which the dibenzo[c,g]carbazole compound is used as a host material of a light-emitting layer and combined with a light-emitting material as a guest material.

An EL layer included in the above-described light-emitting element of one embodiment of the present invention contains a dibenzo[c,g]carbazole compound. In LC/MS analysis of the dibenzo[c,g]carbazole compound, when a precursor ion is accelerated with an energy of greater than or equal to 30 eV and less than or equal to 70 eV to collide with an argon gas, product ions derived by cleavage of a bond between the 7-position of a dibenzo[c,g]carbazole skeleton and the arylene group is detected.

Note that product ions which are detected by LC/MS analysis are featured by the structure of the dibenzo[c,g]carbazole compound contained in the EL layer. In the case where the dibenzo[c,g]carbazole compound has a structure in which the 7-position of the dibenzo[c,g]carbazole skeleton is bonded to the 9-position of the anthracene skeleton through a phenylene group as an arylene group, for example, product ions detected around m/z=266.10, which are derived from the dibenzo[c,g]carbazole skeleton, and product ions detected around m/z=330.14, which are derived from a 9,10-diphenyl anthracene skeleton, can be obtained. The results of the LC/MS analysis are described in detail in Example.

(Embodiment 2)

In this embodiment, the dibenzo[c,g]carbazole compound, which is used for the light-emitting element of one embodiment of the present invention, is described.

The dibenzo[c,g]carbazole compound used for the light-emitting element of one embodiment of the present invention is a compound in which an aryl group including at least an anthracene skeleton is bonded to the 7-position of a dibenzo[c,g]carbazole skeleton, and represented by the following general formula (G1).

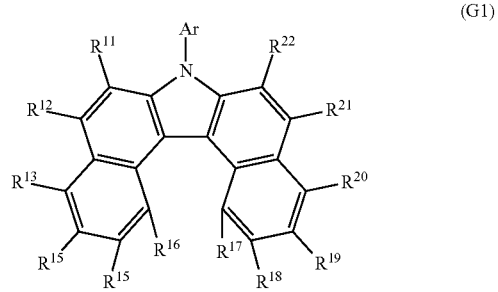

In the above general formula (G1), Ar represents a substituted or unsubstituted aryl group which has 14 to 30 carbon atoms and includes at least an anthracene skeleton. When the anthracene skeleton has a substituent, the substituent can be an alkyl group having 1 to 4 carbon atoms. Other than such a substituent, an aryl group having 6 to 10 carbon atoms can also be selected as the substituent at the 10-position of the anthracene skeleton.

Further, $R^{11}$ to $R^{22}$ each independently represent any of hydrogen, an alkyl group having 1 to 4 carbon atoms, and an aryl group having 6 to 12 carbon atoms.

Further, it is preferred that Ar in the general formula (G1) include at least an anthracene skeleton and an arylene group and the anthracene skeleton be bonded to the dibenzo[c,g]carbazole skeleton through an arylene group, because such a compound can have improved stability and be synthesized with high purity. Moreover, since such a dibenzo[c,g]carbazole compound has an excellent carrier-transport property, the light-emitting element using the compound can be driven at low voltage.

Thus, the dibenzo[c,g]carbazole compound, which is used for the light-emitting element of one embodiment of the present invention, can be expressed by a general formula (G2) below.

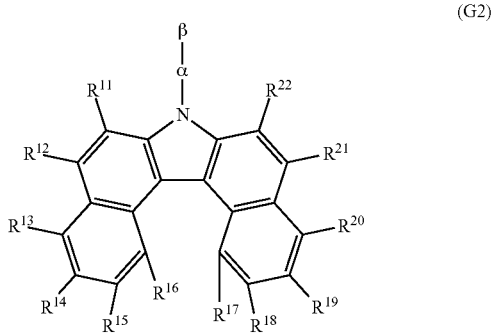

(G2)

In the general formula (G2), $R^{11}$ to $R^{22}$ each independently represent any of hydrogen, an alkyl group having 1 to 4 carbon atoms, and an aryl group having 6 to 12 carbon atoms.

In the general formula (G2), α represents a substituted or unsubstituted arylene group, and β represents a substituted or unsubstituted anthryl group. When α has a substituent, an alkyl group having 1 to 4 carbon atoms can be selected as the substituent. When β has a substituent, the substituent can be an alkyl group having 1 to 4 carbon atoms. Other than such a substituent, an aryl group having 6 to 10 carbon atoms can also be selected as the substituent at the 10-position of the anthracene skeleton.

In the above dibenzo[c,g]carbazole compound, when the 7-position of a dibenzo[c,g]carbazole skeleton is bonded to the 9-position of an anthracene skeleton through an arylene group, the dibenzo[c,g]carbazole compound especially has a wide band gap and is effective. This compound is particularly effective in a structure of a light-emitting element in which the dibenzo[c,g]carbazole compound is used as a host material of a light-emitting layer and a light-emitting material is added as a guest material to the light-emitting layer.

Thus, the dibenzo[c,g]carbazole compound, which is used for the light-emitting element of one embodiment of the present invention, can be expressed by a general formula (G3) below.

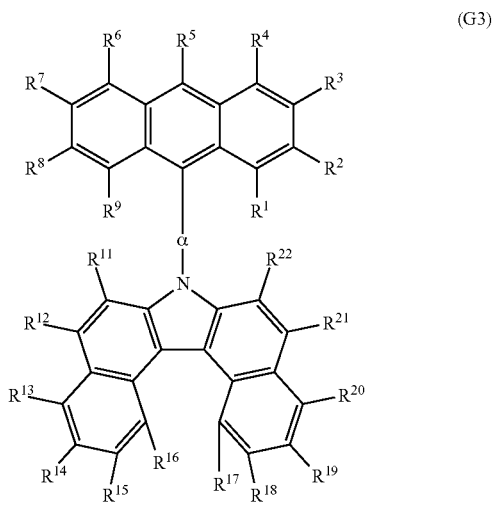

(G3)

In the general formula (G3), $R^5$ represents any of hydrogen, an alkyl group having 1 to 4 carbon atoms, and an aryl group having 6 to 10 carbon atoms. Further, $R^1$, $R^2$, $R^3$, $R^4$, $R^6$, $R^7$, $R^8$, and $R^9$ each independently represent any of hydrogen or an alkyl group having 1 to 4 carbon atoms. Further, $R^{11}$ to $R^{22}$ each independently represent any of hydrogen, an alkyl group having 1 to 4 carbon atoms, and an aryl group having 6 to 12 carbon atoms. In addition, α represents a substituted or unsubstituted arylene group. When α has a substituent, the substituent is an alkyl group having 1 to 4 carbon atoms. Note that α is preferably a substituted or unsubstituted phenyl group.

Note that the dibenzo[c,g]carbazole compound represented by the general formula (G2) can be rephrased as a dibenzo[c,g]carbazole compound in which an anthrylphenyl group is bonded to a dibenzo[c,g]carbazole skeleton, and the dibenzo[c,g]carbazole compound represented by the general formula (G3) can be rephrased as a dibenzo[c,g]carbazole compound in which a (9-anthryl)phenyl group is bonded to a dibenzo[c,g]carbazole skeleton. The number of carbon atoms of the anthrylphenyl group or (9-anthryl)phenyl group bonded to the dibenzo[c,g]carbazole skeleton is preferably 20 to 30 in terms of characteristics such as stability of the element and reliability to be fabricated. This is because the dibenzo[c,g]carbazole compound can be vacuum-evaporated at lower temperature and accordingly is less likely to deteriorate due to thermal decomposition or the like at evaporation. Note that a dibenzo[c,g]carbazole compound having a 9-anthrylphenyl group especially has a wide band gap and therefore can be suitably used as a host material of a light-emitting layer in a light-emitting element.

In the case where the dibenzo[c,g]carbazole compound of one embodiment of the present invention has a structure in which an anthracene skeleton is bonded to the 7-position of a dibenzo[c,g]carbazole skeleton through an arylene group, higher electrochemical stability and carrier-transport property are obtained.

Thus, the dibenzo[c,g]carbazole compound, which is used for the light-emitting element of one embodiment of the present invention, can be expressed by a general formula (G4) or (G5) below.

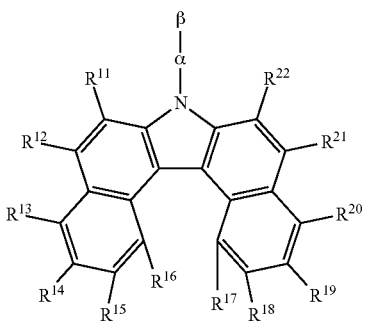

(G4)

In the general formula (G4), $R^{11}$ to $R^{22}$ each independently represent any of hydrogen, an alkyl group having 1 to 4 carbon atoms, and an aryl group having 6 to 12 carbon atoms. In addition, α represents a substituted or unsubstituted arylene group. When α has a substituent, an alkyl group having 1 to 4 carbon atoms can be selected as the substituent. Further, β represents a substituted or unsubstituted anthryl group. When β has a substituent, an example of the substituent is an alkyl group having 1 to 4 carbon atoms. Other than such a substituent, an aryl group having 6 to 10 carbon atoms can also be selected as the substituent at the 10-position of the anthracene skeleton. Note that the total number of carbon atoms of α and β is 20 to 30.

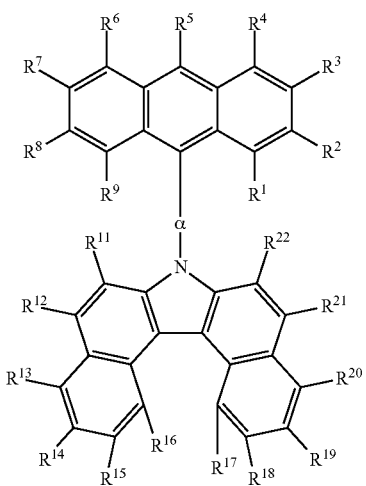

(G5)

In the general formula (G5), $R^5$ represents any of hydrogen, an alkyl group having 1 to 4 carbon atoms, and an aryl group having 6 to 10 carbon atoms. Further, $R^1$, $R^2$, $R^3$, $R^4$, $R^6$, $R^7$, $R^8$, and $R^9$ each independently represent any of hydrogen or an alkyl group having 1 to 4 carbon atoms. Further, $R^{11}$ to $R^{22}$ each independently represent any of hydrogen, an alkyl group having 1 to 4 carbon atoms, and an aryl group having 6 to 12 carbon atoms. In addition, α represents a substituted or unsubstituted arylene group. When α has a substituent, the substituent is an alkyl group having 1 to 4 carbon atoms. Note that the total number of carbon atoms of $R^1$ to $R^9$ and α is greater than or equal to 6 and less than or equal to 16.

The case where each of $R^1$, $R^2$, $R^3$, $R^4$, $R^6$, $R^7$, $R^8$, and $R^9$ is hydrogen has advantages in easiness of synthesis and material cost.

Thus, the dibenzo[c,g]carbazole compound, which is used for the light-emitting element of one embodiment of the present invention, can be expressed by a general formula (G6) below.

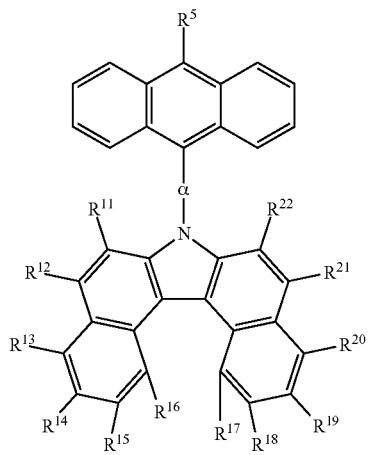

(G6)

In the general formula (G6), α represents a substituted or unsubstituted arylene group. When α has a substituent, the substituent is an alkyl group having 1 to 4 carbon atoms. Further, $R^5$ represents any of hydrogen, an alkyl group having 1 to 4 carbon atoms, and an aryl group having 6 to 10 carbon atoms. Further, $R^{11}$ to $R^{22}$ each independently represent any of hydrogen, an alkyl group having 1 to 4 carbon atoms, and an aryl group having 6 to 12 carbon atoms. Note that the total number of carbon atoms of $R^5$ and α is greater than or equal to 6 and less than or equal to 16.

The case where each of $R^{11}$ to $R^{22}$ is hydrogen has advantages as described above.

Thus, the dibenzo[c,g]carbazole compound, which is used for the light-emitting element of one embodiment of the present invention, can be expressed by a general formula (G7) below.

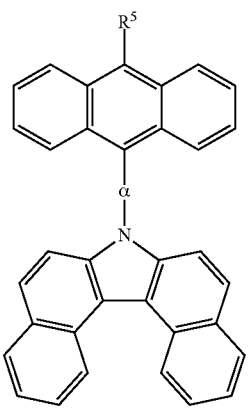

(G7)

In the general formula (G7), α represents a substituted or unsubstituted arylene group. When α has a substituent, the substituent is an alkyl group having 1 to 4 carbon atoms. Further, $R^5$ represents any of hydrogen, an alkyl group having 1 to 4 carbon atoms, and an aryl group having 6 to 10 carbon atoms. Note that the total number of carbon atoms of $R^5$ and α is greater than or equal to 6 and less than or equal to 16.
As the aryl group represented by Ar in the above general formula (G1), for example, groups represented by structural formulae (Ar-1) to (Ar-51) below can be used. Note that a group that can be used as Ar is not limited to these groups.
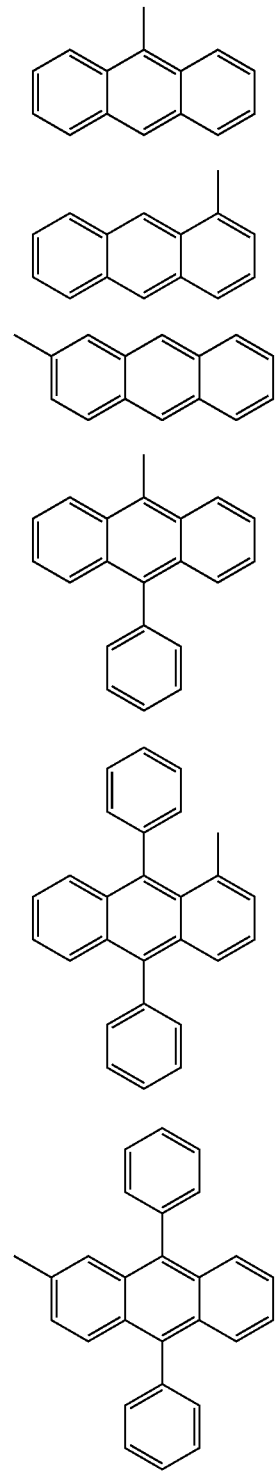
(Ar-1)
(Ar-2)
(Ar-3)
(Ar-4)
(Ar-5)
(Ar-6)
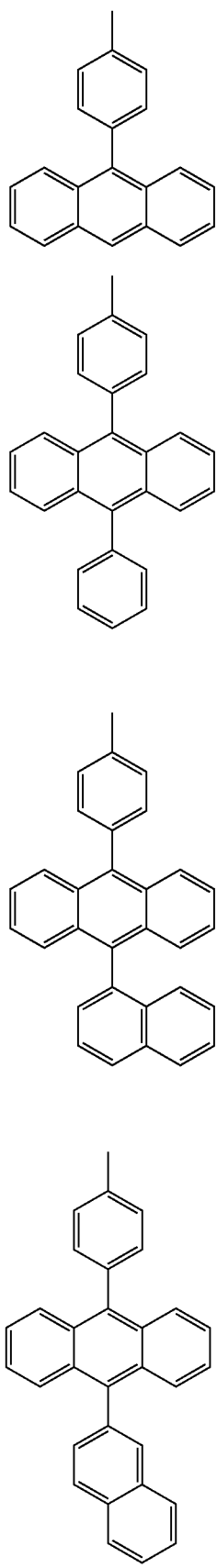
(Ar-7)
(Ar-8)
(Ar-9)
(Ar-10)

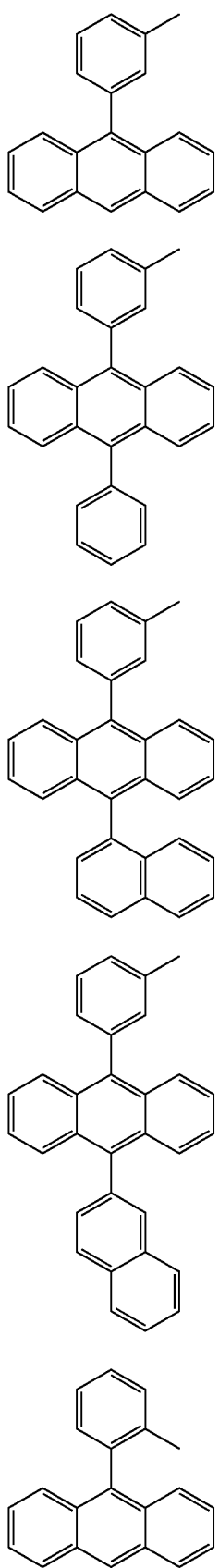
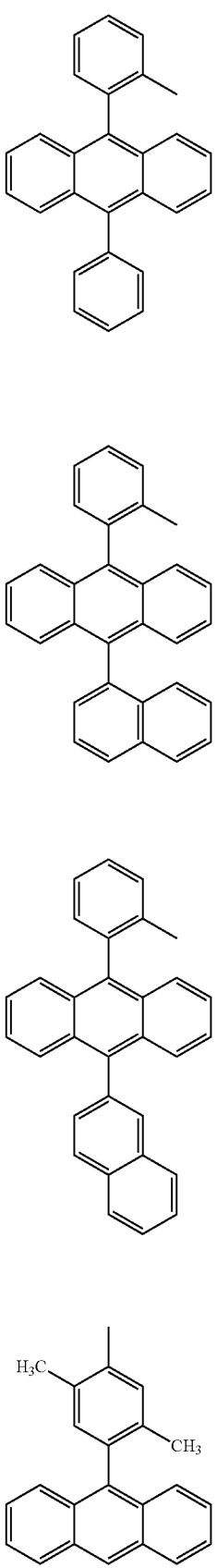

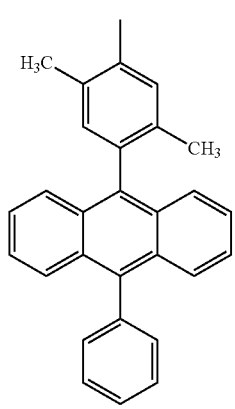
(Ar-20)
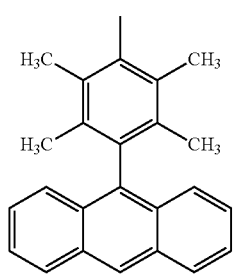
(Ar-21)
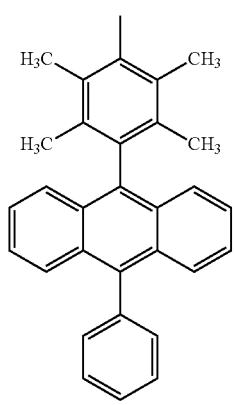
(Ar-22)
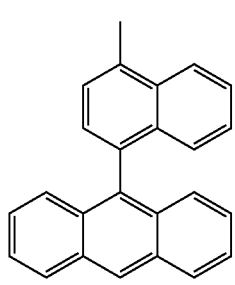
(Ar-23)
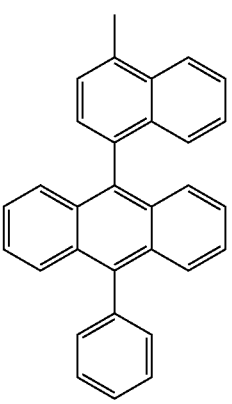
(Ar-24)
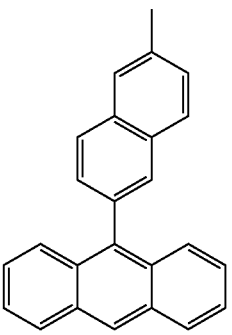
(Ar-25)
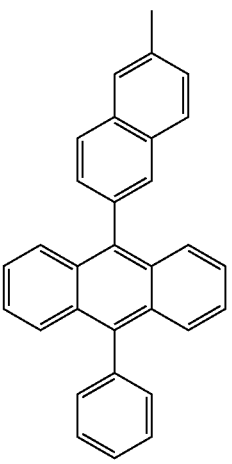
(Ar-26)
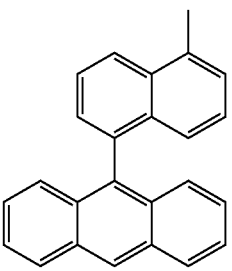
(Ar-27)

(Ar-28) 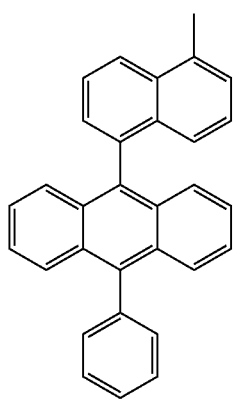
(Ar-29) 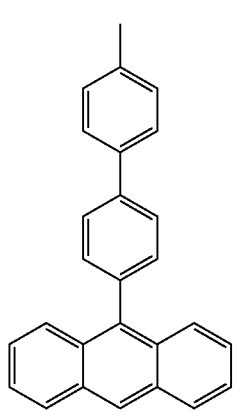
(Ar-30) 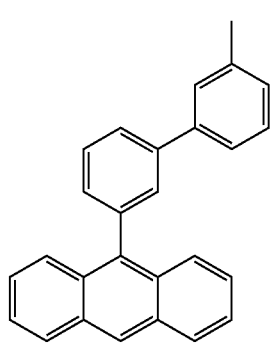
(Ar-31) 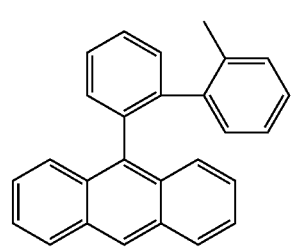
(Ar-32) 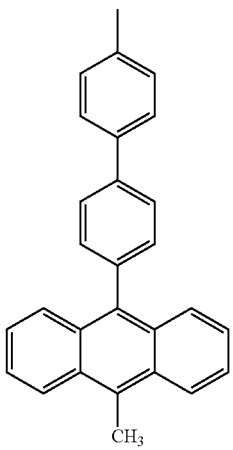
(Ar-33) 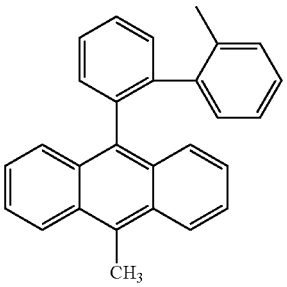
(Ar-34) 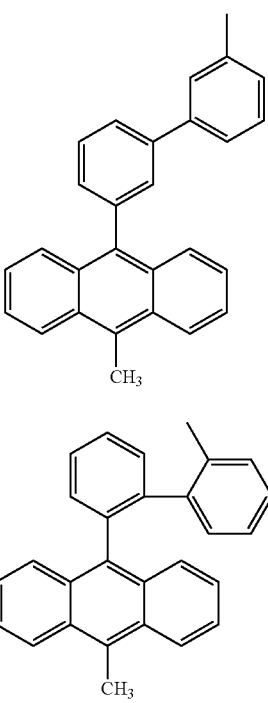
(Ar-35) 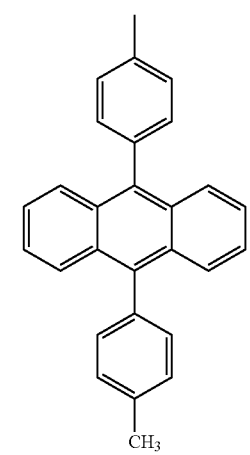

(Ar-36)
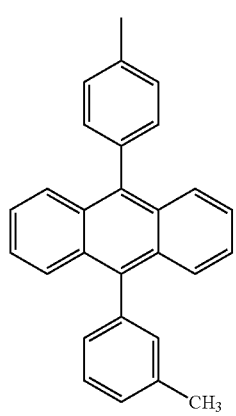
(Ar-37)
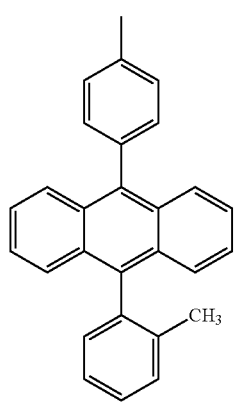
(Ar-38)
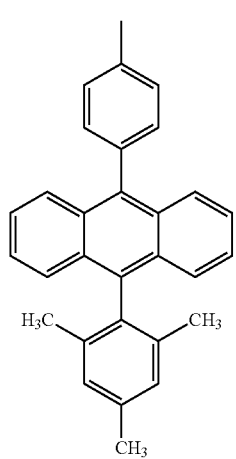
(Ar-39)
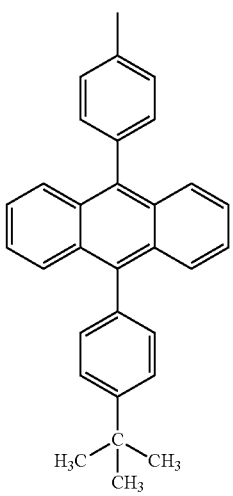
(Ar-40)
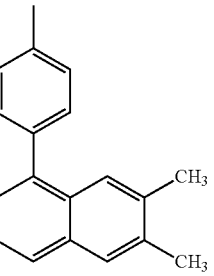
(Ar-41)
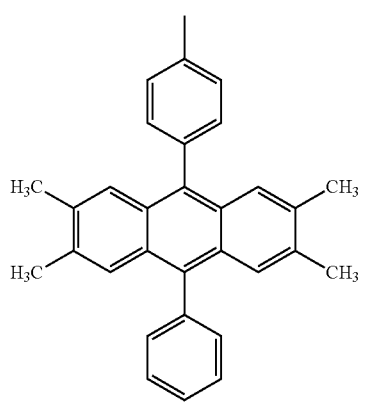
(Ar-42)
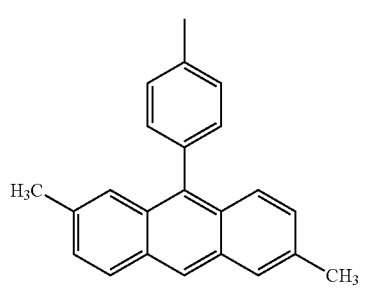

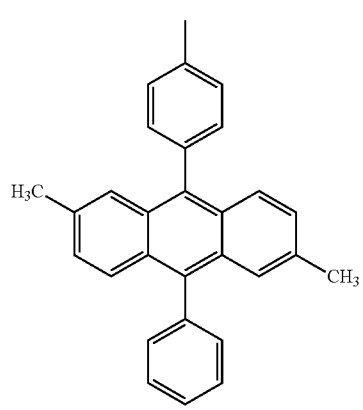
(Ar-43)
(Ar-44)
(Ar-45)
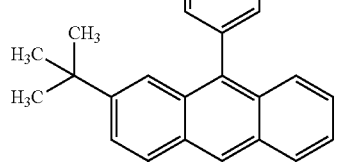
(Ar-46)
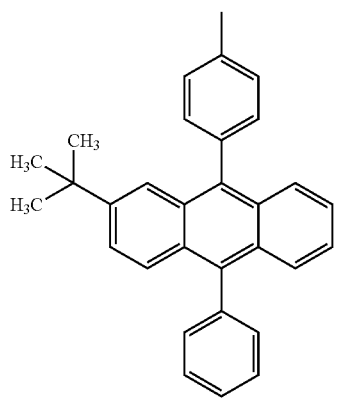
(Ar-47)
(Ar-48)
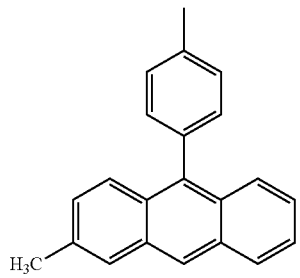
(Ar-49)
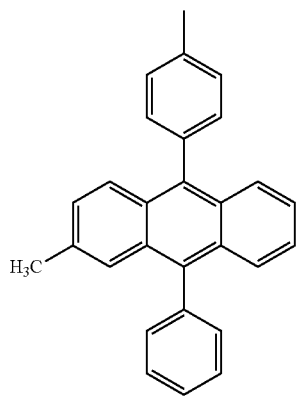
(Ar-50)
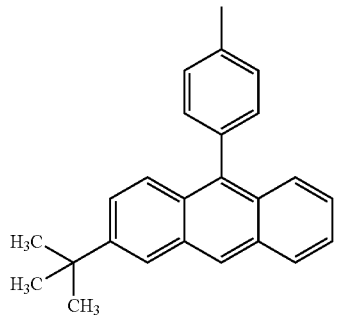

(Ar-51)

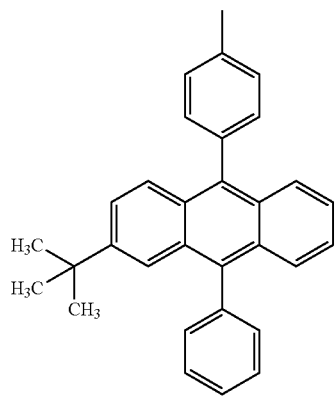

As the aryl group represented by $R^{11}$ to $R^{22}$ in the above general formulae (G1) to (G6), for example, groups represented by structural formulae (Rc-1) to (Re-17) below can be used. Note that a group that can be used as $R^{11}$ to $R^{22}$ is not limited to these groups.

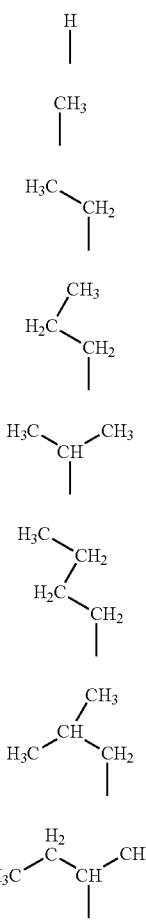

(Rc-1) (Rc-2) (Rc-3) (Rc-4) (Rc-5) (Rc-6) (Rc-7) (Rc-8) (Rc-9)

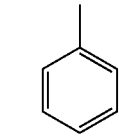

(Rc-10)

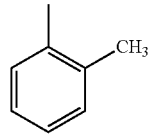

(Rc-11)

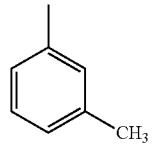

(Rc-12)

(Rc-13)

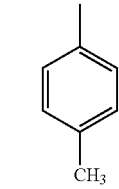

(Rc-14)

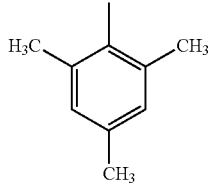

(Rc-15)

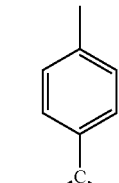

(Rc-16)

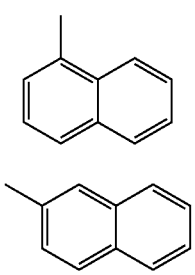

(Rc-17)

As the arylene group represented by α in the above general formulae (G2) to (G7), for example, groups represented by structural formulae (α-1) to (α-11) below can be used. Note that a group that can be used as α is not limited to these.

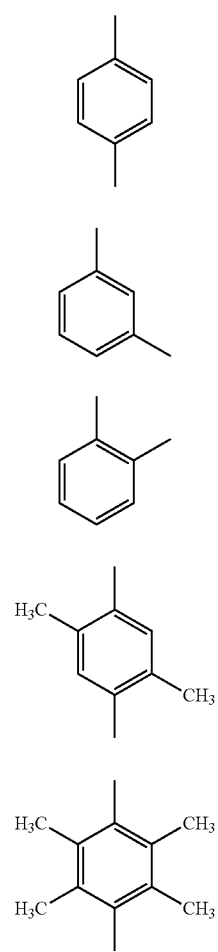
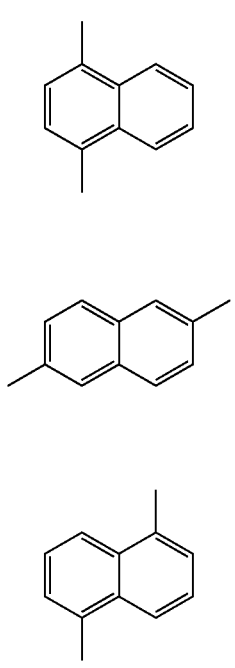
As the aryl group represented by β in the above general formulae (G2) and (G4), for example, groups represented by structural formulae (β-1) to (β-37) below can be used. Note that a group that can be used as β is not limited to these groups.
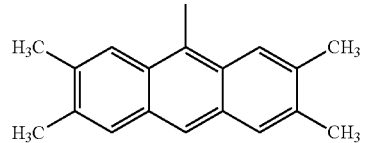

(β-5)
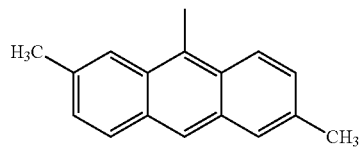
(β-6)
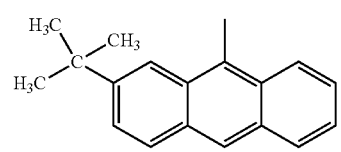
(β-7)
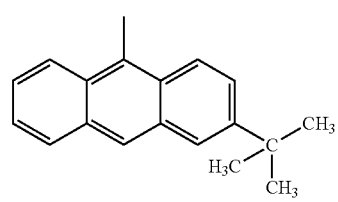
(β-8)
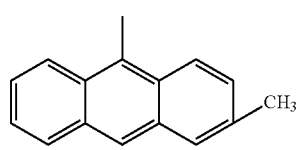
(β-9)
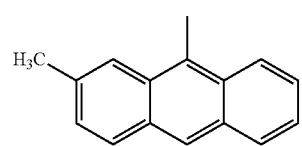
(β-10)
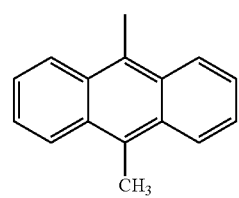
(β-11)
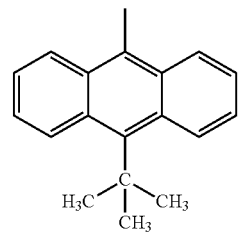
(β-12)
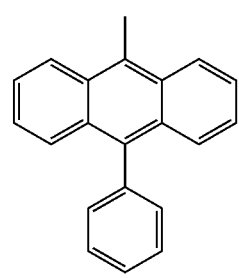
(β-13)
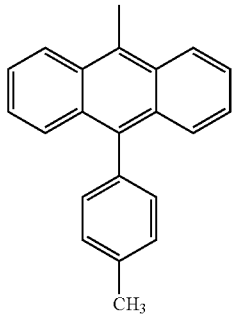
(β-14)
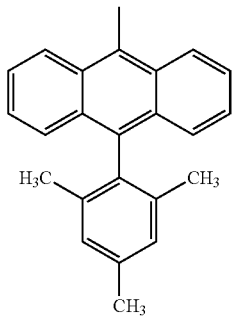
(β-15)
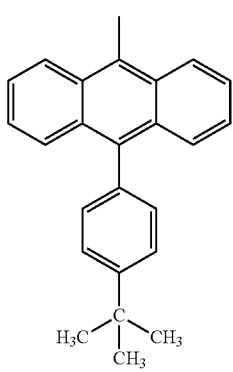
(β-16)
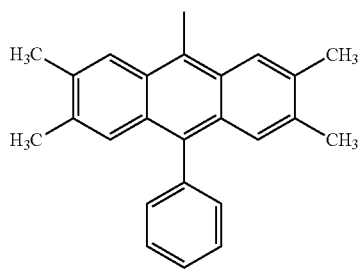
(β-17)
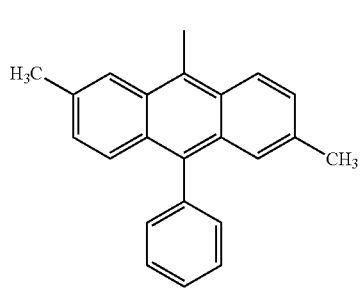

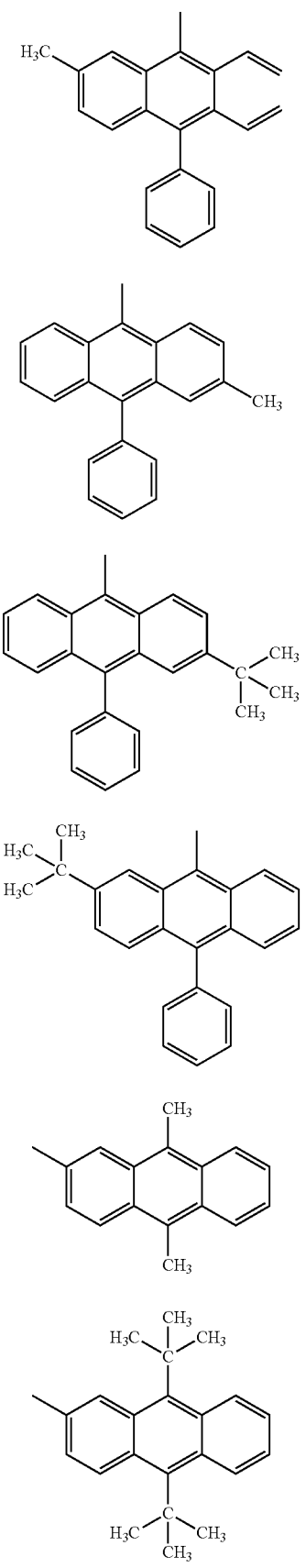
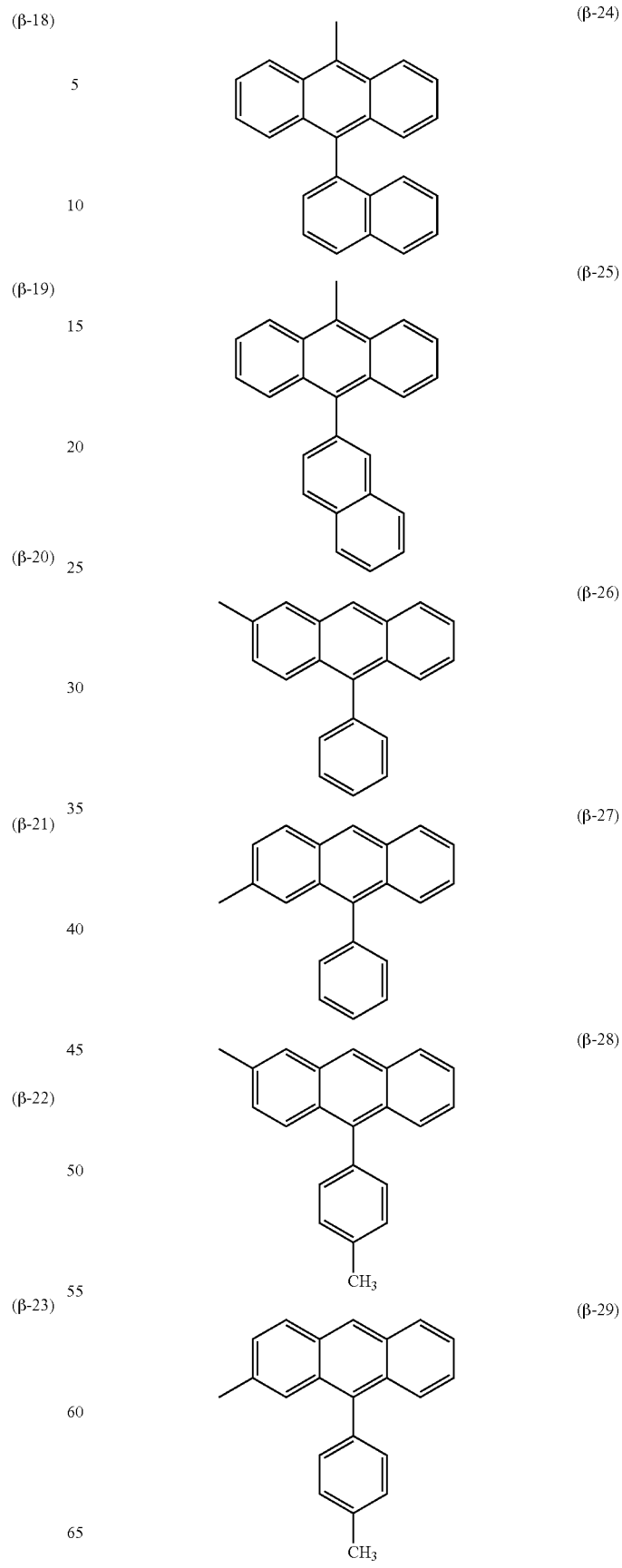

(β-30)
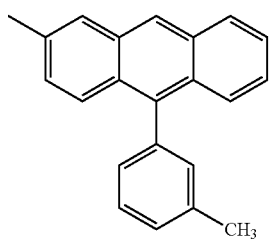
(β-31)
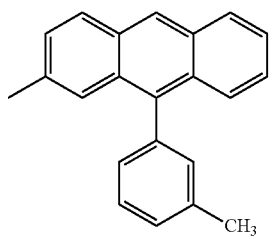
(β-32)
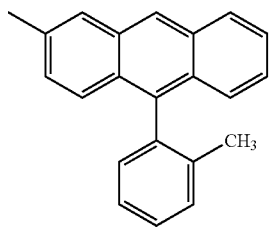
(β-33)
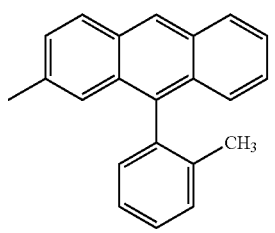
(β-34)
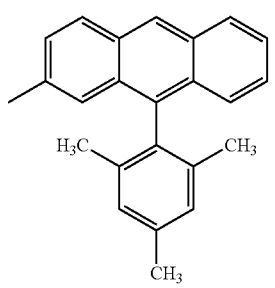
(β-35)
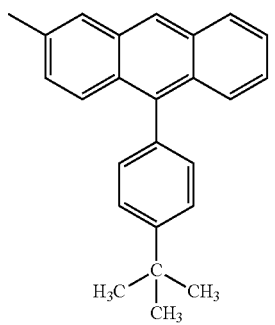
(β-36)
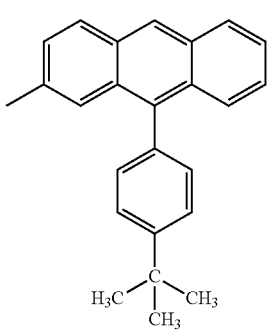
(β-37)
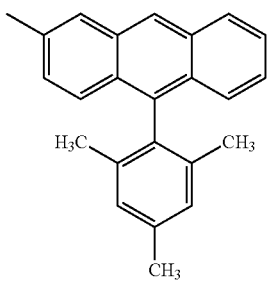
As the aryl group represented by $R^1$, $R^2$, $R^3$, $R^4$, $R^6$, $R^7$, $R^8$, and $R^9$ in the above general formulae (G3) and (G5), for example, groups represented by structural formulae (Ra-1) to (Ra-9) below can be used. Note that a group that can be used as $R^1$, $R^2$, $R^3$, $R^4$, $R^6$, $R^7$, $R^8$, and $R^9$ is not limited to these groups.
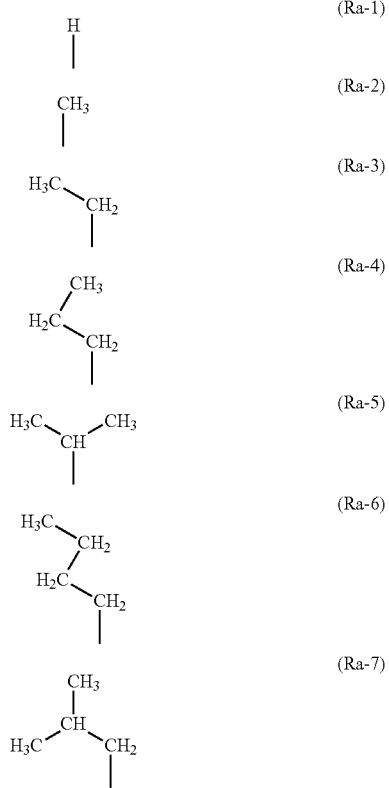

-continued

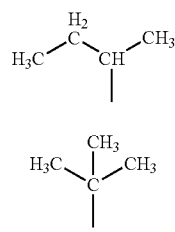
(Ra-8)

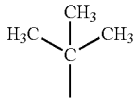
(Ra-9)

As the aryl group represented by $R^5$ in the above general formulae (G3) and (G5) to (G7), for example, groups represented by structural formulae ($R^5$-1) to ($R^5$-17) below can be used. Note that a group that can be used as $R^5$ is not limited to these groups.

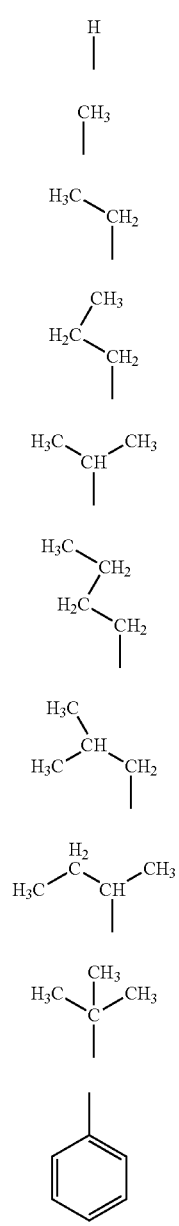

($R^5$-1)
($R^5$-2)
($R^5$-3)
($R^5$-4)
($R^5$-5)
($R^5$-6)
($R^5$-7)
($R^5$-8)
($R^5$-9)
($R^5$-10)

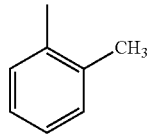
($R^5$-11)

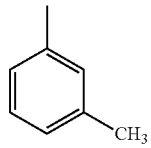
($R^5$-12)

($R^5$-13)
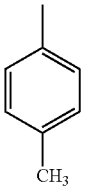

($R^5$-14)
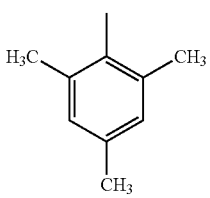

($R^5$-15)
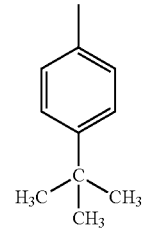

($R^5$-16)
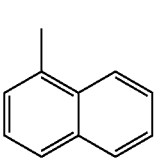

($R^5$-17)
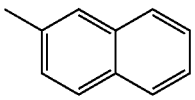

Specific examples of structures of the dibenzo[c,g]carbazole compounds represented by the above general formulae (G1) to (G7) are represented by structural formulae (100) to (136) below, and the like. Note that the dibenzo[c,g]carbazole compounds are not limited to the following examples.

(100) 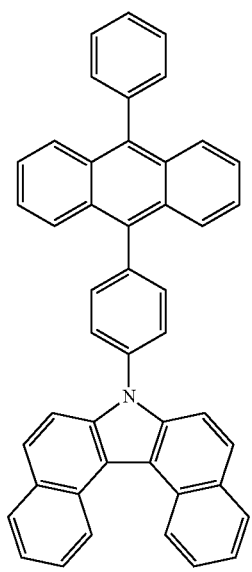
(101) 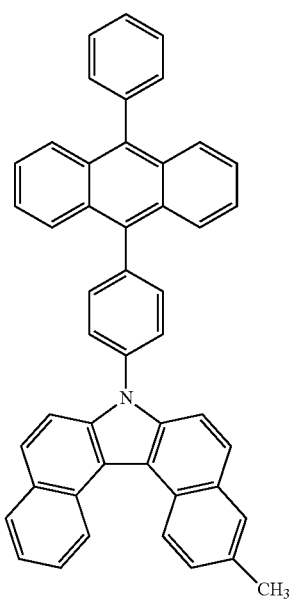
-continued
(102) 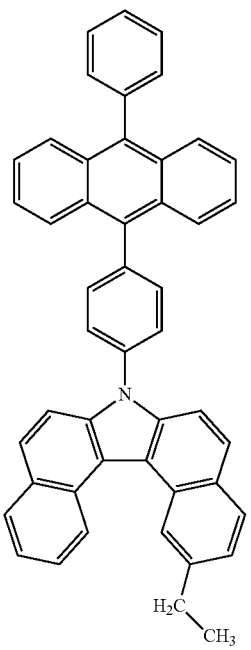
(103) 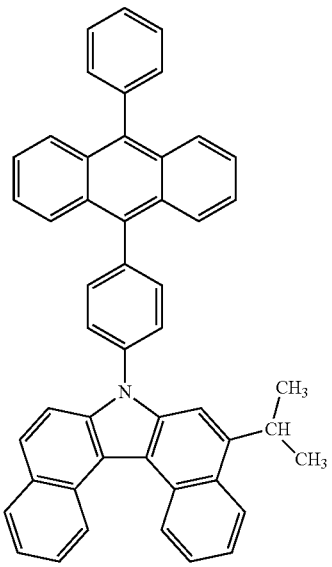

(104)
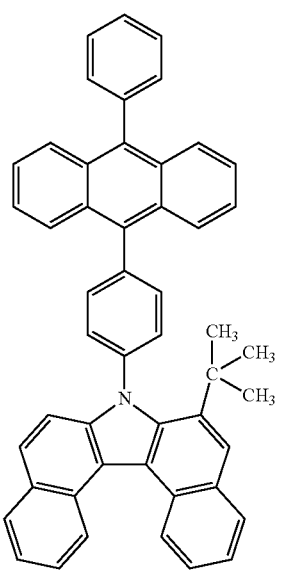
(105)
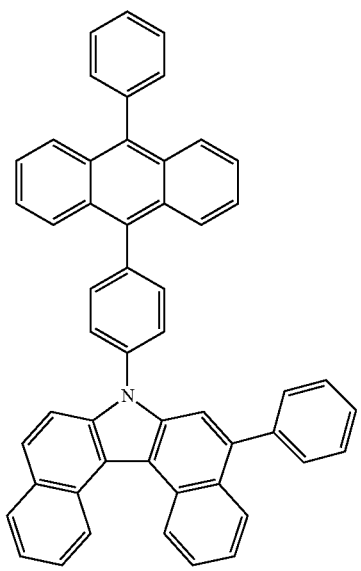
(106)
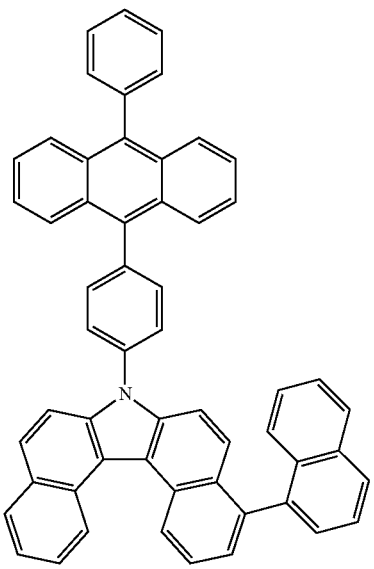
(107)
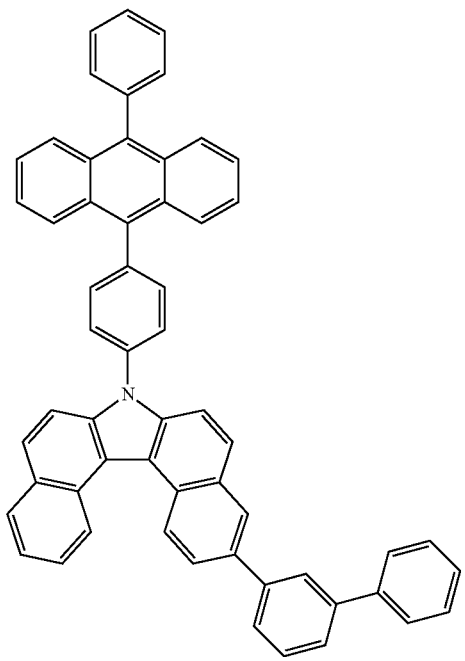

(108)
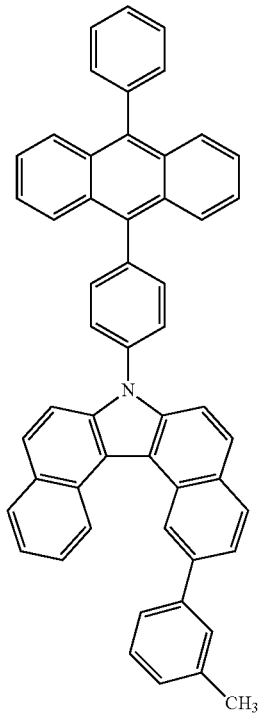
(110)
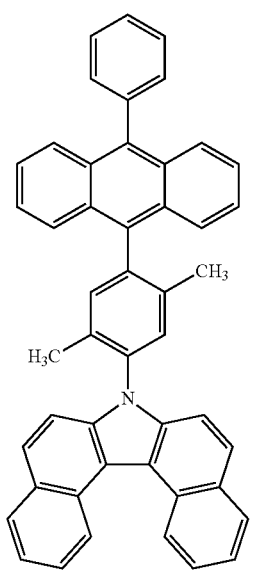
(109)
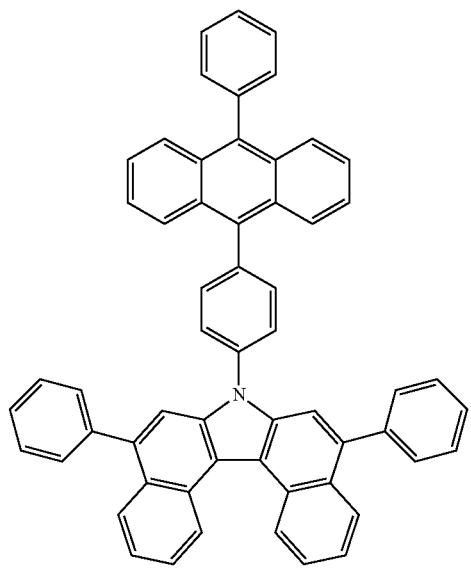
(111)
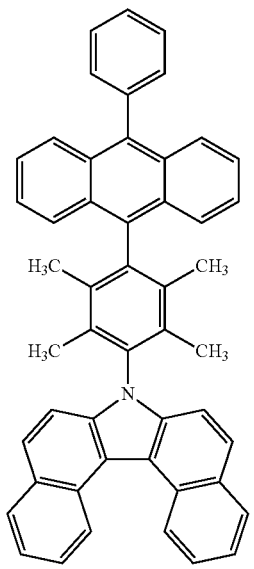

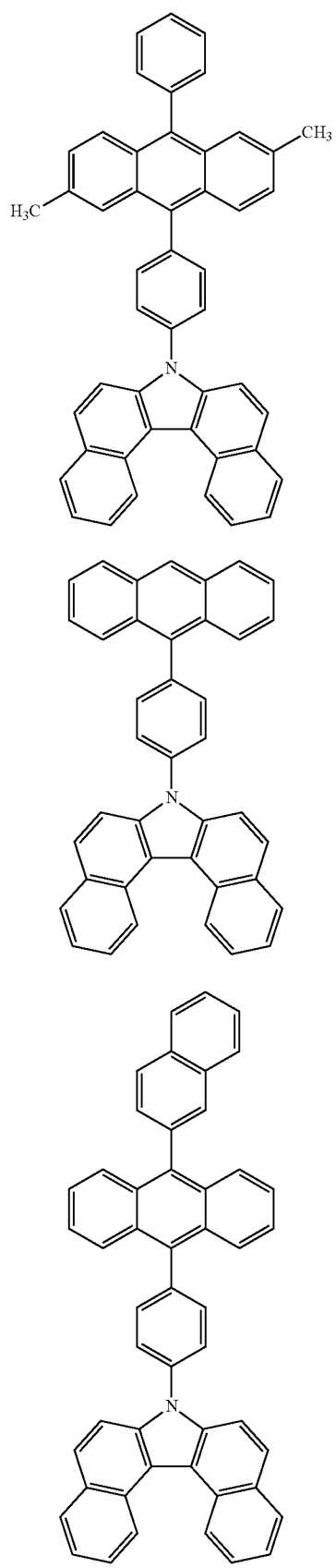

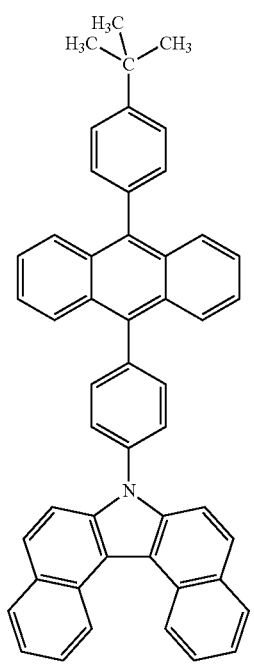
(117)
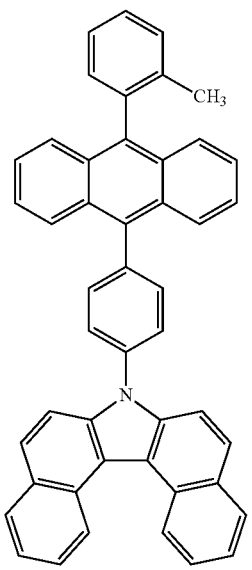
(119)
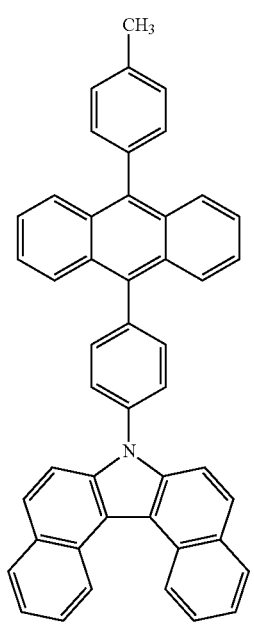
(118)
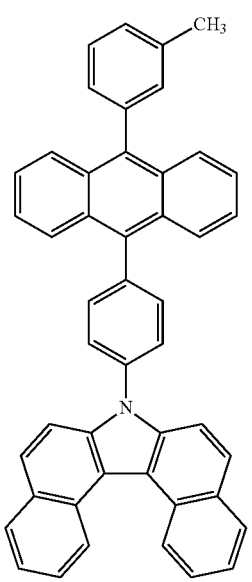
(120)

(121) 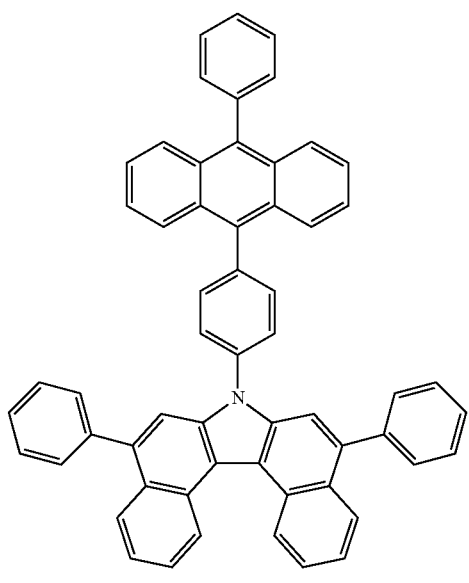
(123) 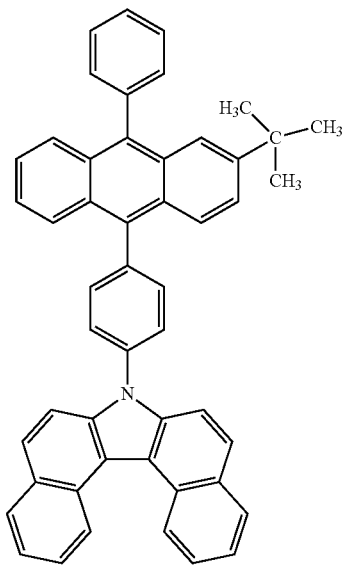
(122) 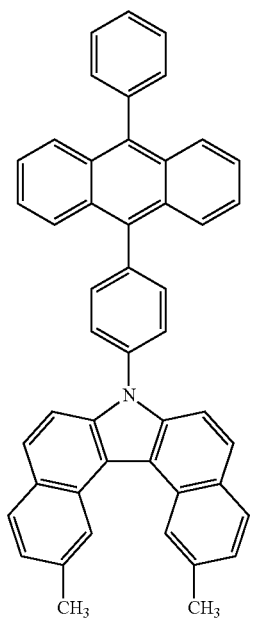
(124) 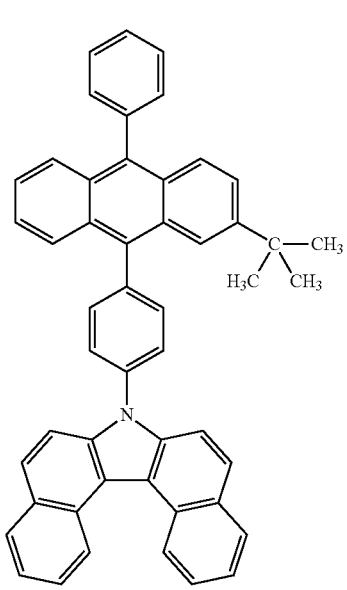

(125)
(126)
(127)
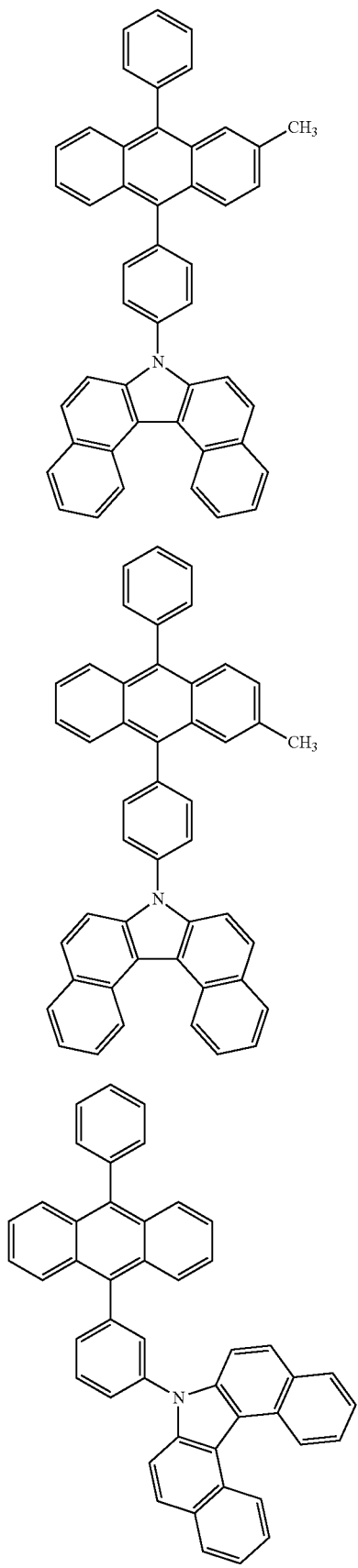
(128)
(129)
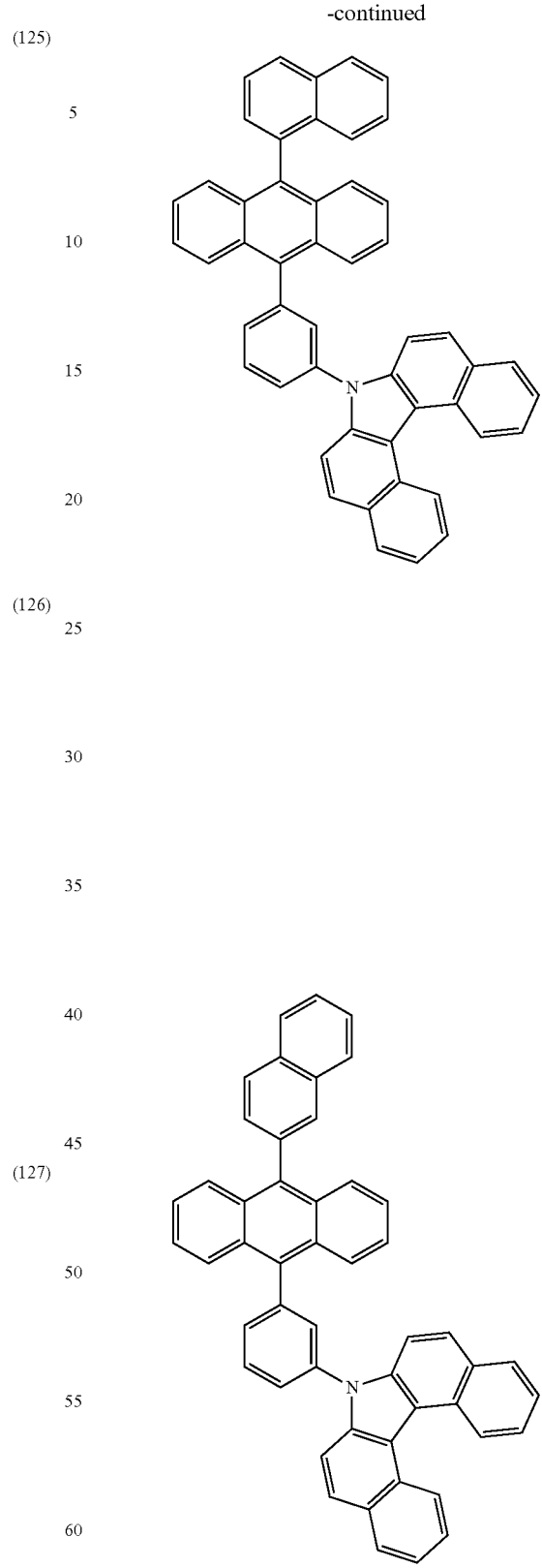

(130)
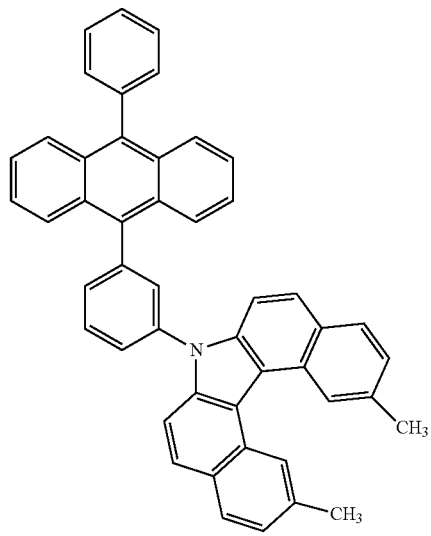
(131)
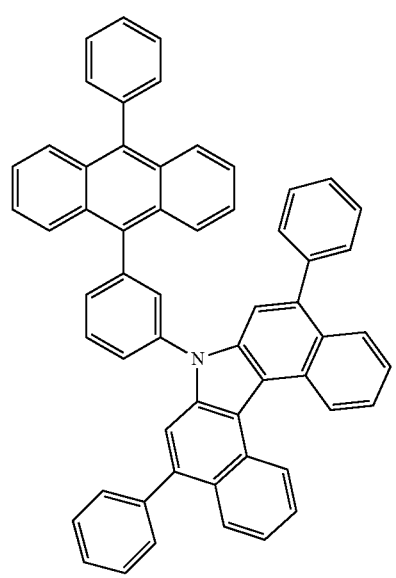
(132)
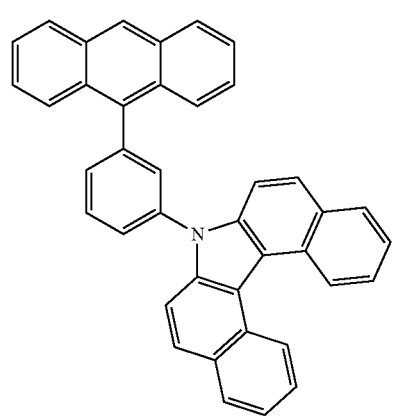
(133)
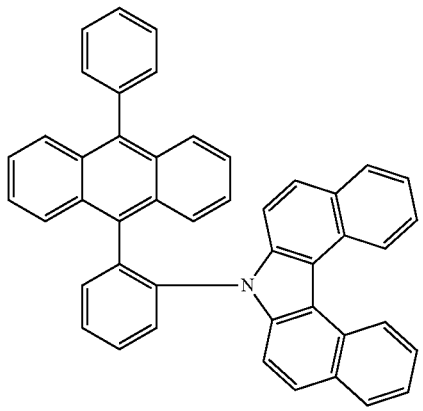
(134)
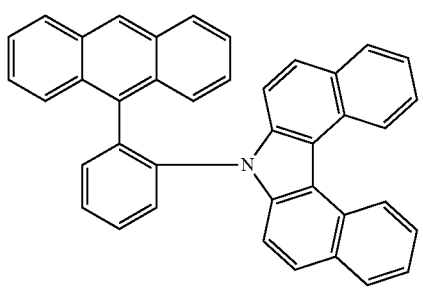
(135)
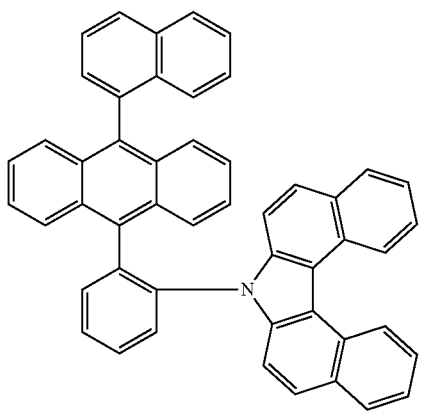
(136)
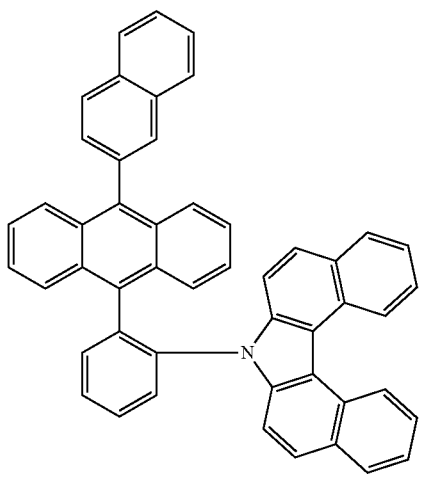
The above-described carbazole compounds have an excellent carrier-transport property and therefore are suitable for a carrier-transport material or a host material; accordingly, a light-emitting element having low driving voltage can be provided. The dibenzo[c,g]carbazole compound has excellent stability to oxidation and reduction. Accordingly, a light-emitting element using the dibenzo[c,g]carbazole compound can be have a long lifetime. Furthermore, the dibenzo[c,g]carbazole compound has a sufficiently wide band gap, and accordingly, even when it is used as a host material of a blue fluorescent material, a light-emitting element with high emission efficiency can be obtained.

(Embodiment 3)

Next, in this embodiment, a method of synthesizing the dibenzo[c,g]carbazole compound, which is used for the light-emitting element of one embodiment of the present invention and represented by the general formula (G1), is described. A variety of reactions can be applied to the synthesis of the dibenzo[c,g]carbazole compound. For example, the reactions described below enable the synthesis of the dibenzo[c,g]carbazole compound. Note that the method of synthesizing the dibenzo[c,g]carbazole compound is not limited to the following synthesis methods.

<Synthesis Method 1 of Dibenzo[c,g]carbazole Compound Represented by General Formula (G1)>

The dibenzo[c,g]carbazole compound (G1) can be synthesized in accordance with a synthesis scheme (A-1) illustrated below. Specifically, an anthracene compound (compound 1) and a dibenzo[c,g]carbazole compound (compound 2) are subjected to coupling, whereby the dibenzo[c,g]carbazole compound (G1) can be obtained.

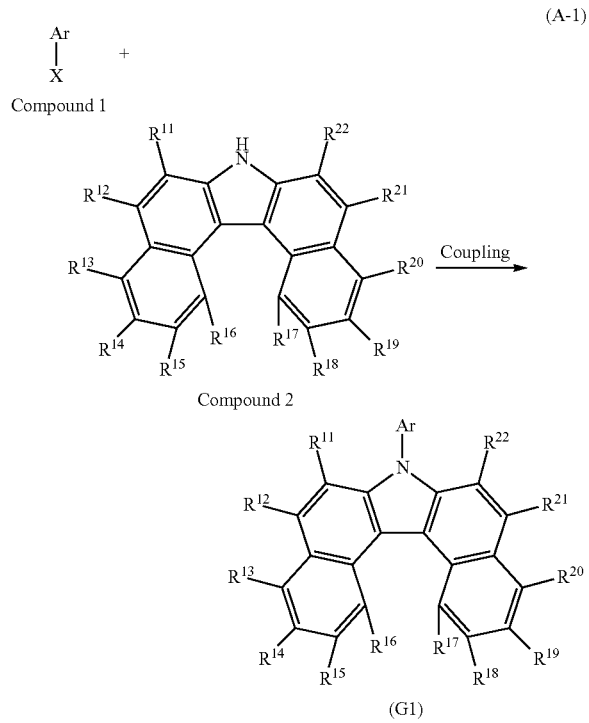

In the synthesis scheme (A-1), Ar represents a substituted or unsubstituted aryl group which has 14 to 30 carbon atoms and includes at least an anthracene skeleton. Further, $R^{11}$ to $R^{22}$ each independently represent any of hydrogen, an alkyl group having 1 to 4 carbon atoms, and an aryl group having 6 to 12 carbon atoms.

In the case where the Hartwig-Buchwald reaction using a palladium catalyst is performed in the synthesis scheme (A-1), X represents a halogen or a triflate group. As the halogen, iodine, bromine, or chlorine is preferable. A palladium catalyst such as bis(dibenzylideneacetone)palladium (0) or palladium(II) acetate and a ligand, such as tri(tert-butyl)phosphine, tri(n-hexyl)phosphine, or tricyclohexylphosphine, is used for the reaction. As a base, an organic base such as sodium tert-butoxide, an inorganic base such as potassium carbonate and the like can be used for the reaction. In the case where a solvent is used, toluene, xylene, benzene, tetrahydrofuran, or the like can be used. Note that reagents which can be used for the reaction are not limited to the above.

In the case where the Ullmann reaction using copper or a copper compound is performed in the synthesis scheme (A-1), X represents a halogen. As the halogen, iodine, bromine, or chlorine is preferable. As a catalyst, copper or a copper compound is used for the reaction. As the base which is used, an inorganic base such as potassium carbonate can be given. Examples of solvents which can be used for the reaction are 1,3-dimethyl-3,4,5,6-tetrahydro-2(1H)-pyrimidinone (DMPU), toluene, xylene, benzene, and the like. In the Ullmann reaction, DMPU or xylene, which has a high boiling point, is preferably used, in which case the object of the synthesis can be obtained in a shorter time and a higher yield at a reaction temperature of 100° C. or more. A reaction temperature of 150° C. or more is further preferred and accordingly DMPU is more preferably used. Note that reagents which can be used for the reaction are not limited to the above.

As described above, the dibenzo[c,g]carbazole compound, which is used for the light-emitting element of one embodiment of the present invention, can be synthesized.

(Embodiment 4)

In this embodiment, an example of a detailed structure of the light-emitting element described in Embodiment 1 as one mode of the present invention is described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113. Note that any layer included in the EL layer 102 contains the dibenzo[c,g]carbazole compound described in Embodiment 2.

By voltage application to such a light-emitting element, holes injected from the first electrode 101 side and electrons injected from the second electrode 103 side recombine in the light-emitting layer 113 to transform a light-emitting substance contained in the light-emitting layer 113 to an excited state. The light-emitting substance in the excited state emits light when the excited substance relaxes to the ground state.

The hole-injection layer 111 included in the EL layer 102 contains a substance having an excellent hole-transport property and an acceptor substance. When electrons are extracted from the substance having an excellent hole-transport property with the acceptor substance, holes are generated. Thus, holes are injected from the hole-injection layer 111 into the light-emitting layer 113 through the hole-transport layer 112.

The charge-generation layer (E) 116 contains a substance having an excellent hole-transport property and an acceptor substance. Electrons are extracted from the substance having an excellent hole-transport property with the acceptor substance, and the extracted electrons are injected from the electron-injection layer 115 having an electron-injection property into the light-emitting layer 113 through the electron-transport layer 114.

The layers in the light-emitting element of this embodiment are specifically described.

As the first electrode (anode) 101 and the second electrode (cathode) 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (e.g., MgAg and AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like. Alternatively, the first electrode (anode) 101 or the second electrode (cathode) 103 can be formed in such a manner that a nanowire of silver (Ag), copper (Cu), aluminum (Al), titanium (Ti), or the like is formed, and a conductive substance such as a conductive organic material or graphene is formed by a coating method, a printing method, or the like.

Furthermore, for example, an insulating film such as an organic film, a transparent semiconductor film, or a silicon nitride film may be provided over the cathode. The insulating film serves as a passivation film and suppresses entry of impurities and moisture. Moreover, surface plasmon loss on the cathode can be reduced, and loss of light energy can be reduced.

As the substance having an excellent hole-transport property used for the hole-injection layer 111, the hole-transport layer 112, and the charge-generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Alternatively, the following carbazole compound can be used: 4,4'-di(N-carbazolyl)biphenyl (abbreviation: CBP), 1,3,5-tris[4-(N-carbazolyl)phenyl]benzene (abbreviation: TCPB), and CzPA. The substances mentioned here are mainly ones that have a hole mobility of $10^{-6}$ cm$^2$/V·s or higher. Note that any substance other than the above substances may be used as long as the hole-transport property is higher than the electron-transport property.

Alternatively, a high molecular compound such as poly (N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: Poly-TPD) can be used.

Note that the dibenzo[c,g]carbazole compound described in Embodiment 2 can be used as the substance having an excellent hole-transport property.

As examples of the acceptor substance that is used for the hole-injection layer 111 and the charge-generation layer (E) 116, an oxide of a metal belonging to any of Group 4 to Group 8 of the periodic table can be given. Specifically, molybdenum oxide is particularly preferable.

The light-emitting layer 113 contains a light-emitting substance. The light-emitting layer 113 may contain only a light-emitting substance; alternatively, a light-emitting substance may be dispersed in a host material.

There is no particular limitation on materials that can be used as the light-emitting substance, and light emitted from these substances may be either fluorescence or phosphorescence. Described below are examples of the light-emitting substance.

Examples of a light-emitting substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tent-butylanthracene-9,10-diyldi-4,1-phenylene)bis [N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''', N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9, 10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-α]fluoranthene-3,10-d iamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitri le (abbreviation: DCJTI), 2-{2-tert-butyl-6-[2-(1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2, 6-bis [2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Note that the dibenzo[c,g]carbazole compound described in Embodiment 2 can be used as a substance that emits fluorescence.

Examples of the substance which emits phosphorescence include bis{2-[3',5 '-bis(trifluoromethyl)phenyl]pyridinato-N,$C^2$}iridium(III) picolinate (abbreviation: Ir(CF$_3$ppy)$_2$ (pic)), bis[2-(4',6'-difluorophenyl)pyridinato-N,$C^2$]iridium (III) acetylacetonate (abbreviation: Flracac), tris(2-phenylpyridinato)iridium(III) (abbreviation: Ir(ppy)$_3$), bis (2-phenylpyridinato)iridium(III) acetylacetonate (abbreviation: Ir(ppy)$_2$(acac)), tris(acetylacetonato) (monophenanthroline)terbium(III) (abbreviation: Tb(acac)$_3$ (Phen)), bis(benzo[h]quinolinato)iridium(III) acetylacetonate (abbreviation: Ir(bzq)$_2$(acac)), bis(2,4-diphenyl-1,3-oxazolato-N, $C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium (III) acetylacetonate (abbreviation: Ir(bt)$_2$(acac)), bis[2-(2'-benzo[4,5-α]thienyl)pyridinato-N,$C^{3'}$]dium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato) iridium(III) (abbreviation: Ir(tppr)$_2$(acac)), bis(2,3,5-triphenylpyrazinato) (dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)], 2,3,7,8,12,13,17,18-octaethyl-21H,23H-porphyrin platinum (II) (abbreviation: PtOEP), tris(1,3-diphenyl-1,3-propanedionato) (monophenanthroline)europium (III) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)).

Although there is no particular limitation on a material that can be used as the host material described above, any of the following substances can be used for the host material, for example: metal complexes such as tris(8-quinolinolato) aluminum(III) (abbreviation: Alq), tris(4-methyl-8-quinolinolato)aluminum(III) (abbreviation: Almq$_3$), bis(10-hydroxybenzo[h] quinolinato)beryllium(II) (abbreviation: BeBq$_2$), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyephenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1, 3,5-benzenetriyl)-tris(1-phenyl-1H-benzimidazole) (abbreviation: TPBI), bathophenanthroline (abbreviation: BPhen), bathocuproine (abbreviation: BCP), and 9-[4-(5-phenyl-1,3 ,4-oxadiazol-2-yl)phenyl]-9H-carbazole (abbreviation: C011); and aromatic amine compounds such as NPB, TPD, and BSPB. In addition, condensed polycyclic aromatic compounds such as anthracene derivatives, phenanthrene derivatives, pyrene derivatives, chrysene derivatives, and dibenzo[g,p]chrysene derivatives can be used. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 2PCAPA, 6,12-dimethoxy-5,11-diphenylchrysene, DBC1, CzPA, 3, 6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-test-butyl-9,10-di(2-naphthyl)anthracene (abbreviation: t-BuDNA), 9,9'-bianthryl (abbreviation: BANT), 9,9'-(stilbene-3,3'-diyediphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a wider energy gap than the light-emitting substance described above is preferably selected from these substances and known substances. Moreover, in the case where the light-emitting substance emits phosphorescence, a substance having triplet excitation energy (energy difference between a ground state and a triplet excited state) which is higher than that of the light-emitting substance is preferably selected as the host material.

Note that the dibenzo[c,g]carbazole compound described in Embodiment 2 can be used for the host material.

Note that the light-emitting layer 113 may have a structure in which two or more layers are stacked. For example, in the case where the light-emitting layer 113 is formed by stacking a first light-emitting layer and a light-emitting second layer in this order from the hole-transport layer side, for example, the first light-emitting layer is formed using a substance with a hole-transport property as the host material and the second light-emitting layer is formed using a substance with an electron-transport property as the host material.

The electron-transport layer 114 is a layer containing a substance having an excellent electron-transport property. For the electron-transport layer 114, a metal complex such as Alq$_3$, Almq$_3$, BeBq$_2$, BAlq, ZnPBO, or ZnBTZ can be used. Further, a heteroaromatic compound such as PBD, OXD-7, TAZ, 3-(4-tert-butylphenyl)-4-(4-ethylphenyl)-5-(4-biphenylyl)-1,2,4-triazole (abbreviation: p-EtTAZ), BPhen, BCP, or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2, 7-diyl)-co-(2,2'-bipyridine-6,6'-diyl)] (abbreviation: PF-BPy) can also be used. The substances given here are mainly ones having an electron mobility of $10^{-6}$ cm$^2$/Vs or higher. Note that any substance other than the above substances may be used for the electron-transport layer 114 as long as the electron-transport property is higher than the hole-transport property.

Note that the dibenzo[c,g]carbazole compound described in Embodiment 2 can be used as a substance having an excellent electron-transport property. Since the dibenzo[c,g]carbazole compound has a wide band gap, even when the compound is used as a material of the electron-transport layer 114 adjacent to the light-emitting layer 113, there is less possibility of deactivation of the excitation energy of the light-emitting substance and a light-emitting element with high emission efficiency can be easily provided.

The electron-transport layer is not limited to a single layer, and may be a stack of two or more layers containing any of the above substances.

The electron-injection layer 115 is a layer containing a substance with a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$), can be used. A rare earth metal compound like erbium fluoride (ErF$_3$) can also be used. Any of the above substances for forming the electron-transport layer 114 can also be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the above materials for forming the electron-transport layer 114 (e.g., a metal complex or a heteroaromatic compound) can be used. As the electron donor, a substance exhibiting an electron-donating property with respect to the organic compound may be used. Specific examples are an alkali metal, an alkaline earth metal, and a rare earth metal are preferable, and lithium, cesium, magnesium, calcium, erbium, and ytterbium. Further, an alkali metal oxide or an alkaline earth metal oxide is preferable, and for example, lithium oxide, calcium oxide, barium oxide, and the like can be given. A Lewis base such as magnesium oxide can also be used. An organic compound such as tetrathiafulvalene (abbreviation: TTF) can also be used.

Note that each of the above hole-injection layer 111, hole-transport layer 112, light-emitting layer 113, electron-transport layer 114, electron-injection layer 115, and the charge-generation layer (E) 116 can be formed by a method such as an evaporation method (e.g., a vacuum evaporation method), an inkjet method, or a coating method.

In the above light-emitting element, current flows due to a potential difference applied between the first electrode 101 and the second electrode 103 and holes and electrons recombine in the EL layer 102, whereby light is emitted. Then, the emitted light is extracted to the outside through one or both of the first electrode 101 and the second electrode 103. Therefore, one or both of the first electrode 101 and the second electrode 103 are electrodes having light-transmitting properties.

When the dibenzo[c,g]carbazole compound described in Embodiment 2 is applied to the light-emitting element, the light-emitting element can have high emission efficiency and low power consumption. In addition, the light-emitting element can emit light with high color purity. Since the dibenzo[c,g]carbazole compound described in Embodiment 2 has an excellent carrier-transport property, the light-emitting element can be driven at low voltage.

Since the dibenzo[c,g]carbazole compound described in Embodiment 2 is electrochemically stable, a light-emitting element having a long lifetime can be easily provided by using the dibenzo[c,g]carbazole compound.

Note that the structure described in this embodiment can be used in combination with any of the structures described in the other embodiments, as appropriate.

(Embodiment 5)

In this embodiment, as one embodiment of the present invention, a light-emitting element (hereinafter referred to as tandem light-emitting element) in which a charge generation layer is provided between a plurality of EL layers is described.

Figure 2A:
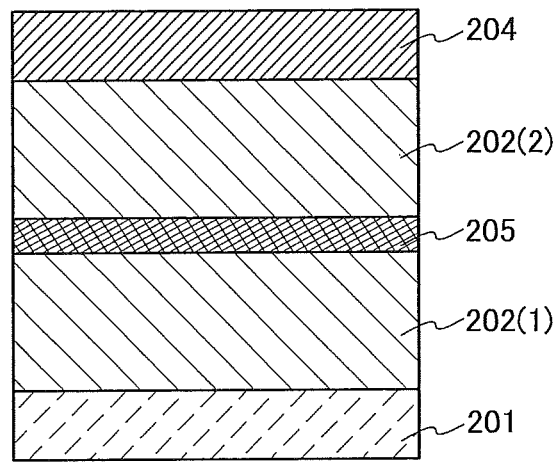
FIGS. 2A and 2B illustrate a structure of a light-emitting element.

The light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 4. In addition, all or any of the plurality of EL layers (the first EL layer 202(1) and the second EL layer 202(2)) may have structures similar to those described in Embodiment 4. In other words, the structures of the first EL layer 202(1) and the second EL layer 202(2) may be the same or different from each other and can be similar to those of the EL layers described in Embodiment 4.

A charge generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or higher). Further, the charge-generation layer 205 functions even when it has lower conductivity than the first electrode 201 or the second electrode 204.

The charge-generation layer 205 may have either a structure in which an electron acceptor (acceptor) is added to an organic compound having an excellent hole-transport property or a structure in which an electron donor (donor) is added to an organic compound having an excellent electron-transport property. Alternatively, both of these structures may be stacked.

In the case of the structure in which an electron acceptor is added to an organic compound having an excellent hole-transport property, as the organic compound having an excellent hole-transport property, for example, an aromatic amine compound such as NPB, TPD, TDATA, MTDATA, or BSPB, or the like can be used. The substances given here are mainly ones having a hole mobility of $10^{-6}$ cm$^2$/Vs or higher. However, any substance other than the above substances may be used as long the hole-transport property is higher than the electron-transport property. Note that the dibenzo[c,g]carbazole compound described in Embodiment 2 can be used as an organic compound having an excellent hole-transport property in the charge-generation layer 205.

Further, as the electron acceptor, 7,7,8, 8-tetracyano-2,3, 5,6-tetrafluoroquinodimethane (abbreviation: F4TCNQ), chloranil, and the like can be given. In addition, oxides of metals belonging to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable owing to their high electron-accepting properties. Among these, molybdenum oxide is especially preferable because it is stable in the air, has a low hygroscopic property, and is easy to handle.

In the case of the structure in which an electron donor is added to an organic compound having an excellent electron-transport property, as the organic compound having an excellent electron-transport property, for example, a metal complex having a quinoline skeleton or a benzoquinoline skeleton, such as Alq, Almq$_3$, BeBq$_2$, or BAlq can be used. A metal complex having an oxazole-based ligand or a thiazole-based ligand, such as ZnPBO or ZnBTZ, or the like can also be used. Other than metal complexes, PBD, OXD-7, TAZ, BPhen, BCP, or the like can be used. The substances given here are mainly ones having an electron mobility of $10^{-6}$ cm$^2$/Vs or higher. Note that substances other than the above substances may be used as long as the electron-transport property is higher than the hole-transport property.

Further, as the electron donor, an alkali metal, a rare earth metal, a metal belonging to Group 2 and Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be also used as the electron donor.

Figure 2B:
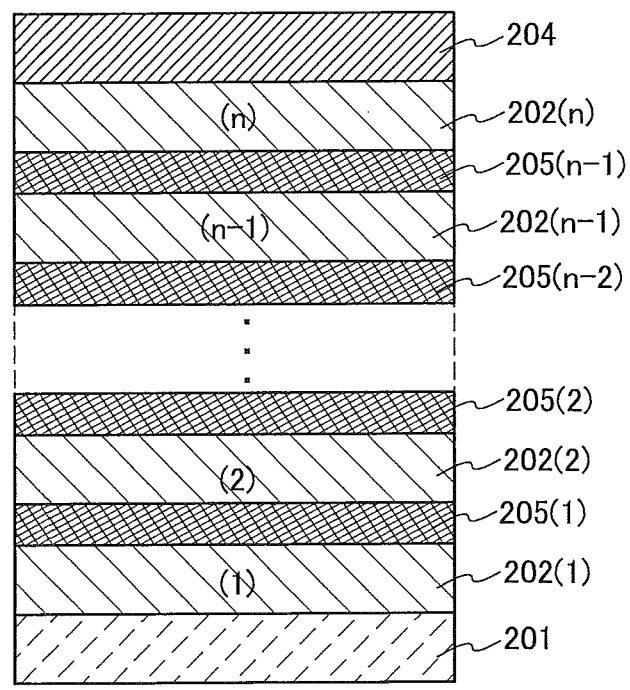

Although this embodiment shows the light-emitting element having two EL layers, the present invention can be similarly applied to a light-emitting element in which n EL layers (202(1) to 202(n)) (n is three or more) are stacked and charge generation layers (205(1) to 205(n−1)) are provided between these EL layers (202(1) to 202(n)) as illustrated in FIG. 2B. In the case where a plurality of EL layers is provided between a pair of electrodes as in the light-emitting element of this embodiment, by providing the charge-generation layer between the EL layers, the light-emitting element can emit light in a high luminance region while the current density is kept low. Since the current density can be kept low, the element can have a long lifetime. When the light-emitting element is applied to light-emitting devices, electronic apparatus, and lighting devices each having a large light-emitting area, voltage drop due to resistance of an electrode material can be reduced, thereby achieving homogeneous light emission in the whole of the light-emitting area.

By making emission colors of the EL layers different, light of a desired color can be obtained from the light-emitting element as a whole. For example, the emission colors of first and second EL layers are complementary in a light-emitting element having the two EL layers, whereby the light-emitting element can emit white light as a whole. Note that the term "complementary" means color relationship in which an achromatic color is obtained when colors are mixed. In other words, emission of white light can be obtained by mixture of light emitted from substances whose emission colors are complementary colors.

Further, the same can be applied to a light-emitting element having three EL layers. For example, the light-emitting element as a whole can emit white light when the emission color of the first EL layer is red, the emission color of the second EL layer is green, and the emission color of the third EL layer is blue.

Since the light-emitting element of this embodiment includes the dibenzo[c,g]carbazole compound described in Embodiment 2, the light-emitting element can have high emission efficiency. In addition, the light-emitting element can be driven at low voltage. Furthermore, the light-emitting element can have a long lifetime. In addition, the light-emitting element containing the dibenzo[c,g]carbazole compound described in Embodiment 2 can certainly provide light which originates from the emission substance; therefore, it is easy to adjust the color of light emitted from the light-emitting element as a whole.

Note that the structure described in this embodiment can be used in combination with any of the structures described in the other embodiments, as appropriate.

(Embodiment 6)

In this embodiment, a light-emitting device including a light-emitting element in which the dibenzo[c,g]carbazole compound described in Embodiment 2 is used in an EL layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 3A and 3B.

Figure 3A:
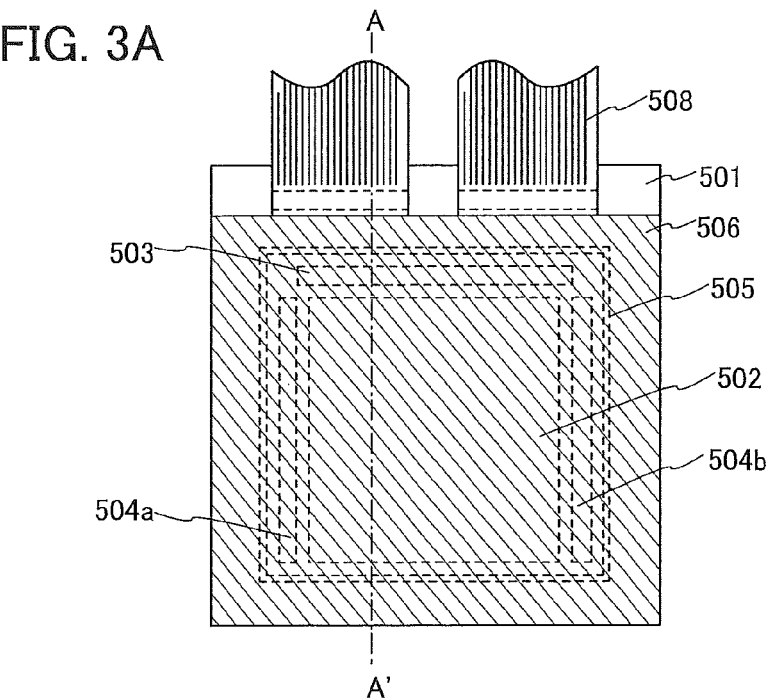
FIGS. 3A and 3B illustrate a light-emitting device.
Figure 3B:
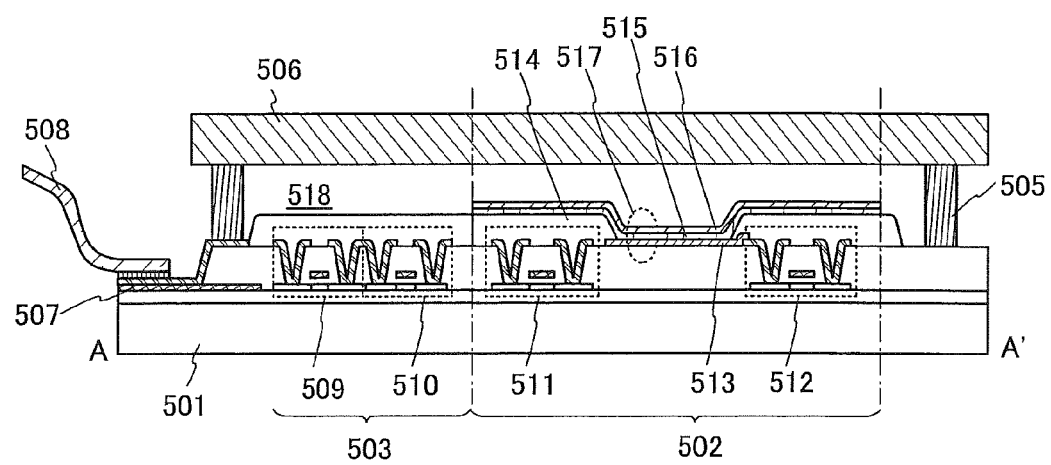

FIG. 3A is a top view illustrating a light-emitting device and FIG. 3B is a cross-sectional view taken along the chain line A-A' in FIG. 3A. The active matrix light-emitting device according to this embodiment includes a pixel portion 502 provided over an element substrate 501, a driver circuit portion (a source line driver circuit) 503, and driver circuit portions (gate line driver circuits) 504a and 504b. The pixel portion 502, the driver circuit portion 503, and the driver circuit portions 504a and 504b are sealed between the element substrate 501 and the sealing substrate 506 with a sealant 505.

A lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portions 504a and 504b. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel FET 509 and a p-channel FET 510. Note that a circuit included in the driver circuit portion may be formed using various CMOS circuits, PMOS circuits, or NMOS circuits, and any of a staggered type FET and a reversestaggered type FET can be used. Further, the crystallinity of a semiconductor film used in the FET is not limited and can be amorphous or crystalline. Additionally, an oxide semiconductor may be used for the semiconductor film. Although this embodiment shows a driver integrated type in which the driver circuit is formed over the substrate, the driver circuit is not necessarily formed over the substrate, and may be formed outside the substrate.

The pixel portion 502 is formed of a plurality of pixels each of which includes a switching FET 511, a current control FET 512, and a first electrode (anode) 513 which is electrically connected to a wiring (a source electrode or a drain electrode) of the current control FET 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be formed using either a negative photosensitive resin or a positive photosensitive resin. The material of the insulator 514 is not limited to an organic compound and an inorganic compound such as silicon oxide or silicon oxynitride can also be used.

An EL layer 515 and a second electrode (cathode) 516 are stacked over the first electrode (anode) 513. In the EL layer 515, at least a light-emitting layer is provided. Further, in the EL layer 515, a hole-injection layer, a hole-transport layer, an electron-transport layer, an electron-injection layer, a charge generation layer, and the like can be provided as appropriate in addition to the light-emitting layer. Note that the dibenzo[c,g]carbazole compound described in Embodiment 2 can be applied to the hole-injection layer, the hole-transport layer, the light-emitting layer, the electron-transport layer, the charge generation layer, and on the like.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to the FPC 508 which is an external input terminal.

Although the cross-sectional view of FIG. 3B illustrates only one light-emitting element 517, a plurality of light-emitting elements is arranged in a matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

The sealing substrate 506 is attached to the element substrate 501 with the sealant 505, whereby the light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), poly(vinyl fluoride) (PVF), a polyester, an acrylic resin, or the like can be used.

As described above, an active matrix light-emitting device can be obtained.

A light-emitting element including the dibenzo[c,g]carbazole compound described in Embodiment 2 is used in the light-emitting device in this embodiment, and thus a light-emitting device having favorable characteristics can be obtained. Specifically, since the dibenzo[c,g]carbazole compound described in Embodiment 2 has a large energy gap and high triplet excitation energy and can suppress energy transfer from a light-emitting substance, a light-emitting element having high emission efficiency can be provided, and accordingly a light-emitting device having reduced power consumption can be provided. In addition, a light-emitting element having low driving voltage can be obtained, and accordingly a light-emitting device having low driving voltage can be obtained. Further, since a light-emitting element using the dibenzo[c,g]carbazole compound described in Embodiment 2 is a light-emitting element having a long lifetime, a light-emitting device with high reliability can be provided.

Note that the structure described in this embodiment can be used in combination with any of the structures described in the other embodiments, as appropriate.

(Embodiment 7)

In this embodiment, examples of a variety of electronic devices which are completed using a light-emitting device are described with reference to FIGS. 4A to 4D. The light-emitting device is fabricated using the light-emitting element including the dibenzo[c,g]carbazole compound described in Embodiment 2.

Examples of the electronic devices to which the light-emitting device is applied include television devices (also referred to as TV or television receivers), monitors for computers and the like, digital cameras, digital video cameras, digital photo frames, mobile phones (also referred to as cellular phone or mobile phone device), portable game machines, portable information terminals, audio playback devices, and large game machines such as pin-ball machines. Specific examples of the electronic devices are illustrated in FIGS. 4A to 4D.

Figure 4A:
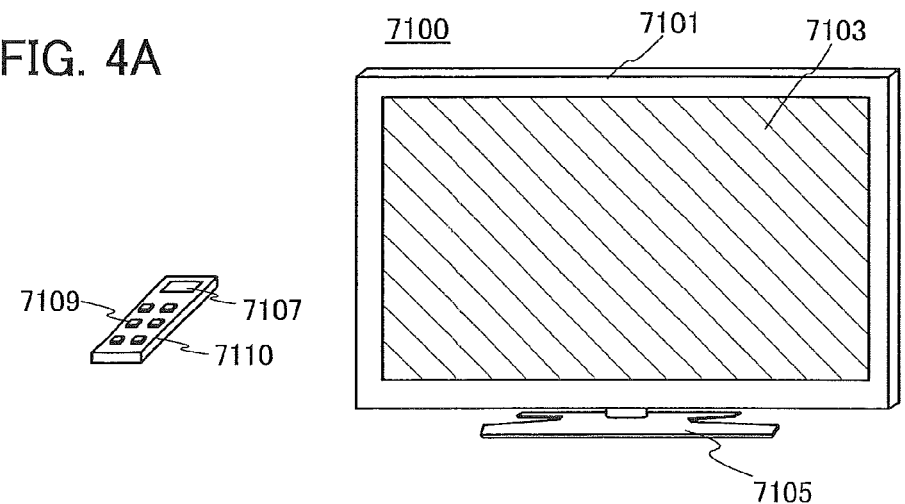
FIGS. 4A to 4D illustrate electronic devices.

FIG. 4A illustrates an example of a television device. In a television device 7100, a display portion 7103 is incorporated in a housing 7101. Images can be displayed by the display portion 7103, and a light-emitting device can be used for the display portion 7103. Here, the housing 7101 is supported by a stand 7105. Note that the display portion 7103 includes the light-emitting device in which light-emitting elements each containing the dibenzo[c,g]carbazole compound described in Embodiment 2 are arranged in a matrix.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 4B:
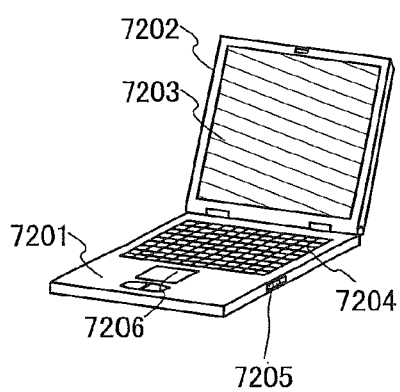

FIG. 4B illustrates a computer including a main body 7201, a housing 7202, a display portion 7203, a keyboard 7204, an external connecting port 7205, a pointing device 7206, and the like. This computer is manufactured by using a light-emitting device of for the display portion 7203. Note that the display portion 7203 includes the light-emitting device in which light-emitting elements including the dibenzo[c,g]carbazole compound described in Embodiment 2 are arranged in a matrix.

Figure 4C:
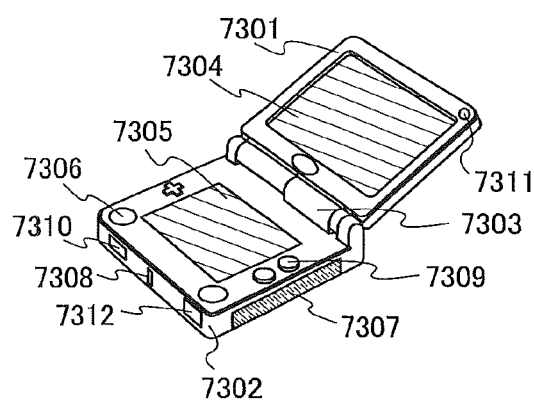

FIG. 4C illustrates a portable game machine iincluding two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. Note that the display portions 7304 and 7305 include a light-emitting device in which light-emitting elements each containing the dibenzo[c,g]carbazole compound described in Embodiment 2 are arranged in a matrix.

In addition, the portable game machine illustrated in FIG. 4C includes a speaker portion 7306, a recording medium insertion portion 7307, an LED lamp 7308, an input means (an operation key 7309, a connection terminal 7310, microphone 7312), a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and the like. It is needless to say that the structure of the portable game machine is not limited to the above as long as a light-emitting device is used for at least either the display portion 7304 or the display portion 7305, or both, and may include other accessories as appropriate.

The portable game machine illustrated in FIG. 4C has a function of reading out a program or data stored in a storage medium to display it on the display portion, and a function of sharing information with another portable game machine by wireless communication. The portable game machine illustrated in FIG. 4C can have a variety of functions without limitation to the above functions.

Figure 4D:
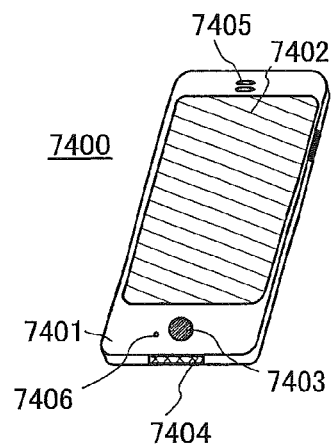

FIG. 4D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402. Note that the display portion 7402 includes the light-emitting device in which light-emitting elements each containing the dibenzo[c,g]carbazole compound described in Embodiment 2 are arranged in a matrix.

When the display portion 7402 of the mobile phone 7400 illustrated in FIG. 4D is touched with a finger or the like, data can be input into the mobile phone 7400. Further, operations such as making a call and composing an e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be input. In this case, it is preferable to display a keyboard or number buttons on almost the entire screen of the display portion 7402.

When a detection device such as a gyro sensor or an acceleration sensor is provided inside the mobile phone 7400, display on the screen of the display portion 7402 can be automatically changed by determining the orientation of the mobile phone 7400 (whether the mobile phone is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when it is determined that input by touching the display portion 7402 is not performed within a specified period on the basis of a signal detected by an optical sensor in the display portion 7402, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a sensing light source which emits a near-infrared light in the display portion, an image of a finger vein, a palm vein, or the like can be taken.

Figure 5A:
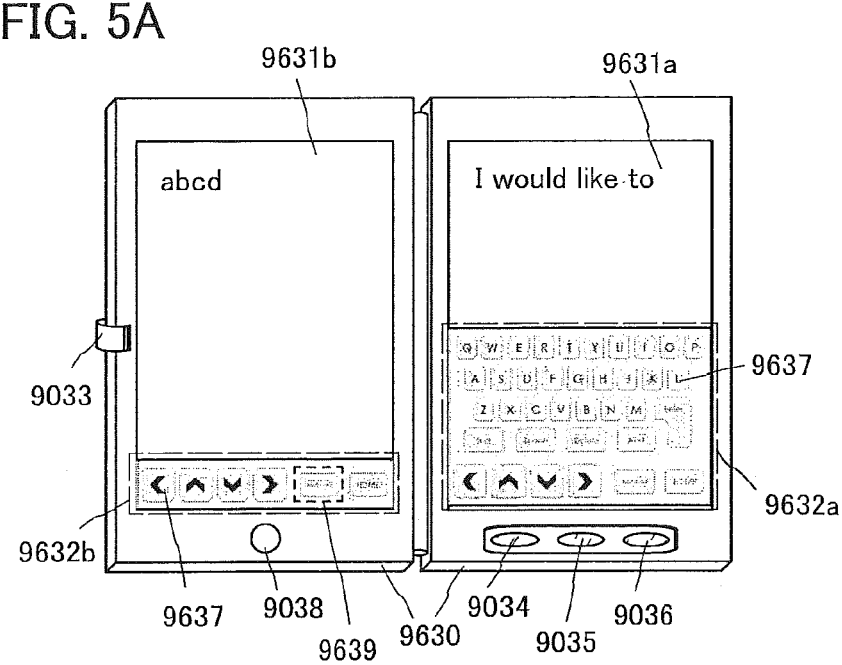
FIGS. 5A to 5C illustrate an electronic device.
Figure 5B:
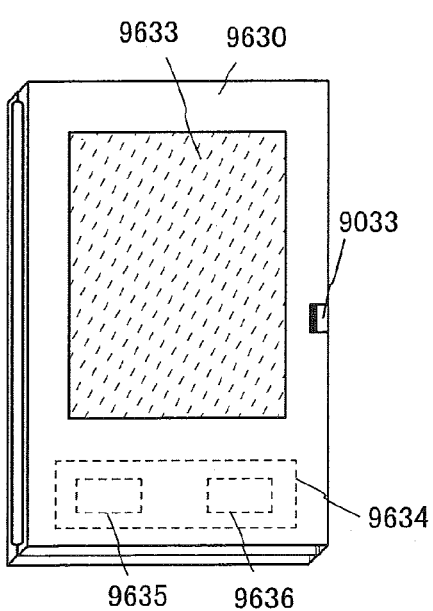

FIGS. 5A and 5B illustrate a foldable tablet terminal. In FIG. 5A, the tablet terminal is opened. The tablet terminal includes a housing 9630, a display portion 9631*a*, a display portion 9631*b*, a display mode switch 9034, a power switch 9035, a power saver switch 9036, a clasp 9033, and an operation switch 9038. The tablet terminal is manufactured using a light-emitting device for one or both of the display portions 9631*a* and 9631*b*. Note that at least one of the display portions 9631*a* and 9631*b* includes the light-emitting device in which light-emitting elements each containing the dibenzo[c,g]carbazole compound described in Embodiment 2 are arranged in a matrix.

Part of the display portion 9631*a* can be a touch panel region 9632*a*, and data can be input by touching operation keys 9637 that are displayed. Note that FIG. 5A shows, as an example, that half of the area of the display portion 9631*a* has only a display function and the other half of the area has a touch panel function. However, the structure of the display portion 9631*a* is not limited to this, and all the area of the display portion 9631*a* may have a touch panel function. For example, all the area of the display portion 9631*a* can display keyboard buttons and serve as a touch panel while the display portion 9631*b* can be used as a display screen.

Like the display portion 9631*a*, part of the display portion 9631*b* can be a touch panel region 9632*b*. When a finger, a stylus, or the like touches the place where a button 9639 for switching to keyboard display is displayed in the touch panel, keyboard buttons can be displayed on the display portion 9631*b*.

Touch input can be performed concurrently on the touch panel regions 9632*a* and 9632*b*.

The switch 9034 for switching display modes can switch display orientation (e.g., between landscape mode and portrait mode) and select a display mode (switch between monochrome display and color display), for example. With the switch 9036 for switching to power-saving mode, the luminance of display can be optimized in accordance with the amount of external light at the time when the tablet terminal is in use, which is detected with an optical sensor incorporated in the tablet terminal. The tablet terminal may include another detection device such as a gyro sensor or an acceleration sensor in addition to the optical sensor.

Although FIG. 5A shows the example where the display area of the display portion 9631*a* is the same as that of the display portion 9631*b*, there is no particular limitation on the display portions 9631*a* and 9631*b*. They may differ in size and/or image quality. For example, one of them may be a display panel that can display higher-definition images than the other.

FIG. 5B illustrates the tablet terminal which is closed. The tablet terminal includes the housing 9630, a solar battery 9633, a charge/discharge control circuit 9634, a battery 9635, and a DC to DC converter 9636.

Since the tablet terminal can be folded in two, the housing 9630 can be closed when the tablet terminal is not in use. Thus, the display portions 9631*a* and 9631 *b* can be protected, thereby providing a tablet terminal with high endurance and high reliability for long-term use.

The tablet terminal illustrated in FIGS. 5A and 5B can also have a function of displaying various kinds of data, such as a calendar, a date, or the time, on the display portion as a still image, a moving image, and a text image, a function of displaying, a touch-input function of operating or editing data displayed on the display portion by touch input, a function of controlling processing by various kinds of software (programs), and the like.

The solar battery 9633, which is attached on the surface of the tablet terminal, supplies electric power to a touch panel, a display portion, an image signal processor, and the like. Note that a structure in which the solar battery 9633 is provided is preferable because the battery 9635 which supplies electric power to the display portion 9631*a* and/or the display portion 9631*b* can be charged. When a lithium ion battery is used as the battery 9635, there is an advantage of downsizing or the like.

Figure 5C:
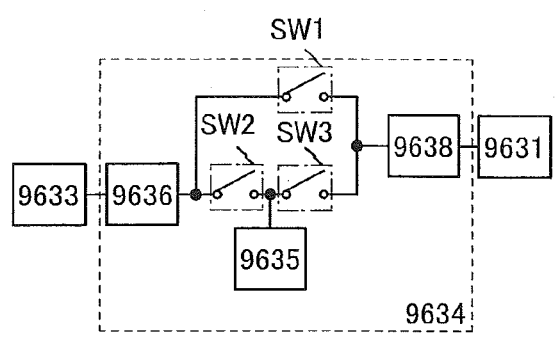

The structure and operation of the charge/discharge control circuit 9634 illustrated in FIG. 5B are described with reference to a block diagram in FIG. 5C. FIG. 5C illustrates the solar battery 9633, the battery 9635, the DC to DC converter 9636, a converter 9638, switches SW1 to SW3, and the display portion 9631. The battery 9635, the DC to DC converter 9636, the converter 9638, and the switches SW1 to SW3 correspond to those in the charge/discharge control circuit 9634 illustrated in FIG. 5B.

An example of the operation performed when power is generated by the solar battery 9633 using external light is described. The voltage of power generated by the solar battery 9633 is raised or lowered by the DC to DC converter 9636 so as to be a voltage for charging the battery 9635. Then, when power from the solar battery 9633 is used for the operation of the display portion 9631, the switch SW1 is turned on and the voltage of the power is raised or lowered by the converter 9638 so as to be a voltage needed for the display portion 9631. When images are not displayed on the display portion 9631, the switch SW1 is turned off and the switch SW2 is turned on so that the battery 9635 is charged.

Here, the solar battery 9633 is shown as an example of a power generation means; however, there is no particular limitation on a way of charging the battery 9635, and the battery 9635 may be charged with another power generation means such as a piezoelectric element or a thermoelectric conversion element (Peltier element). For example, the battery 9635 may be charged with a non-contact power transmission module that transmits and receives power wirelessly (without contact) to charge the battery or with a combination of other charging means.

As described above, the light-emitting elements included in the light-emitting device of the aforementioned electronic devices contain the dibenzo[c,g]carbazole compound described in Embodiment 2. Therefore, the light-emitting elements exhibit high emission efficiency, have a low driving voltage, and show a long lifetime. Hence, it is possible to produce electronic devices with reduced power consumption, low driving voltage, and high reliability. It is needless to say that an embodiment of the present invention is not limited to the electronic device illustrated in FIGS. 5A to 5C as long as the display portion described in the above embodiment is included.

As described above, the electronic devices can be obtained by application of the light-emitting device of one embodiment of the present invention. The light-emitting device has an extremely wide application range, and can be applied to electronic devices in a variety of fields.

Note that the structure described in this embodiment can be used in combination with any of the structures described in the other embodiments, as appropriate.

(Embodiment 8)

In this embodiment, examples of lighting devices which are completed using a light-emitting device are described with reference to FIG. 6. The light-emitting device is fabricated using a light-emitting element including the dibenzo [c,g]carbazole compound described in Embodiment 2.

FIG. 6 illustrates an example in which the light-emitting device is used as an indoor lighting device 8001. Since the light-emitting device can have a larger area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used at a surface of a table, a lighting device 8004 which has a function as a table can be obtained. When the light-emitting device is used as part of other furniture, a lighting device which has a function as the furniture can be obtained.

As described above, a variety of lighting devices to which the light-emitting device is applied can be obtained. Note that the lighting device described in this embodiment includes a light-emitting device in which light-emitting elements each containing the dibenzo[c,g]carbazole compound described in Embodiment 2 are arranged in a matrix. The light-emitting element included in the light-emitting device can have high emission efficiency. In addition, the light-emitting element can be driven at low voltage. Furthermore, the light-emitting element can have a long lifetime. Accordingly, the lighting device to which a light-emitting device including the light-emitting elements can be a lighting device having reduced power consumption. In addition, the light-emitting device can have low driving voltage. Furthermore, the light-emitting device can have high reliability. Note that such lighting devices are also embodiments of the present invention.

Note that the structure described in this embodiment can be used in combination with any of the structures described in the other embodiments, as appropriate.

(Embodiment 9)

In this embodiment, a light-emitting device manufactured using the light-emitting element of one embodiment of the present invention is described with reference to FIGS. 34A and 34B.

Figure 34A:
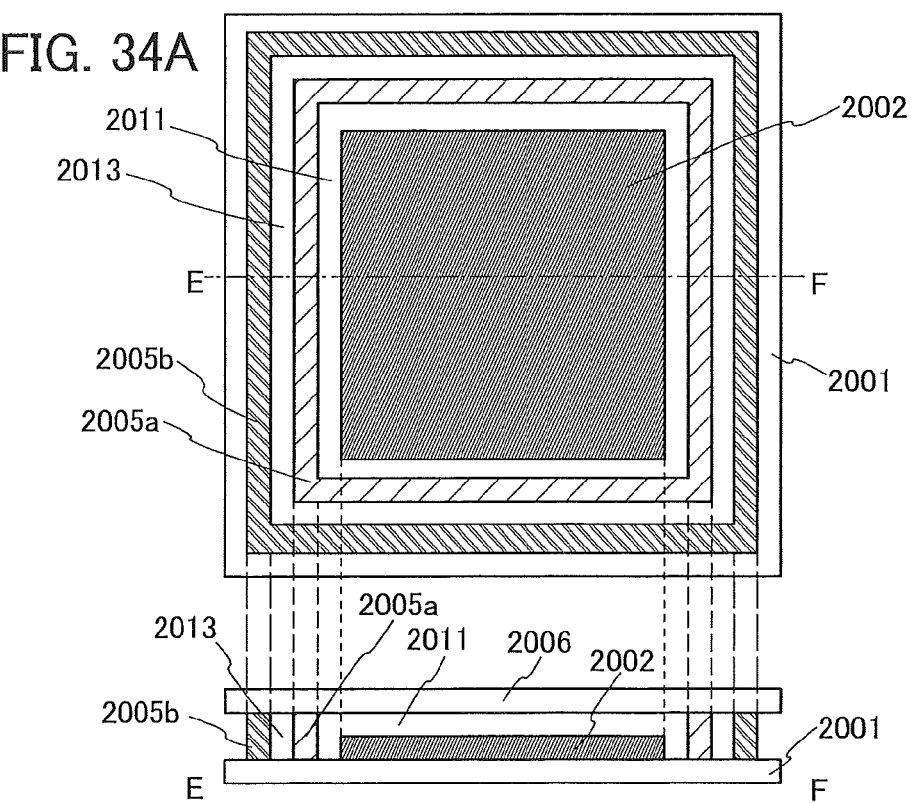
FIGS. 34A and 34B illustrate a light-emitting device of one embodiment of the present invention.

In FIG. 34A, a plan view of a light-emitting device described in this embodiment and a cross-sectional view taken along the dashed-dotted line E-F in the plan view are illustrated.

The light-emitting device illustrated in FIG. 34A includes a light-emitting portion 2002 including a light-emitting element over a first substrate 2001. The light-emitting device has a structure in which a first sealant 2005a is provided so as to surround the light-emitting portion 2002 and a second sealant 2005b is provided so as to surround the first sealant 2005a (i.e., a double sealing structure).

Thus, the light-emitting portion 2002 is positioned in a space surrounded by the first substrate 2001, the second substrate 2006, and the first sealant 2005a. The light-emitting portion 2002 has the light-emitting element containing the dibenzo[c,g]carbazole compound shown in Embodiment 2.

Note that in this specification, the first sealant 2005a and the second sealant 2005b are not necessarily in contact with the first substrate 2001 and the second substrate 2006. For example, the first sealant 2005a may be in contact with an insulating film or a conductive film formed over the first substrate 2001.

In the above structure, the first sealant 2005a is a resin layer containing a desiccant and the second sealant 2005b is a glass layer, whereby an effect of suppressing entry of impurities such as moisture and oxygen from the outside (hereinafter, referred to as a sealing property) can be increased.

The first sealant 2005a is the resin layer as described above, whereby the glass layer that is the second sealant 2005b can be prevented from having breaking or cracking (hereinafter, collectively referred to as a crack). Further, in the case where the sealing property of the second sealant 2005b is not sufficient, even when impurities such as moisture and oxygen enter a first space 2013, entry of the impurities into a second space 2011 can be suppressed owing to a high sealing property of the first sealant 2005a. Thus, deterioration of an organic compound, a metal material, and the like contained in the light-emitting element by the impurities can be suppressed.

Figure 34B:
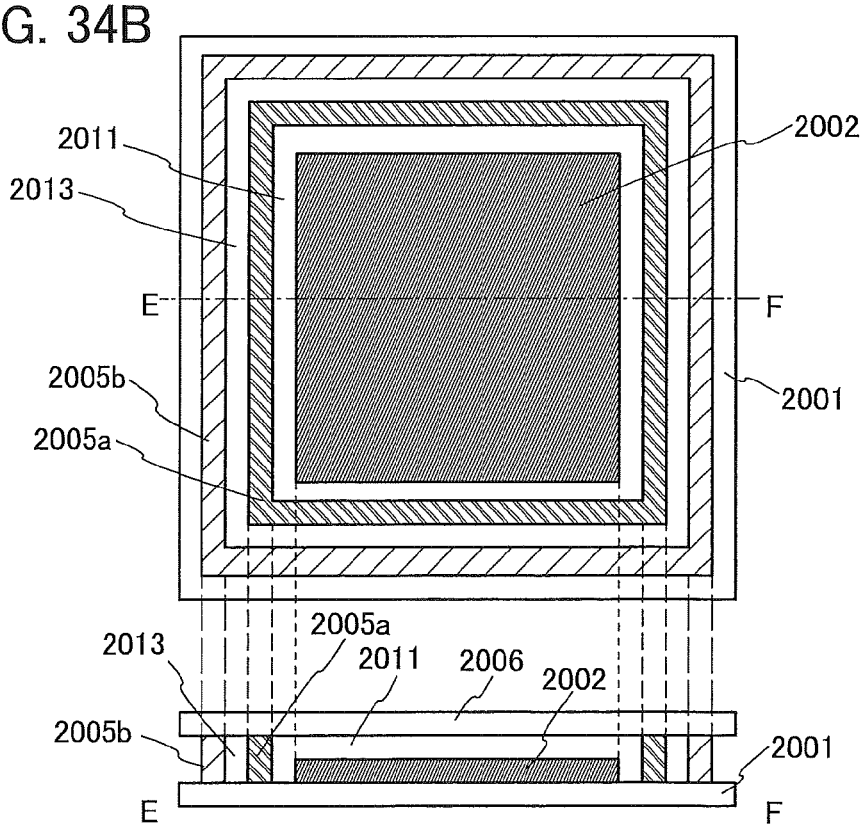

In addition, the structure illustrated in FIG. 34B can be employed: the first sealant 2005a is a glass layer and the second sealant 2005b is a resin layer containing a desiccant.

In each of the light-emitting devices described in this embodiment, distortion due to external force or the like increases toward the outer portion of the light-emitting device. Hence, a glass layer is used for the first sealant 2005a which has relatively small distortion due to external force or the like, and a resin layer which has excellent impact resistance and excellent heat resistance and which is not easily broken by deformation due to external force or the like is used for the second sealant 2005b, whereby entry of moisture and oxygen into the first space 2013 can be suppressed.

In addition to the above structure, a material serving as a desiccant may be contained in each of the first space 2013 and the second space 2011.

In the case where the first sealant 2005a or the second sealant 2005b is a glass layer, for example, a glass frit or a glass ribbon can be used. Note that at least a glass material is contained in a glass frit or a glass ribbon.

The glass frit contains a glass material as a frit material. The glass frit may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass. The glass frit preferably contains at least one or more kinds of transition metals to absorb infrared light.

Further, in the case where a glass layer is formed using any of the above glass frits, for example, a fit paste is applied to a substrate and is subjected to heat treatment, laser light irradiation, or the like. The fit paste contains the frit material and a resin (also referred to as a binder) diluted by an organic solvent. The frit paste can be formed using a known material, and a variety of structures can be employed for the frit paste. An absorber that absorbs light having a wavelength of laser light may be added to the frit material. For example, an Nd:YAG laser or a semiconductor laser is preferably used as the laser. The shape of laser light may be circular or quadrangular.

Note that the thermal expansion coefficient of the glass layer to be formed is preferably close to that of the substrate. The closer the thermal expansion coefficients are, the more generation of a crack in the glass layer or the substrate due to thermal stress can be suppressed.

Although any of known materials, for example, photocurable resins such as an ultraviolet curable resin and thermosetting resins can be used in the case where the first sealant 2005a or the second sealant 2005b is a resin layer, it is particularly preferable to use a material which does not transmit moisture or oxygen. In particular, a photocurable resin is preferably used. The light-emitting element contains a material having low heat resistance in some cases. A photocurable resin, which is cured by light irradiation, is preferably used, in which case change in film quality and deterioration of an organic compound itself caused by heating of the light-emitting element can be suppressed. Furthermore, any of the organic compounds that can be used for the light-emitting element of one embodiment of the present invention may be used.

As the desiccant contained in the resin layer, the first space 2013, or the second space 2011, a known material can be used. As the desiccant, a substance which adsorbs moisture by chemical adsorption or a substance which adsorbs moisture by physical adsorption can be used. Examples thereof are alkali metal oxides, alkaline earth metal oxides (e.g., calcium oxide and barium oxide), sulfates, metal halides, perchlorates, zeolite, and silica gel, One or both of the first space 2013 and the second space 2011 may contain, for example, an inert gas such as a rare gas or a nitrogen gas or may contain an organic resin. Note that these spaces are each in an atmospheric pressure state or a reduced pressure state.

As described above, the light-emitting device described in this embodiment has a double sealing structure, in which one of the first sealant 2005a and the second sealant 2005b is the glass layer having excellent productivity and an excellent sealing property, and the other is the resin layer which is hardly broken by external force or the like, and can contain the desiccant inside, so that a sealing property of suppressing entry of impurities such as moisture and oxygen from the outside can be improved.

Thus, the use of the structure described in this embodiment can provide a light-emitting device in which deterioration of a light-emitting element due to impurities such as moisture and oxygen is suppressed.

Note that the structure described in this embodiment can be used in combination with any of the structures described in the other embodiments and examples as appropriate.
(Embodiment 10)

In this embodiment, a light-emitting device in which the light-emitting element of one embodiment of the present invention is used is described with reference to FIGS. 35A and 35B.

FIGS. 35A and 35B are each an example of a cross-sectional view of a light-emitting device including a plurality of light-emitting elements. A light-emitting device 3000 illustrated in FIG. 35A includes light-emitting elements 3020a, 3020b, and 3020c.

The light-emitting device 3000 includes island-shaped lower electrodes 3003a, 3003b, and 3003c over a substrate 3001. The lower electrodes 3003a, 3003b, and 3003c can function as anodes of the respective light-emitting elements. Reflective electrodes may be provided under the lower electrodes 3003a, 3003b, and 3003c. Transparent conductive layers 3005a, 3005b, and 3005c may be provided over the lower electrodes 3003a, 3003b, and 3003c, respectively. The transparent conductive layers 3005a, 3005b, and 3005c preferably have different thicknesses depending on emission colors of the elements.

The light-emitting device 3000 includes partitions 3007a, 3007b, 3007c, and 3007d. Specifically, the partition 3007a covers one edge portion of the lower electrode 3003a and one edge portion of the transparent conductive layer 3005a; the partition 3007b covers the other edge portion of the lower electrode 3003a and the other edge portion of the transparent conductive layer 3005a and also covers one edge portion of the lower electrode 3003b and one edge portion of the transparent conductive layer 3005b; the partition 3007c covers the other edge portion of the lower electrode 3003b and the other edge portion of the transparent conductive layer 3005b and also covers one edge portion of the lower electrode 3003c and one edge portion of the transparent conductive layer 3005c; the partition 3007d covers the other edge portion of the lower electrode 3003c and the other edge portion of the transparent conductive layer 3005c.

The light-emitting device 3000 includes a hole-injection layer 3009 over the lower electrodes 3003a, 3003b, and 3003c and the partitions 3007a, 3007b, 3007c, and 3007d.

The light-emitting device 3000 includes a hole-transport layer 3011 over the hole-injection layer 3009. The light-emitting device 3000 also includes light-emitting layers 3013a, 3013b, and 3013c over the hole-transport layer 3011. The light-emitting device 3000 also includes an electron-transport layer 3015 over the light-emitting layers 3013a, 3013b, and 3013c.

Further, the light-emitting device 3000 includes an electron-injection layer 3017 over the electron-transport layer 3015. The light-emitting device 3000 also includes an upper electrode 3019 over the electron-injection layer 3017. The upper electrode 3019 can function as cathodes of the light-emitting elements.

Note that although an example in which the lower electrodes 3003a, 3003b, and 3003c function as the anodes of the light-emitting elements and the upper electrode 3019 functions as the cathodes of the light-emitting elements is described with reference to FIG. 35A, the stacking order of the anode and the cathode may be switched. In this case, the stacking order of the electron-injection layer, the electron-transport layer, the hole-transport layer, and the hole-injection layer may be changed as appropriate.

The light-emitting element of one embodiment of the present invention can be applied to the light-emitting layers 3013a, 3013b, and 3013c. The light-emitting element can have low driving voltage, high current efficiency, or a long lifetime; thus, the light-emitting device 3000 can have low power consumption or a long lifetime.

A light-emitting device 3100 illustrated in FIG. 35B includes light-emitting elements 3120a, 3120b, and 3120c. The light-emitting elements 3120a, 3120b, and 3120c are tandem light-emitting elements in which a plurality of light-emitting layers is provided between lower electrodes 3103a, 3103b, and 3103c and an upper electrode 3119.

The light-emitting device 3100 includes the island-shaped lower electrodes 3103a, 3103b, and 3103c over a substrate 3101. The lower electrodes 3103a, 3103b, and 3103c function as anodes of the light-emitting elements. Note that reflective electrodes may be provided under the lower electrodes 3103a, 3103b, and 3103c. Transparent conductive layers 3105a and 3105b may be provided over the lower electrodes 3103a and 3103b. The transparent conductive layers 3105a and 3105b preferably have different thicknesses depending on emission colors of the elements. Although not illustrated, a transparent conductive layer may also be provided over the lower electrode 3103c.

The light-emitting device 3100 includes partitions 3107a, 3107b, 3107c, and 3107d. Specifically, the partition 3107a covers one edge portion of the lower electrode 3103a and one edge portion of the transparent conductive layer 3105a; the partition 3107b covers the other edge portion of the lower electrode 3103a and the other edge portion of the transparent conductive layer 3105a and also covers one edge portion of the lower electrode 3103b and one edge portion of the transparent conductive layer 3105b; the partition 3107c covers the other edge portion of the lower electrode 3103b and the other edge portion of the transparent conductive layer 3105b and also covers one edge portion of the lower electrode 3103c and one edge portion of the transparent conductive layer 3105c; the partition 3107d covers the other edge portion of the lower electrode 3103c and the other edge portion of the transparent conductive layer 3105c.

The light-emitting device 3100 includes a hole-injection and hole-transport layer 3110 over the lower electrodes 3103a, 3103b, and 3103c and the partitions 3107a, 3107b, 3107c, and 3107d.

The light-emitting device 3100 includes a first light-emitting layer 3112 over the hole-injection and hole-transport layer 3110. The light-emitting device 3100 also includes a second light-emitting layer 3116 over the first light-emitting layer 3112 with a charge generation layer 3114 therebetween.

Further, the light-emitting device 3100 includes an electron-transport and electron-injection layer 3118 over the second light-emitting layer 3116. In addition, the light-emitting device 3100 includes the upper electrode 3119 over the electron-transport and electron-injection layer 3118. The upper electrode 3119 can function as cathodes of the light-emitting elements.

Note that although an example in which the lower electrodes 3103a, 3103b, and 3103c function as the anodes of the light-emitting elements and the upper electrode 3119 functions as the cathodes of the light-emitting elements is described with reference to FIG. 35B, the stacking order of the anode and the cathode may be switched. In this case, the stacking order of the electron-injection layer, the electron-transport layer, the hole-transport layer, and the hole-injection layer may be changed as appropriate.

The light-emitting element of one embodiment of the present invention can be applied to the first light-emitting layer 3112 and the second light-emitting layer 3116. The light-emitting element can have low driving voltage, high current efficiency, or a long lifetime; thus, the light-emitting device 3100 can have low power consumption or a long lifetime.

Note that the structure described in this embodiment can be combined with any of the structures described in the other embodiments and the examples as appropriate.

(Embodiment 11)

In this embodiment, a lighting device manufactured using the light-emitting element of one embodiment of the present invention is described with reference to FIGS. 36A to 36E.

Figure 36A:
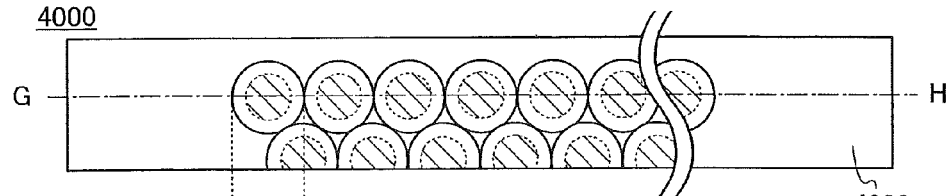
FIGS. 36A to 36E each illustrate a lighting device of one embodiment of the present invention.
Figure 36B:
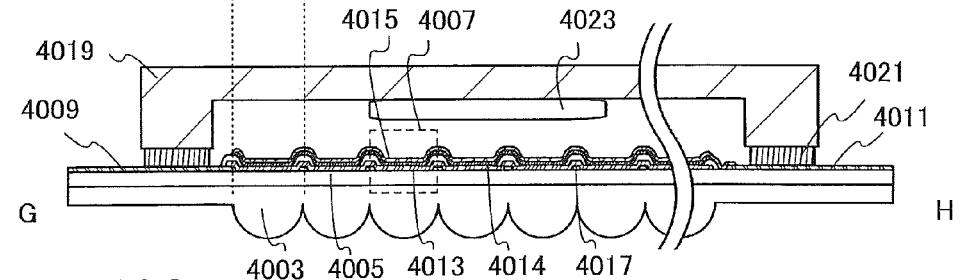
Figure 36C:
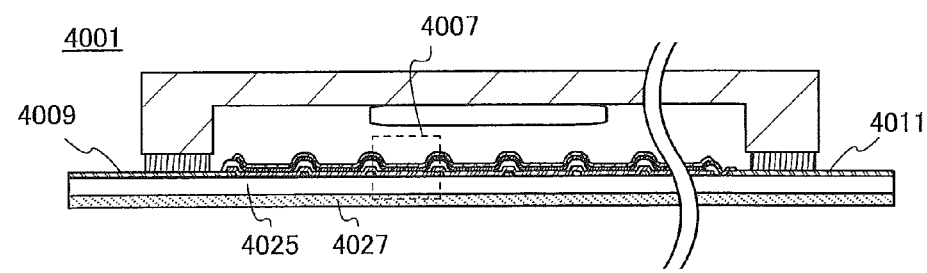

FIGS. 36A to 36E are a plan view and cross-sectional views of lighting devices. FIGS. 36A to 36C are bottom-emission lighting devices in which light is extracted from the substrate side. FIG. 36B is a cross-sectional view taken along the dashed-dotted line G-H in FIG. 36A.

A lighting device 4000 illustrated in FIGS. 36A and 36B includes a light-emitting element 4007 over a substrate 4005. In addition, the lighting device 4000 includes a substrate 4003 with unevenness on the outside of the substrate 4005. The light-emitting element 4007 includes a lower electrode 4013, an EL layer 4014, and an upper electrode 4015.

The lower electrode 4013 is electrically connected to an electrode 4009, and the upper electrode 4015 is electrically connected to an electrode 4011. An auxiliary wiring 4017 electrically connected to the lower electrode 4013 may be provided.

The substrate 4005 and a sealing substrate 4019 are bonded to each other by a sealant 4021. A desiccant 4023 is preferably provided between the sealing substrate 4019 and the light-emitting element 4007.

The substrate 4003 has the unevenness as illustrated in FIG. 36A, whereby the extraction efficiency of light emitted from the light-emitting element 4007 can be increased. Instead of the substrate 4003, a diffusion plate 4027 may be provided on the outside of the substrate 4025 as in a lighting device 4001 illustrated in FIG. 36C.

Figure 36D:
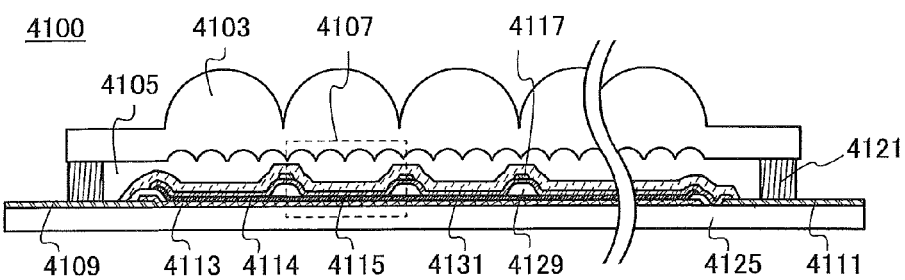
Figure 36E:
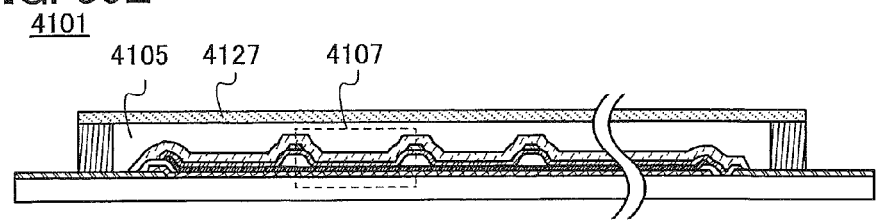

FIGS. 36D and 36E illustrate top-emission lighting devices in which light is extracted from the side opposite to the substrate.

A lighting device 4100 illustrated in FIG. 36D includes a light-emitting element 4107 over a substrate 4125. The light-emitting element 4107 includes a lower electrode 4113, an EL layer 4114, and an upper electrode 4115.

The lower electrode 4113 is electrically connected to an electrode 4109, and the upper electrode 4115 is electrically connected to an electrode 4111. An auxiliary wiring 4117 electrically connected to the upper electrode 4115 may be provided. An insulating layer 4129 may be provided under the auxiliary wiring 4117.

The substrate 4125 and a sealing substrate 4103 with unevenness are bonded to each other by a sealant 4121. A planarization film 4105 and a barrier film 4131 may be provided between the sealing substrate 4103 and the light-emitting element 4107.

The sealing substrate 4103 has the unevenness as illustrated in FIG. 36D, the extraction efficiency of light emitted from the light-emitting element 4107 can be increased. Instead of the sealing substrate 4103, a diffusion plate 4127 may be provided over the light-emitting element 4107 as in a lighting device 4101 illustrated in FIG. 36E.

The light-emitting element of one embodiment of the present invention can be applied to light-emitting layers included in the EL layer 4014 and the EL layer 4114. The light-emitting element can have low driving voltage, high current efficiency, or a long lifetime; thus, the lighting devices 4000, 4001, 4100, and 4101 can have low power consumption or a long lifetime.

Note that the structure described in this embodiment can be combined with any of the structures described in the other embodiments and the examples as appropriate.

(Embodiment 12)

In this embodiment, a touch sensor and a module each of which can be combined with the light-emitting device of one embodiment of the present invention are described with reference to FIGS. 37A and 37B, FIG. 38, FIG. 39, and FIG. 40.

Figure 37A:
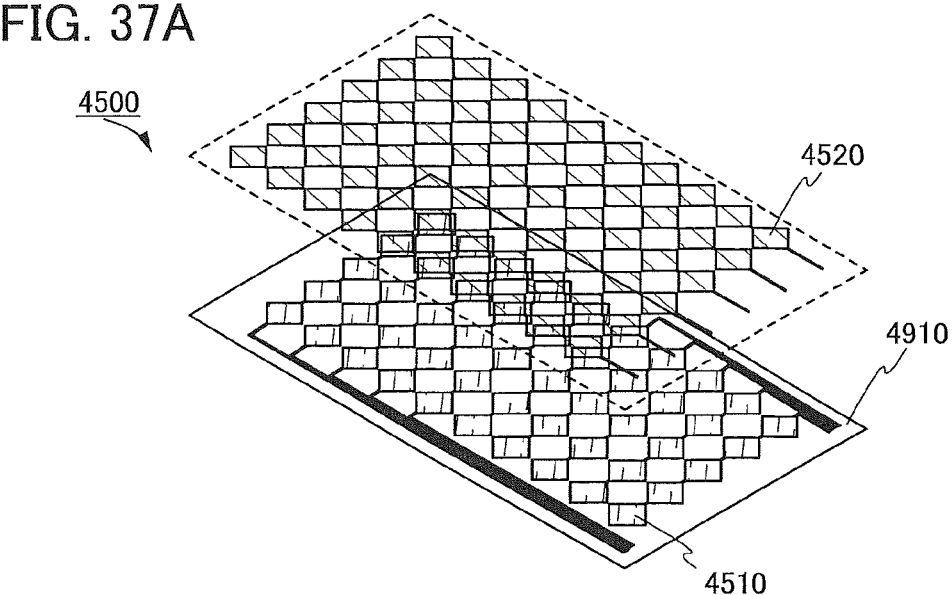
FIGS. 37A and 37B illustrate a touch sensor.
Figure 37B:
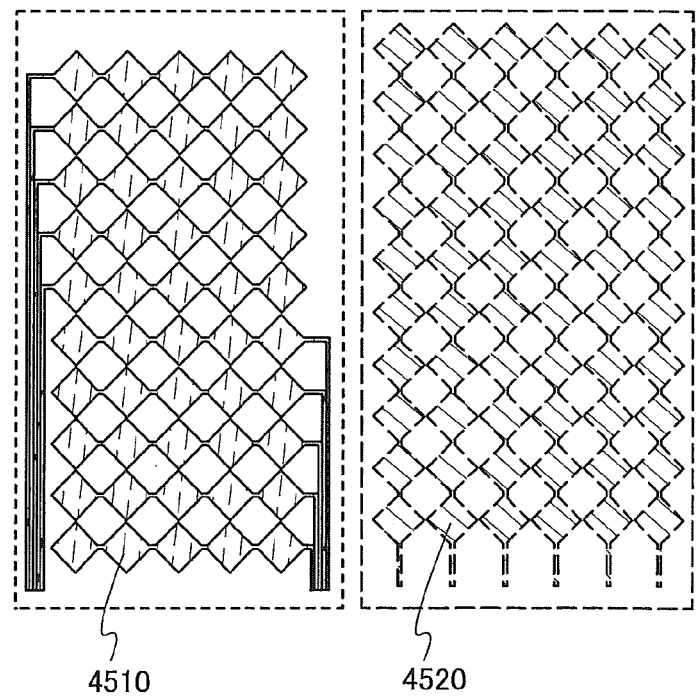

FIG. 37A is an exploded perspective view illustrating a structural example of a touch sensor 4500. FIG. 37B is a plan view illustrating a structural example of the touch sensor 4500.

The touch sensor 4500 illustrated in FIGS. 37A and 37B includes, over a substrate 4910, a plurality of conductive layers 4510 arranged in the X-axis direction and a plurality of conductive layers 4520 arranged in the Y-axis direction which intersect with the X-axis direction. In FIGS. 37A and 37B illustrating the touch sensor 4500, a plane over which the plurality of conductive layers 4510 are formed and a plane over which the plurality of conductive layers 4520 are formed are separately illustrated.

Figure 38:
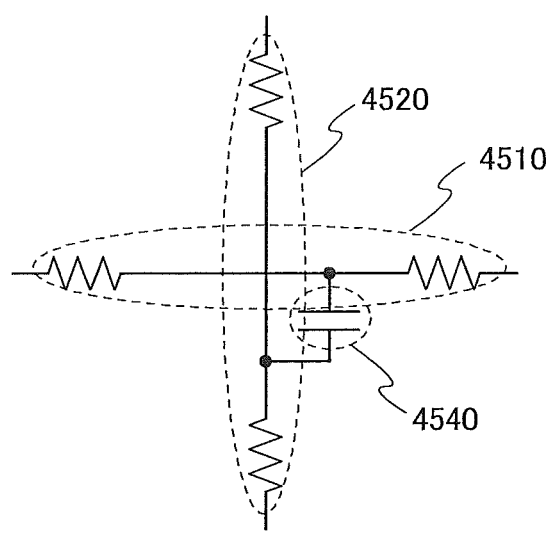
FIG. 38 is a circuit diagram of a touch sensor.

FIG. 38 is an equivalent circuit diagram illustrating the portion where the conductive layer 4510 and the conductive layer 4520 intersect with each other. A capacitor 4540 is formed in the portion where the conductive layer 4510 and the conductive layer 4520 intersect with each other as in FIG. 38.

The conductive layer 4510 and the conductive layer 4520 each have a structure in which a plurality of quadrangular conductive films is connected to one another. The plurality of conductive layers 4510 and the plurality of conductive layers 4520 are provided so that the quadrangular conductive films of the conductive layer 4510 and the quadrangular conductive films of the conductive layer 4520 do not overlap with each other. In the portion where the conductive layer 4510 intersects with the conductive layer 4520, an insulating film is provided between the conductive layer 4510 and the conductive layer 4520 so that the conductive layer 4510 and the conductive layer 4520 are not in contact with each other.

Figure 39:
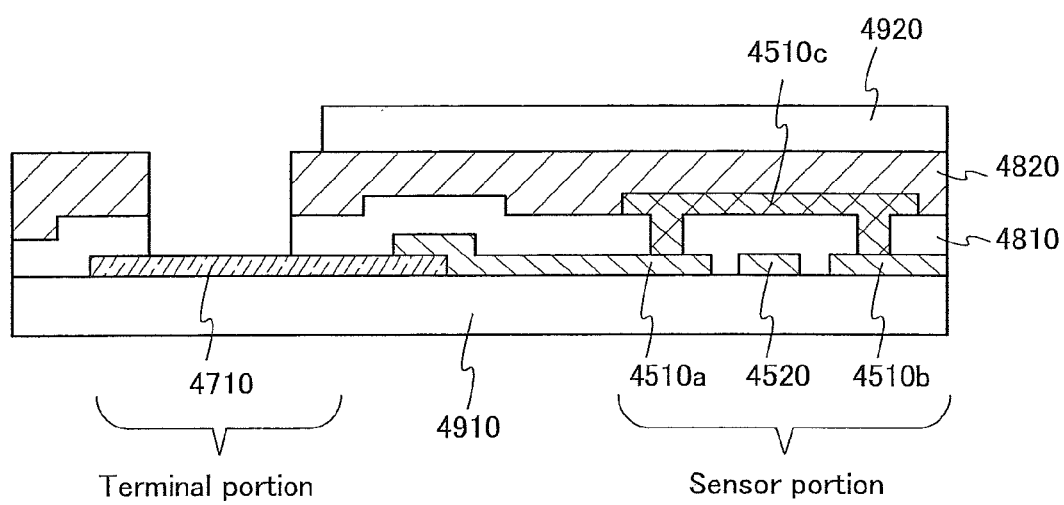
FIG. 39 is a cross-sectional view of a touch sensor.

FIG. 39 is a cross-sectional view illustrating an example of a connection between the conductive layers 4510a, 4510b, and 4510c and the conductive layer 4520 in the touch sensor 4500 illustrated in FIGS. 37A and 37B and is an example of a cross-sectional view illustrating a portion where the conductive layer 4510 (conductive layers 4510a, 4510b, and 4510c ) intersect with the conductive layer 4520.

As illustrated in FIG. 39, the conductive layer 4510 includes the conductive layer 4510a and the conductive layer 4510b in the first layer and the conductive layer 4510c in the second layer over an insulating layer 4810. The conductive layer 4510a and the conductive layer 4510b are connected to each other by the conductive layer 4510c. The conductive layer 4520 is formed using the conductive layer in the first layer. The insulating layer 4820 is formed so as to cover the conductive layers 4510 and 4520 and part of a conductive layer 4710. As the insulating layers 4810 and 4820, for example, a silicon oxynitride film may be formed. Note that a base film formed of an insulating film may be formed between a substrate 4910 and the conductive layers 4710, 4510a, 4510b, and 4520. As the base film, for example, a silicon oxynitride film can be formed.

The conductive layers 4510a, 4510b, and 4510c and the conductive layer 4520 are formed using a conductive material having a property of transmitting visible light. Examples of the conductive material having a property of transmitting visible light include indium tin oxide containing silicon oxide, indium tin oxide, zinc oxide, indium zinc oxide, and zinc oxide to which gallium is added.

The conductive layer 4510a is connected to the conductive layer 4710. A terminal for connection to an FPC is formed using the conductive layer 4710. The conductive layer 4520 is connected to the conductive layer 4710 like the conductive layer 4510a. The conductive layer 4710 can be formed of, for example, a tungsten film.

The insulating layer 4820 is formed so as to cover the conductive layers 4510 and 4520 and the conductive layer 4710. An opening is formed in the insulating layers 4810 and 4820 over the conductive layer 4710 so that the conductive layer 4710 is electrically connected to an FPC. A substrate 4920 is attached to and over the insulating layer 4820 using an adhesive, an adhesive film, or the like. The substrate 4910 side is bonded to a color filter substrate of a display panel with an adhesive or an adhesive film, so that a touch panel is completed.

Next, a module for which the light-emitting device of one embodiment of the present invention can be used is described with reference to FIG. 40.

Figure 40:
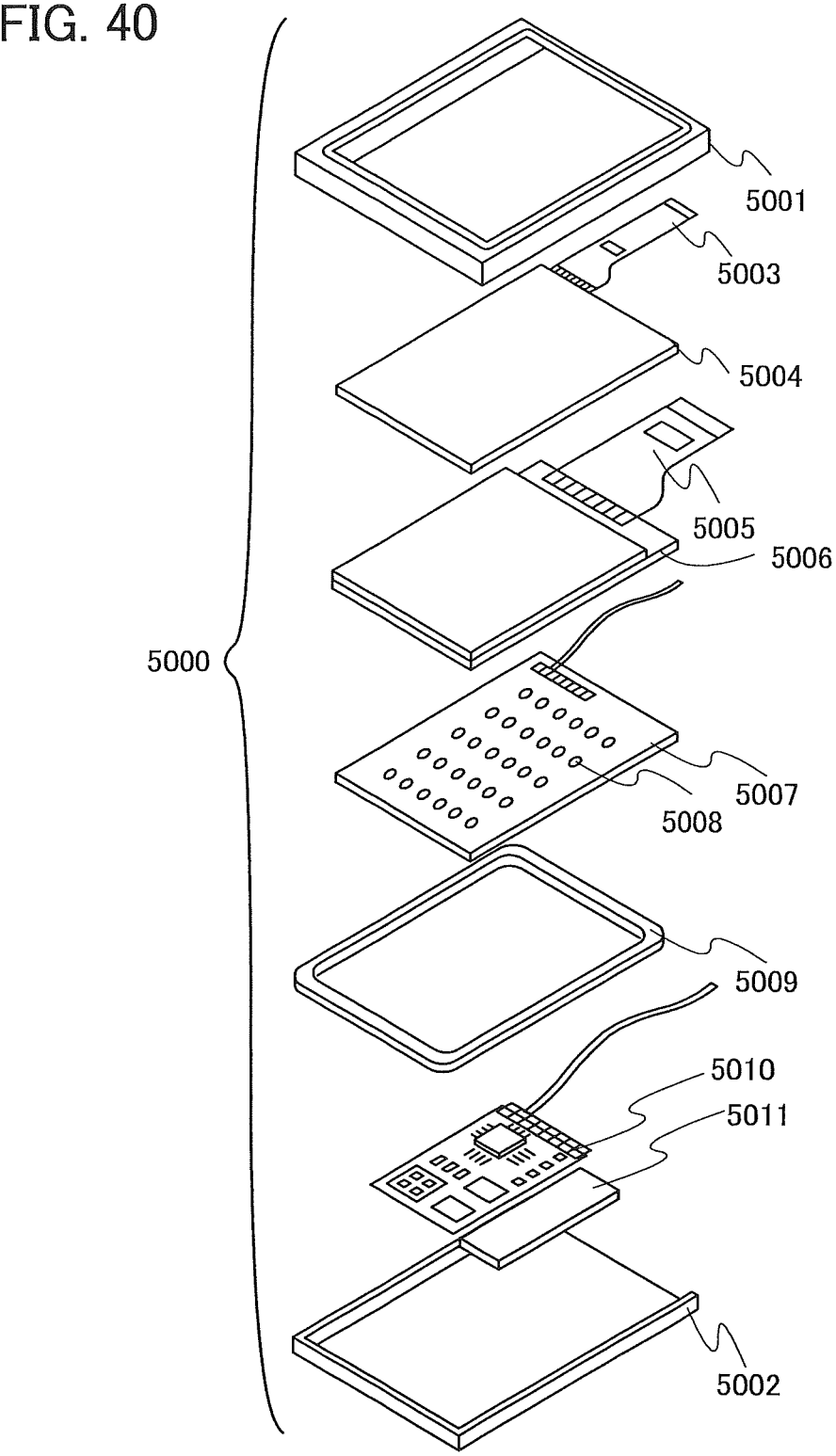
FIG. 40 illustrates a module using a light-emitting device of one embodiment of the present invention.

In a module 5000 illustrated in FIG. 40, a touch panel 5004 connected to an FPC 5003, a display panel 5006 connected to an FPC 5005, a backlight unit 5007, a frame 5009, a printed board 5010, and a battery 5011 are provided between an upper cover 5001 and a lower cover 5002. The light-emitting device shown in Embodiment 9 can be used as the backlight unit 5007, for example.

The shapes and sizes of the upper cover 5001 and the lower cover 5002 can be changed as appropriate in accordance with the sizes of the touch panel 5004 and the display panel 5006.

The touch panel 5004 can be a resistive touch panel or a capacitive touch panel and can be formed to overlap with the display panel 5006. It is also possible to provide a touch panel function for a counter substrate (sealing substrate) of the display panel 5006. A photosensor may be provided in each pixel of the display panel 5006 so that an optical touch panel is obtained.

The backlight unit 5007 includes light sources 5008. Note that although a structure in which the light sources 5008 are provided over the backlight unit 5007 is illustrated in FIG. 40, one embodiment of the present invention is not limited to this structure. For example, a structure in which a light source 5008 is provided at an end portion of the backlight unit 5007 and a light diffusion plate is further provided may be employed.

The frame 5009 has a function of protecting the display panel 5006 and functions as an electromagnetic shield for blocking electromagnetic waves generated by the operation of the printed board 5010. The frame 5009 may function as a radiator plate.

The printed board 5010 has a power supply circuit and a signal processing circuit for outputting a video signal and a clock signal. As a power source for supplying electric power to the power supply circuit, an external commercial power source or a power source using a battery 5011 separately provided may be used. The battery 5011 can be omitted when a commercial power source is used.

The module 5000 can be additionally provided with a member such as a polarizing plate, a retardation plate, or a prism sheet.

Note that the structure described in this embodiment can be combined with any of the structures described in the other embodiments and the examples as appropriate.

(Embodiment 13)

In this embodiment, a structure of a light-emitting element of one embodiment of the present invention is described with reference to FIGS. 41A and 41B.

Figure 41A:
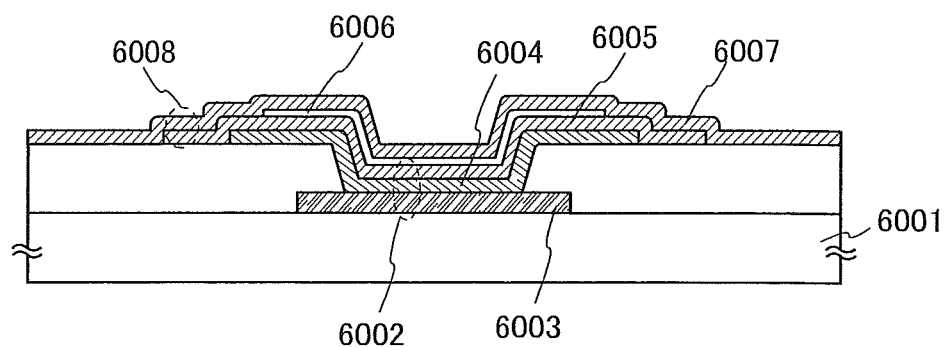
FIGS. 41A and 41B each illustrate a light-emitting element of one embodiment of the present invention.

A light-emitting element 6002 illustrated in FIG. 41A is formed over a substrate 6001. The light-emitting element 6002 includes a first electrode 6003, an EL layer 6004, and a second electrode 6005. In a light-emitting device illustrated in FIG. 41A, a buffer layer 6006 is formed over the second electrode 6005, and a third electrode 6007 is formed over the buffer layer 6006. The buffer layer 6006 can prevent a decrease in light-extraction efficiency due to surface plasmon generated on a surface of the second electrode 6005.

Note that the second electrode 6005 and the third electrode 6007 are electrically connected to each other in a contact portion 6008. The position of the contact portion 6008 is not limited to the position in the drawing, and may be formed in a light-emitting region.

The first electrode 6003 may be an anode and the second electrode may be a cathode, or alternatively, the first electrode 6003 may be a cathode and the second electrode may be an anode. At least one of the electrodes has a light-transmitting property, and both of the electrodes may be formed with light-transmitting materials. In the case where the first electrode 6003 has a function of transmitting light from the EL layer 6004, a transparent conductive film such as ITO can be used for the first electrode 6003. In the case where the first electrode 6003 blocks light from the EL layer 6004, a conductive film formed by stacking a plurality of layers (e.g., ITO and silver) can be used for the first electrode 6003.

In a structure in which light from the EL layer 6004 is extracted on the first electrode 6003 side, the thickness of the second electrode 6005 is preferably smaller than the thickness of the third electrode 6007. In a structure in which the light is extracted on the opposite side, the thickness of the second electrode 6005 is preferably larger than the thickness of the third electrode 6007. However, the thickness is not limited thereto.

For the buffer layer 6006, an organic film (e.g., Alq), an inorganic insulating material (e.g., a silicon nitride film), or the like can be used.

Figure 41B:
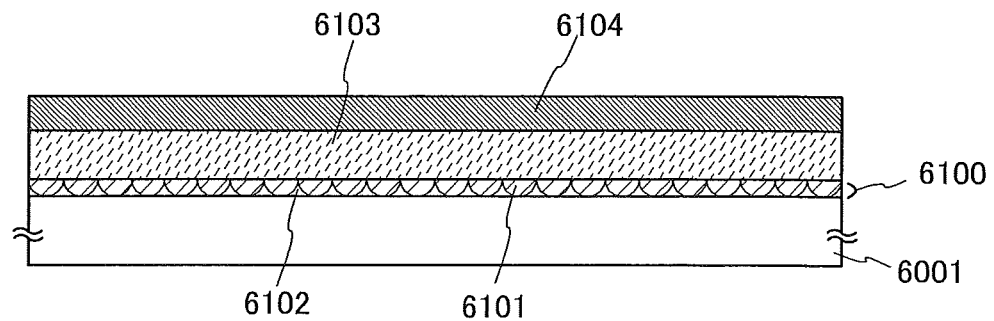

The light-extraction efficiency may be improved by employing a structure illustrated in FIG. 41B as a structure including the light-emitting element of one embodiment of the present invention.

In the structure illustrated in FIG. 41B, a light scattering layer 6100 including a light scatterer 6101 and an air layer 6102 is formed in contact with the substrate 6001; a high refractive index layer 6103 formed with an organic resin is formed in contact with the light scattering layer 6100; and an element layer 6104 including a light-emitting element and the like is formed in contact with the high refractive index layer 6103.

For the light scatterer 6101, particles such as ceramic particles can be used. For the high refractive index layer 6103, a high refractive index (e.g., refractive index of 1.7 to 1.8) material such as polyethylene naphthalate (PEN) can be used.

The element layer 6104 includes the light-emitting element described in Embodiments 4 and 5.

EXAMPLE 1

In this example, a synthesis method of 7-[4-(10-phenyl-9-anthryl)phenyl]-7H-dibenzo[c,g]carbazole (abbreviation: cgDBCzPA), which is a dibenzo[c,g]carbazole compound represented by the structural formula (100) and used for a light-emitting element of this embodiment, is described in detail.

<Step 1: Synthesis of 5,6,8,9-Tetrahydro-7H-dibenzo[c,g]carbazole>

In a 100 mL three-neck flask were placed 1.0 g (20 mmol) of hydrazine monohydrate and 14 mL ethanol. To this solution in an ice bath was added dropwise 2.2 mL of a 1.7 M acetic acid with a dropping funnel. To this solution were added dropwise 10 g (68 mmol) of β-tetralone dissolved in 10 mL ethanol with a dropping funnel. This mixture was stirred at 80° C. for 7 hours, whereby a solid was precipitated. After the stirring, this mixture was added to about 50 mL of water and the mixture was stirred at room temperature for 30 minutes. After the stirring, this mixture was suction-filtered to collect a solid. Methanol/water in a 1:1 ratio was added to the collected solid and the mixture was irradiated with ultrasonic waves to wash the solid. After the washing, this mixture was suction-filtered and a solid was collected, giving 3.5 g of a yellow- powder in a yield of 63%. A reaction scheme (a-1) of Step 1 is illustrated below.

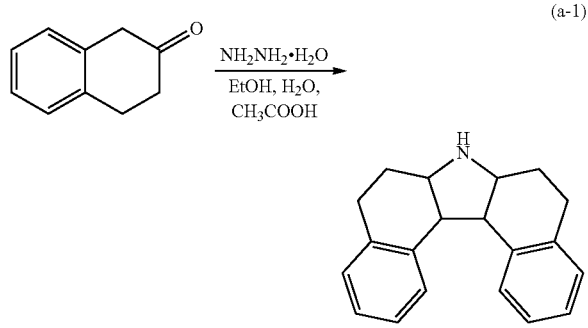

(a-1)

<Step 2: Synthesis of 7H-Dibenzo[c,g]carbazole>

In a 200 mL three-neck flask were placed 6.2 g (25 mmol) of chloranil, 40 mL of xylene, and 3.5 g (12 mmol) of 5,6,8,9-tetrahydro-7H-benzo[c,g]carbazole suspended in 20 mL of xylene. This mixture was refluxed under a nitrogen stream at 150° C. for 4 hours. After reaction, this mixture was cooled to room temperature, precipitating a solid. The precipitated solid was removed by suction filtration and a filtrate was obtained. The obtained filtrate was concentrated, the residue was dissolved in toluene, and the resulting solution was purified by silica gel column chromatography (developing solvent: toluene:hexane=2:1) to give a red solid. Recrystallization of the obtained solid from toluene/hexane gave pale-red needle-like crystals. The obtained crystals were again recrystallized from toluene/hexane, so that 2.5 g of white needle-like crystals were obtained in a yield of 78%. A reaction scheme (b-1) of Step 2 is illustrated below.

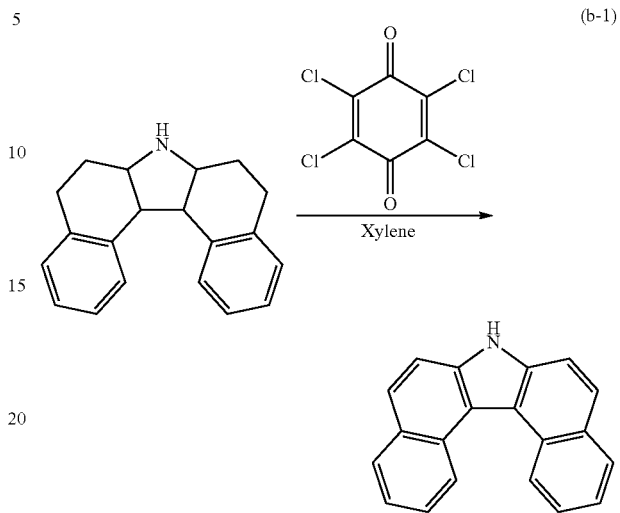

(b-1)

<Step 3: Synthesis of 7-[4-(10-Phenyl-9-anthryl)phenyl]-7H-dibenzo[c,g]carbazole (cgDBCzPA)>

In a 100 mL three-neck flask were placed 2.3 g (5.6 mmol) of 9-(4-bromophenyl)-10-phenylanthracene, 1.5 g (5.6 mol) of 7H-dibenzo[c,g]carbazole, and 1.2 g (12 mmol) of sodium tert-butoxide. After the air in the flask was replaced with nitrogen, to this mixture were added 30 mL of toluene and 2.8 mL of tri(tert-butyl)phosphine (a 10 wt % hexane solution). This mixture was degassed by being stirred while the pressure was reduced. After the degassing, 0.16 g (0.28 mmol) of bis(dibenzylideneacetone)palladium(0) was added to this mixture. This mixture was stirred under a nitrogen stream at 110° C. for 17 hours, so that a solid was precipitated. The precipitated solid was collected by suction filtration. The collected solid was dissolved in about 30 mL of hot toluene, and this solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentration of the filtrate was recrystallized from toluene/hexane to give 2.3 g of a pale yellow powder, which was the object of the synthesis, in a yield of 70%. A reaction scheme (c-1) of Step 3 is illustrated below.

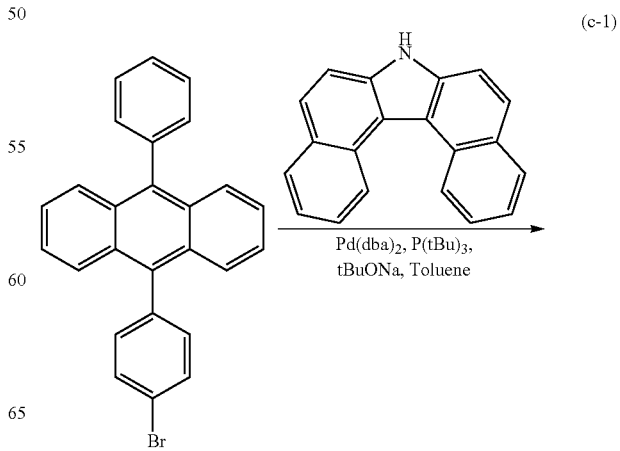

(c-1)

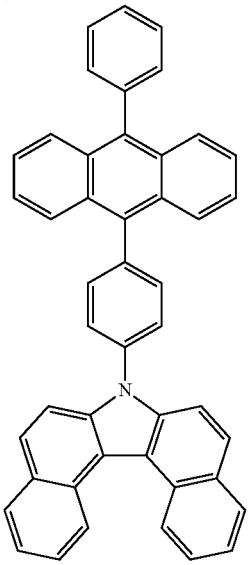

By a train sublimation method, 2.3 g of the obtained pale yellow powdery solid was purified. In the sublimation purification, cgDBCzPA was heated at 310° C. under a pressure of 3.6 Pa with a flow rate of argon gas of 6.0 mL/min. After the sublimation purification, 2.1 g of a pale yellow solid of cgDBCzPA was obtained in a collection rate of 91%.

The obtained substance was measured by $^1$H NMR. The measurement data are shown below.

$^1$H NMR (CDCl$_3$, 300 MHz): δ=7.38-7.67 (m, 11H), 7.72-7.89 (m, 12H), 7.96 (d, J=8.7 Hz, 2H), 8.10 (d, J=7.2 Hz, 2H), 9.31 (d, J$_1$=8.1 Hz, 2H).

Figure 7A:
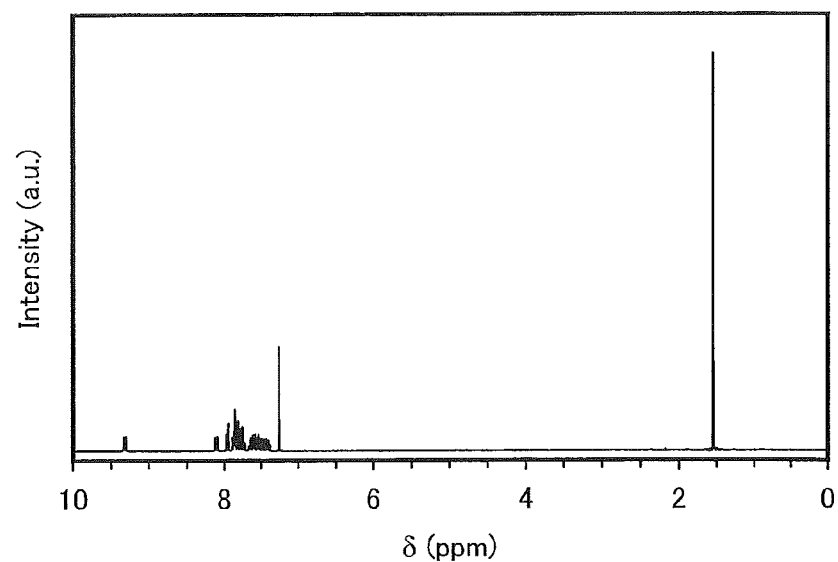
FIGS. 7A and 7B are NMR charts of cgDBCzPA.
Figure 7B:
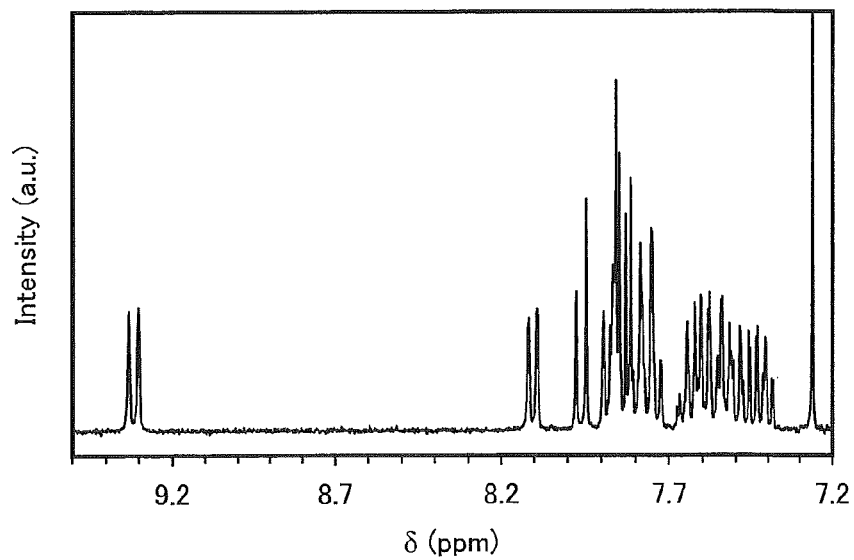

FIGS. 7A and 7B are $^1$H-NMR charts. The measurement results show that cgDBCzPA represented by the above structural formula was obtained.

Figure 8A:
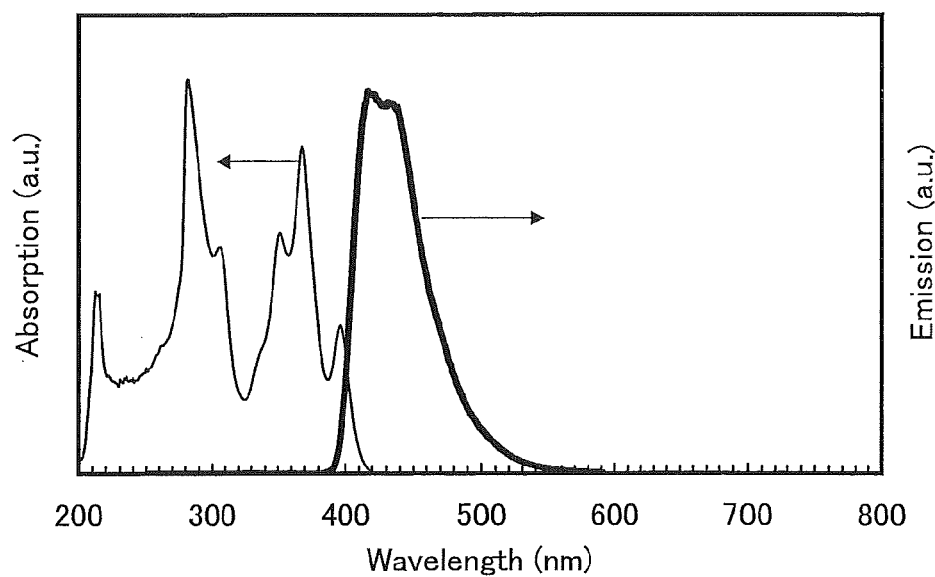
FIGS. 8A and 8B each show an absorption and emission spectra of cgDBCzPA.
Figure 8B:
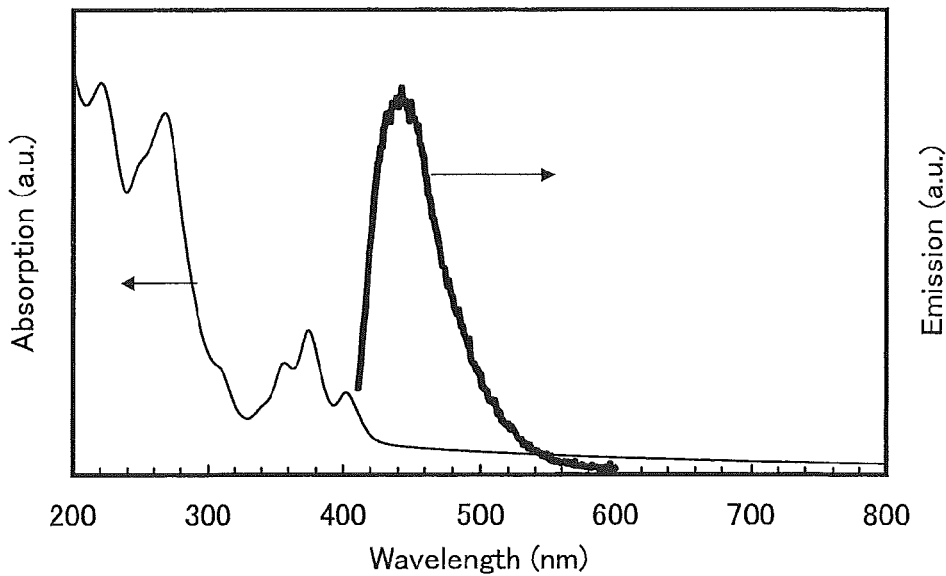

Next, absorption and emission spectra of cgDBCzPA in toluene are shown in FIG. 8A, and absorption and emission spectra of a thin film of cgDBCzPA are shown in FIG. 8B. The absorption spectra were measured using an ultraviolet-visible light spectrophotometer (V550 type manufactured by Japan Spectroscopy Corporation). A toluene solution of cgDBCzPA was put in a quartz cell and then subjected to measurement. The absorption spectrum in solution was obtained by subtracting an absorption spectrum of toluene in the quartz cell from the absorption spectrum of a toluene solution of cgDBCzPA in the quartz cell. As for the absorption spectrum of the thin film, a sample was prepared by evaporation of cgDBCzPA over a quartz substrate, and the absorption spectrum was obtained by subtraction of an absorption spectrum of quartz from the absorption spectrum of this sample. A PL-EL measurement apparatus (Hamamatsu Photonics Corporation) was used for the measurement of emission spectra. The emission spectrum of cgDBCzPA in toluene was measured in a quartz cell, and the emission spectrum of the thin film was measured with a sample prepared by evaporation of cgDBCzPA over a quartz substrate. As shown in FIGS. 8A and 8B, the absorption peak wavelengths of cgDBCzPA in toluene were around 396 nm, around 368 nm, around 351 nm, around 306 nm, and around 252 nm, and the emission peak wavelengths thereof were observed around 417 nm and around 432 nm (an excitation wavelength of 369 nm). It was also found that the absorption peak wavelengths of the thin film were around 402 nm, around 375 nm, around 357 nm, around 343 nm, around 306 nm, around 268 nm, around 252 nm, and around 221 nm and the maximum emission wavelength thereof was around 442 nm (an excitation wavelength of 402 nm).

The ionization potential of a thin film of cgDBCzPA was measured by a photoelectron spectrometer (AC-2, manufactured by Riken Keiki, Co., Ltd.) in the air. The obtained value of the ionization potential was converted to a negative value, revealing that the HOMO level of cgDBCzPA was −5.72 eV. From the data of the absorption spectra of the thin film in FIG. 8B, the absorption edge of cgDBCzPA, which was obtained from a Tauc plot with an assumption of direct transition, was 2.95 eV. Therefore, the optical energy gap of cgDBCzPA in the solid state was estimated to be 2.95 eV; from the values of the HOMO level obtained above and this energy gap, the LUMO level of cgDBCzPA was estimated to be −2.77 eV. It was thus found that cgDBCzPA had a wide energy gap of 2.95 eV in the solid state.

The oxidation characteristics and reduction characteristics of cgDBCzPA were evaluated. These characteristics were examined by cyclic voltammetry (CV) measurements. An electrochemical analyzer (ALS model 600A or 600C, manufactured by BAS Inc.) was used for the measurements.

As for a solution used for the CV measurements, dehydrated N,N-dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration was 100 mmol/L. Further, the object to be measured was dissolved in the solvent such that the concentration was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-5 reference electrode for nonaqueous solvent, manufactured by BAS Inc.) was used as a reference electrode. Note that the measurements were conducted at room temperature (20 to 25° C.). The scan rate was set to 0.1 V/s through the CV measurements.

Figure 9A:
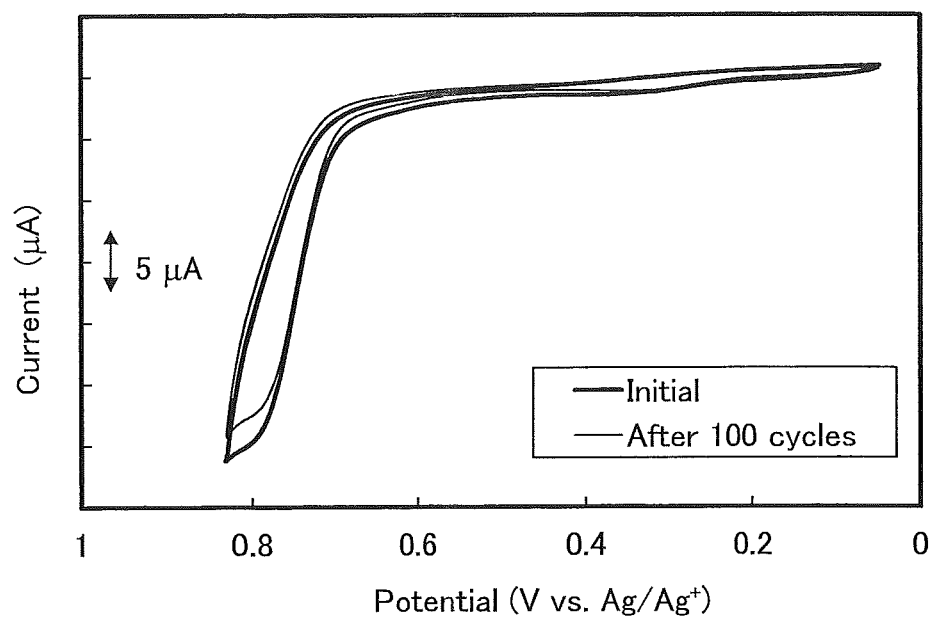
FIGS. 9A and 9B are CV charts of cgDBCzPA.

In the measurements of the oxidation characteristics, one cycle was scanning in which the potential of the working electrode with respect to the reference electrode was changed from 0.05 V to 0.83 V and then changed from 0.83 V to 0.05 V, and 100-cycle measurements were performed. Measurement results are shown in FIG. 9A.

The measurement results revealed that there are no large variations in oxidation peak even after the 100-cycle measurements and that cgDBCzPA shows excellent reversibility against repetition of oxidation and reduction between an oxidized state and a neutral state.

Figure 9B:
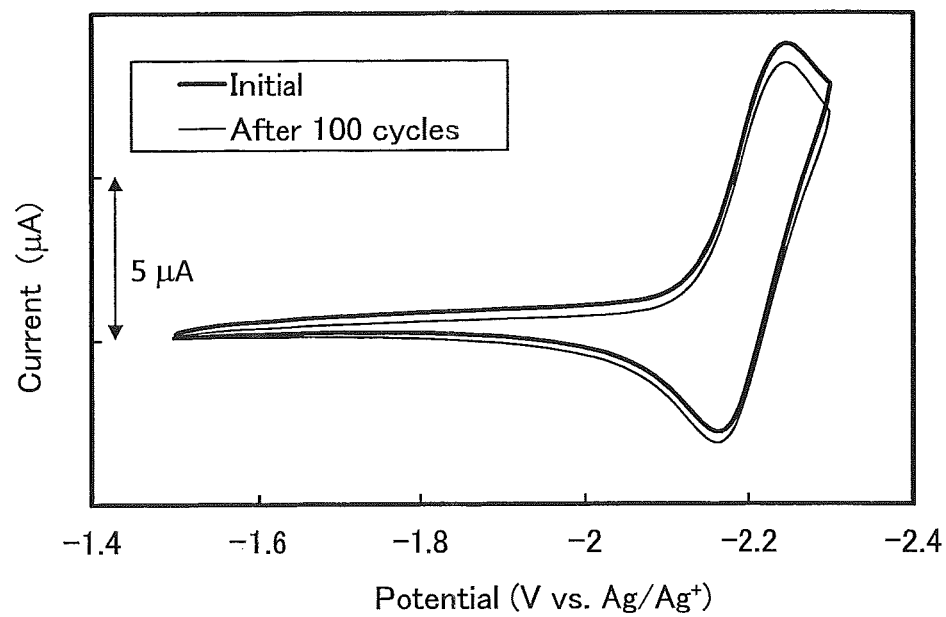

In the measurements of the reduction characteristics, one cycle was scanning in which the potential of the working electrode with respect to the reference electrode was changed from −1.50 V to −2.30 V and then changed from −2.30 V to −1.50 V, and 100-cycle measurements were performed. Measurement results are shown in FIG. 9B.

The measurement results revealed that there are no large variations in reduction peak even after the 100 cycles measurements and that cgDBCzPA shows excellent reversibility against repetition of oxidation and reduction between a reduced state and a neutral state.

The HOMO and LUMO levels of cgDBCzPA were calculated also from the CV measurement results.

First, the potential energy of the reference electrode used in the CV measurement is known to be −4.94 eV with respect to the vacuum level. According to the CV measurements, the oxidation peak potential $E_{pa}$ was 0.81 V and the reduction peak potential $E_{pc}$ was 0.69 V. Therefore, a half-wave potential (an intermediate potential between $E_{pa}$ and $E_{pc}$) was determined to be 0.75 V. This means that cgDBCzPA is oxidized by an electric energy of 0.75 [V vs. Ag/Ag$^+$], and this energy corresponds to the HOMO level. Here, since the potential energy of the reference electrode, which was used in this example, with respect to the vacuum level is −4.94 [eV] as described above, the HOMO level of cgDBCzPA was found to be as follows: −4.94−0.75 =−5.69 [eV]. According to the CV measurements, the oxidation peak potential $E_{pc}$ was −2.25 V and the reduction peak potential $E_{pa}$ was −2.16 V. Therefore, a half-wave potential (an intermediate potential between $E_{pc}$ and $E_{pa}$) was calculated to be −2.21 V. This means that cgDBCzPA is reduced by an electric energy of −2.21 [V vs. Ag/Ag$^+$], and this energy corresponds to the LUMO level. Here, since the potential energy of the reference electrode, which was used in this example, with respect to the vacuum level is −4.94 [eV] as described above, the LUMO level of cgDBCzPA was found to be as follows: −4.94−(−2.21)=−2.74 [eV].

Note that the potential energy of the reference electrode (Ag/Ag$^+$ electrode) with respect to the vacuum level corresponds to the Fermi level of the Ag/Ag$^+$ electrode, and can be calculated from a value obtained by measuring a substance whose potential energy with respect to the vacuum level is known, with the use of the reference electrode (Ag/Ag$^+$ electrode).

The calculation of the potential energy (eV) of the reference electrode (Ag/Ag$^+$ electrode), which was used in this example, with respect to the vacuum level is specifically described. It is known that the oxidation-reduction potential of ferrocene in methanol is +0.610 [V vs. SHE] with respect to the standard hydrogen electrode (Reference: Christian R. Goldsmith et al., *J Am. Chem. Soc., Vol.* 124, No. 1, pp. 83-96, 2002). In contrast, using the reference electrode used in this example, the oxidation-reduction potential of ferrocene in methanol was calculated to be +0.11 V [vs. Ag/Ag$^+$]. Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High molecular EL material*, Kyoritsu Shuppan, pp. 64-67). Therefore, the potential energy of the reference electrode used in this example with respect to the vacuum level can be calculated as follows: −4.44−0.50=−4.94 [eV].

Next, cgDBCzPA obtained in this example was analyzed by liquid chromatography mass spectrometry (LC/MS).

In the analysis by LC/MS, liquid chromatography (LC) separation was carried out with ACQUITY UPLC (manufactured by Waters Corporation) and mass spectrometry (MS) analysis was carried out with Xevo G2 Tof MS (manufactured by Waters Corporation). ACQUITY UPLC BEH C8 (2.1×100 mm, 1.7 μm) was used as a column for the LC separation, and the column temperature was kept at 40° C. Acetonitrile was used for Mobile Phase A and a 0.1% formic acid aqueous solution was used for Mobile Phase B. A sample was prepared in such a manner that cgDBCzPA was dissolved in chloroform at a given concentration and the mixture was diluted with acetonitrile. The injection amount was 5.0 μL.

In the LC separation, a gradient method in which the composition of mobile phases is changed was employed. The ratio of Mobile Phase A to Mobile Phase B was 90:10 for 0 to 1 minute after the start of the measurement. Then, the composition was changed so that the ratio of Mobile Phase A to Mobile Phase B in the 2nd minute was 95:5, and the ratio was kept the same until the 10th minute. The composition was changed linearly.

In the MS analysis, ionization was carried out by an electro-spray ionization (ESI) method. Capillary voltage and sample cone voltage were set to 3.0 kV and 30, respectively. Detection was carried out in a positive mode. The mass range for the measurement was m/z=100 to 1200.

The ionized components were collided with an argon gas in a collision cell to dissociate into product ions. Energy (collision energy) for the collision with argon was 70 eV. The detection results of the product ions by time-of-flight (TOF) MS are shown in FIG. 32.

Figure 32:
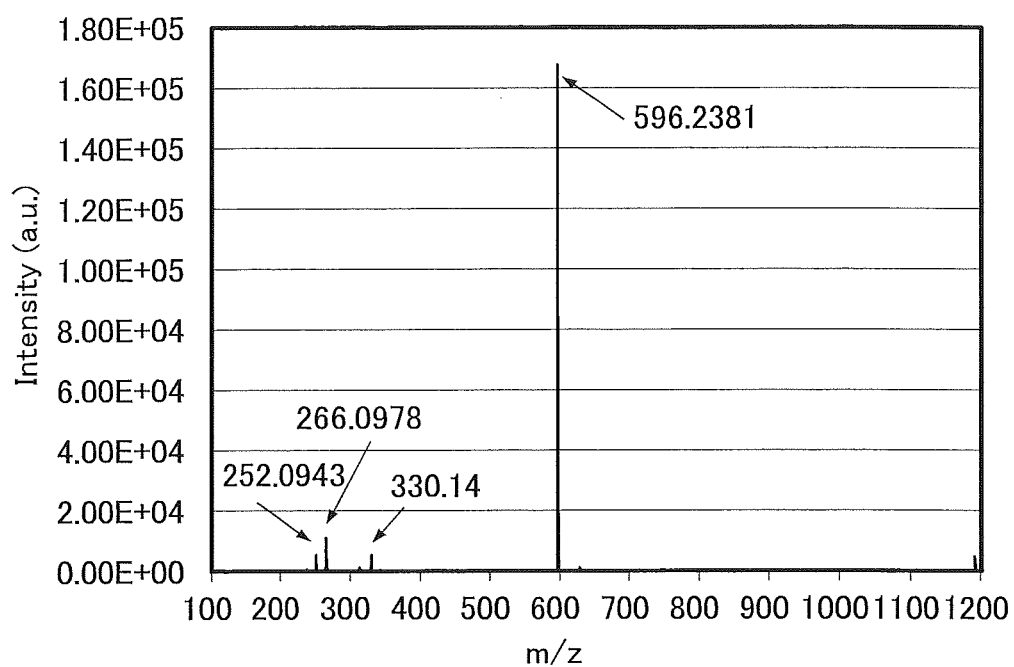
FIG. 32 shows results of LC/MS measurement of a dibenzo[c,g]carbazole compound represented by a structural formula (100).

The results in FIG. 32 show that as for the product ions of cgDBCzPA, which is the dibenzo[c,g]carbazole compound represented by the structural formula (100), are detected mainly around m/z=330.14, m/z=266.10, and m/z=252.09. At this measurement, the intensity of the peak around m/z=596.24 is larger than the intensity of the peak around m/z=266.10, the intensity of the peak around m/z=266.10 is larger than the intensity of the peak around m/z=252.09, and the intensity of the peak around m/z=266.10 is larger than the intensity of the peak around m/z=330.14. Note that the results in FIG. 32 show characteristics derived from cgDBCzPA and therefore can be regarded as important data for identifying cgDBCzPA contained in a mixture.

Note that product ions around m/z=330.14 are probably derived from 9,10-diphenylanthracene which is shown in Formula (a) below and generated due to a cleavage of a bond between the 7-position of a dibenzo[c,g]carbazole and the phenylene group in the compound represented by the structural formula (100). Product ions around m/z=266.10 are probably derived from dibenzo[c,g]carbazole which is shown in Formula (b) below and generated by the aforementioned bond cleavage. Product ions around m/z=252.09 are probably derived from phenyl anthracene which is shown in Formula (c) below and generated due to a cleavage of a bond between the 9-position of anthracene and the phenylene group in the compound represented by the structural formula (100). It should be noted that the product ions represented by Formula (b) are one feature of the dibenzo[c,g]carbazole compound.

(a)

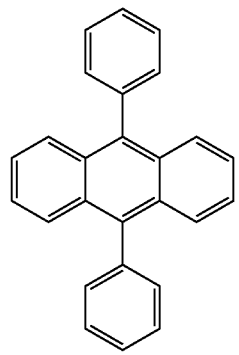

$C_{26}H_{18}$
Exact Mass: 330.14

-continued (b)

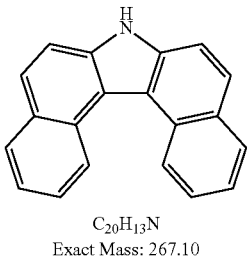

C$_{20}$H$_{13}$N
Exact Mass: 267.10

(c)

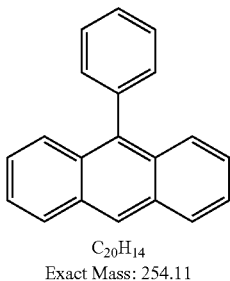

C$_{20}$H$_{14}$
Exact Mass: 254.11

Further, cgDBCzPA obtained in this example was measured with a time-of-flight secondary ion mass spectrometer (TOF-SIMS); FIG. 33 shows the obtained qualitative spectrum of positive ions.

TOF SIMS 5 (produced by ION-TOF GmbH) was used as a measurement apparatus, and Bi$_2^+$ was used as a primary ion source. Note that irradiation with the primary ions was performed in a pulsed manner with a pulse width of 11.3 ns. The irradiation amount was greater than or equal to $8.2 \times 10^{10}$ ions/cm$^2$ and less than or equal to $6.7 \times 10^{11}$ ions/cm$^2$, acceleration voltage was 25 keV, and a current value was 0.2 pA. A powder of cgDBCzPA was the sample used for the measurement.

Figure 33A:
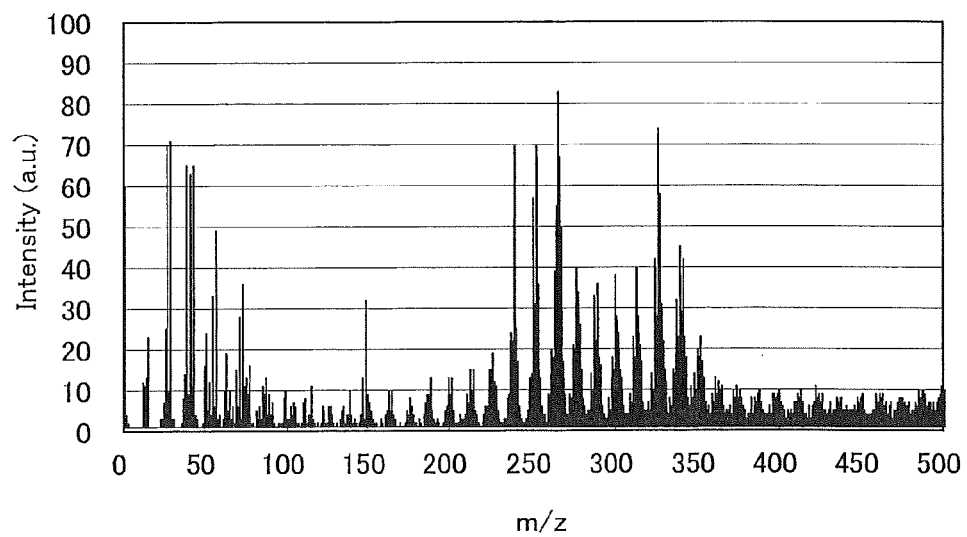
FIGS. 33A and 33B show results of TOF-SIMS (positive ion) measurement of the dibenzo[c,g]carbazole compound represented by the structural formula (100).
Figure 33B:
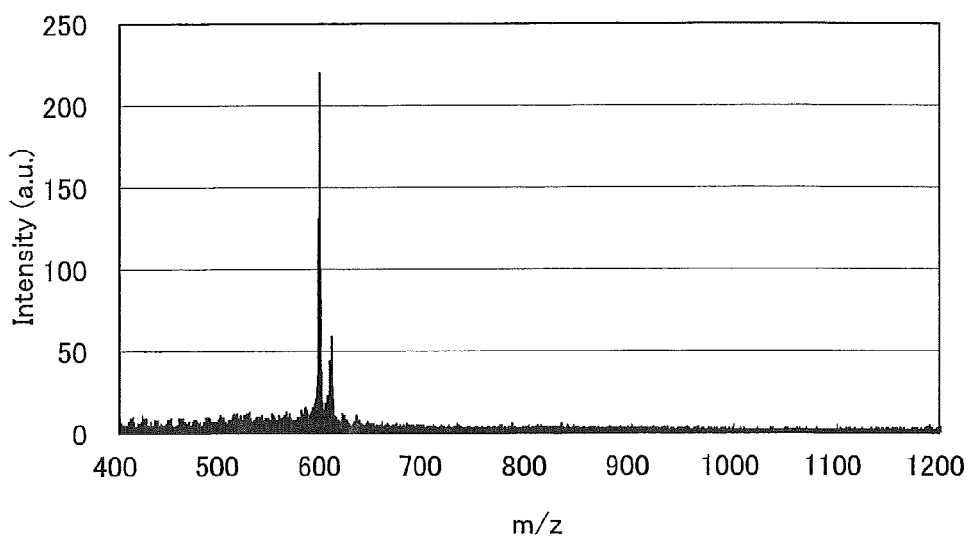

The results of TOF-SIMS analysis (positive ion) in FIGS. 33A and 33B show that cgDBCzPA (exact mass=595.24) mainly gives ions around m/z=596. As product ions, ions derived from 9,10-diphenylanthracene, 9-phenylanthracene, and dibenzo[c,g]carbazole are detected. Since, as shown in FIGS. 33A and 33B, the TOF-SIMS analysis gave the product ions which are similar to those observed in the LC/MS analysis (positive ion) of cgDBCzPA, the result of the measurement by TOF-SIMS can also be regarded as important data for identifying cgDBCzPA contained in the mixture.

EXAMPLE 2

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA), as a host material of a light-emitting layer using an emission substance which emits blue fluorescence and as a material of an electron-transport layer, which is a light-emitting element of one embodiment of the present invention.

Structural formulae and abbreviations of materials used in this example are shown below. The element structure was the same as that illustrated in FIG. 1.

(i)

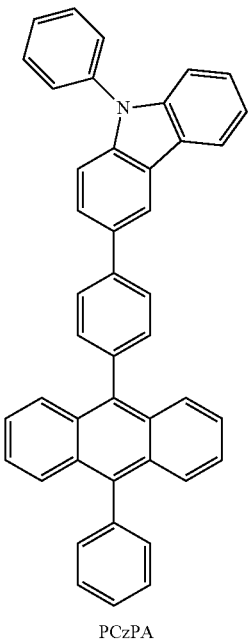

PCzPA (ii)

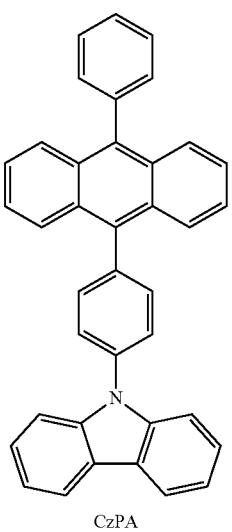

CzPA

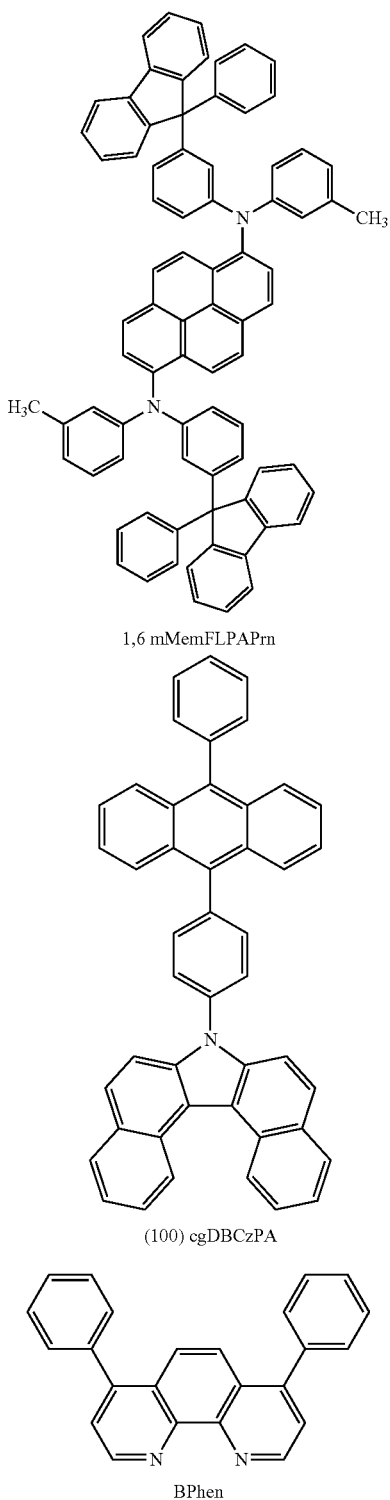

(iii) 1,6 mMemFLPAPrn (100) cgDBCzPA (iv) BPhen

<<Fabrication of Light-Emitting Element 1>>

First, a glass substrate over which indium tin oxide containing silicon (ITSO) had been formed, as the first electrode 101, to a thickness of 110 nm was prepared. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITS( )film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum (VI) oxide were co-evaporated so that the ratio of PCzPA to molybdenum oxide was 2:1 (weight ratio), thereby forming the hole-injection layer 111. The thickness of the hole-injection layer 111 was set to 70 nm. Note that co-evaporation is an evaporation method in which a plurality of different substances is concurrently vaporized from the respective different evaporation sources.

Next, PCzPA was evaporated to a thickness of 30 nm, so that the hole-transport layer 112 was formed.

Further, over the hole-transport layer 112, cgDBCzPA represented by the above structural formula (100) and N,N'-bis(3-methylphenyl)-N,N'-bis[3-(9-phenyl-9H-fluoren-9-yl)phenyl]-pyrene-1,6-dia mine (abbreviation: 1,6mMemFL-PAPrn represented by the above structural formula (iii) were co-evaporated to a thickness of 25 nm so that the ratio of cgDBCzPA to 1,6 mMemFLPAPm was 1:0.03 (weight ratio), thereby forming the light-emitting layer 113.

Next, cgDBCzPA was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 103 which serves as a cathode. Thus, the light-emitting element 1 (Element 1) was completed. Note that in all the evaporation steps in the Examples of the specification, evaporation was performed by a resistance-heating method.

<<Fabrication of Comparison Light-Emitting Element 1>>

The comparison light-emitting element 1 (Reference Element 1) was formed like the light-emitting element 1, except for the light-emitting layer 113 and the electron-transport layer 114. As to the light-emitting layer 113, after the hole-transport layer 112 was formed, 9-[4-(10-phenyl-9-anthryl)phenyl]-9H-carbazole (abbreviation: CzPA) represented by the above structural formula (ii) and 1,6mMem-FLPAPrn were co-evaporated to a thickness of 25 nm so that the ratio of CzPA to 1,6mMemFLPAPrn was 1:0.05 (weight ratio), thereby forming the light-emitting layer 113.

After the light-emitting layer 113 was formed, CzPA was evaporated to a thickness of 10 nm, and then BPhen was evaporated to a thickness of 15 nm, thereby forming the electron-transport layer 114.

The structure other than the light-emitting layer 113 and the electron-transport layer 114 is the same as that of the light-emitting element 1, and repetition of the explanation of the structure is avoided. Refer to the fabrication method of the light-emitting element 1.

Thus, the comparison light-emitting element 1 was completed.

<<Operation Characteristics of Light-Emitting Element 1 and Comparison Light-Emitting Element 1>>

The light-emitting element 1 and the comparison light-emitting element 1 obtained as described above were sealed in a glove box containing a nitrogen atmosphere so as not to be exposed to the air (specifically, a sealing material was applied onto an outer edge of each element and heat treatment was performed at 80° C. for 1 hour at the time of sealing). Then, the operating characteristics of the light-emitting elements were measured. Note that the measurements were carried out at room temperature (in an atmosphere in which the temperature was kept at 25° C.).

Figure 10:
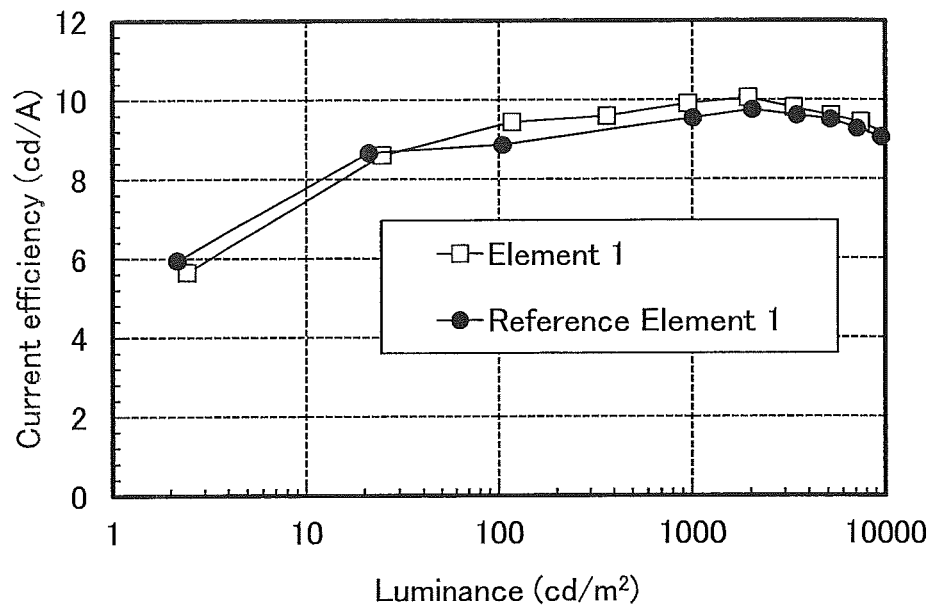
FIG. 10 shows luminance versus current efficiency characteristics of a light-emitting element 1 (Element 1) and a comparison light-emitting element 1 (Reference Element 1).
Figure 11:
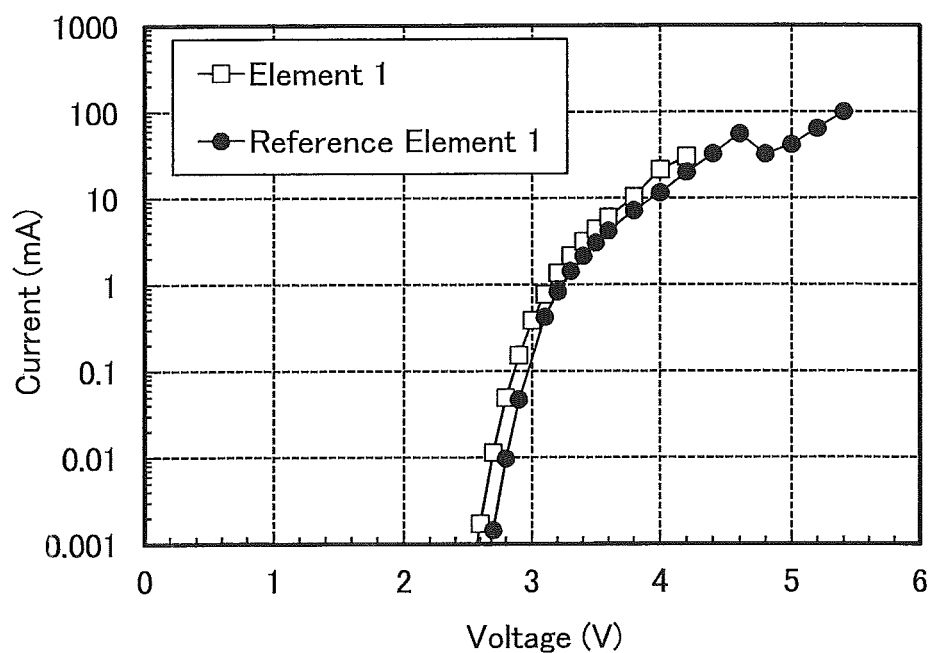
FIG. 11 shows voltage versus current characteristics of the light-emitting element 1 and the comparison light-emitting element 1.
Figure 12:
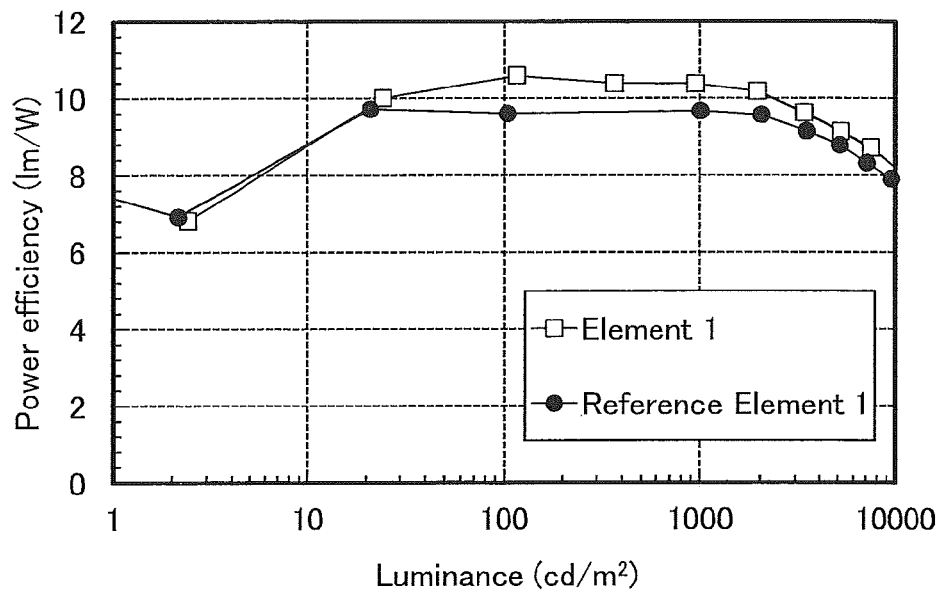
FIG. 12 shows luminance versus power efficiency characteristics of the light-emitting element 1 and the comparison light-emitting element 1.
Figure 13:
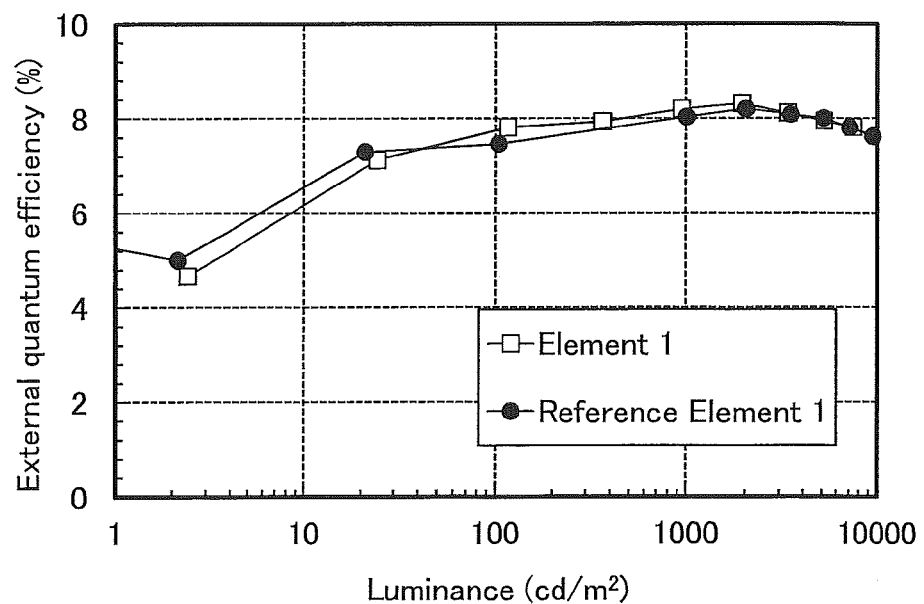
FIG. 13 shows luminance versus external quantum efficiency characteristics of the light-emitting element 1 and the comparison light-emitting element 1.

FIG. 10 shows luminance versus current efficiency characteristics of the light-emitting element 1 and the comparison light-emitting element 1, FIG. 11 shows voltage versus current characteristics, FIG. 12 shows luminance versus power efficiency characteristics, and FIG. 13 shows luminance versus external quantum efficiency characteristics. In FIG. 10, the vertical axis represents current efficiency (cd/A) and the horizontal axis represents luminance (cd/m$^2$). In FIG. 11, the vertical axis represents current (mA) and the horizontal axis represents voltage (V). In FIG. 12, the vertical axis represents power efficiency (lm/W) and the horizontal axis represents luminance (cd/m$^2$). In FIG. 13, the vertical axis represents external quantum efficiency (%) and the horizontal axis represents luminance (cd/m$^2$).

FIG. 10 shows that the light-emitting element 1 using cgDBCzPA that is a dibenzo[c,g]carbazole compound exhibits luminance-current efficiency characteristics similar to or better than those of the comparison light-emitting element 1 using CzPA; accordingly, the light-emitting element 1 has high emission efficiency.

As can be seen from FIG. 11, the voltage versus current characteristics of the light-emitting element 1 are favorable or substantially equal to those of the comparison light-emitting element 1, which indicates that the light-emitting element 1 is a light-emitting element having low driving voltage. This means that cgDBCzPA has an excellent carrier-transport property.

As can be seen from FIG. 12, the light-emitting element 1 exhibits better luminance-power efficiency characteristics than the comparison light-emitting element 1, which indicates that the light-emitting element 1 has low power consumption. Accordingly, the light-emitting element 1 using cgDBCzPA has preferable characteristics such as low driving voltage and high emission efficiency.

As can be seen from FIG. 13, the luminance versus external quantum efficiency characteristics of the light-emitting element 1 are favorable and substantially equal to those of the comparison light-emitting element 1, which indicates that the light-emitting element 1 is a light-emitting element having high emission efficiency.

Figure 14:
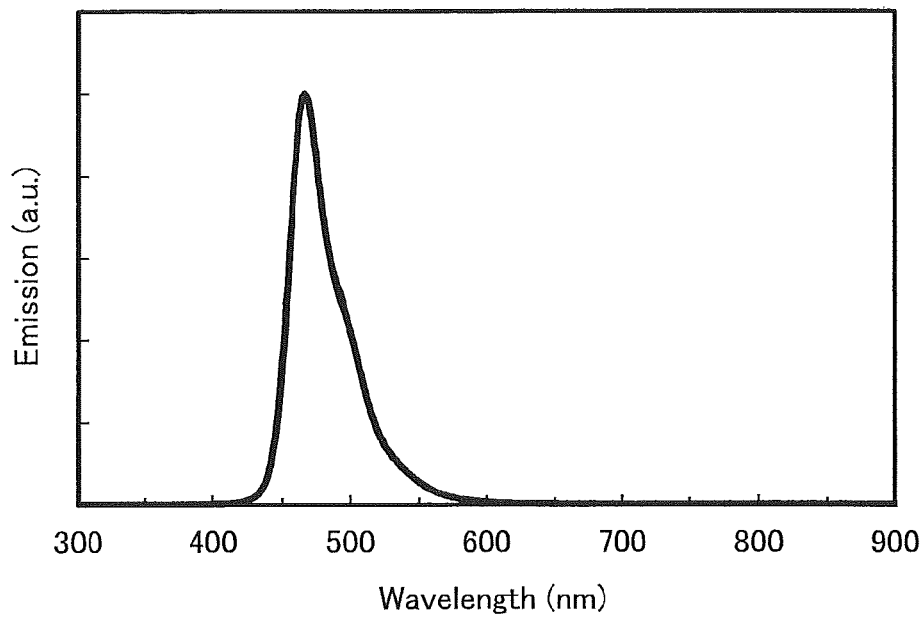
FIG. 14 shows emission spectra of the light-emitting element 1 and the comparison light-emitting element 1.

FIG. 14 shows normalized emission spectra obtained when a current of 0.1 mA was made to flow in the fabricated light-emitting element 1 and the comparison light-emitting element 1. In FIG. 14, the vertical axis represents emission intensity (arbitrary unit) and the horizontal axis represents wavelength (nm). FIG. 14 indicates that both the light-emitting element 1 and the comparison light-emitting element 1 emit blue light derived from 1,6mMemFLPAPrn, which was the emission substance.

Figure 15:
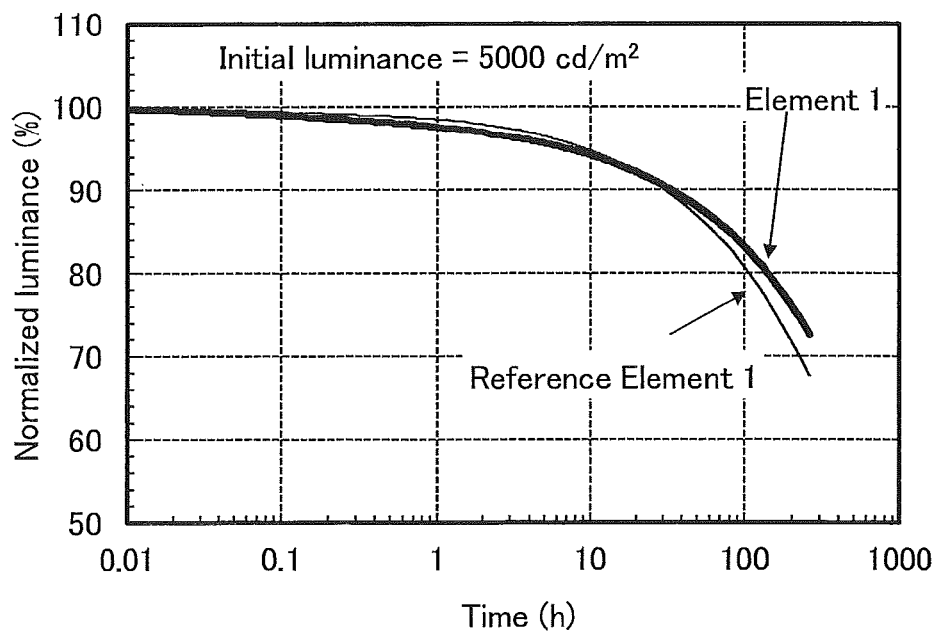
FIG. 15 shows normalized luminance versus time characteristics of the light-emitting element 1 and the comparison light-emitting element 1.

Next, with an initial luminance set to 5000 cd/m$^2$, the light-emitting element 1 and the comparison light-emitting element 1 were driven under a condition where the current density was constant, and changes in luminance relative to driving time were measured. FIG. 15 shows normalized luminance versus time characteristics. FIG. 15 indicates that, although the comparison light-emitting element 1 using CzPA is a light-emitting element having a long lifetime, the light-emitting element 1 using cgDBCzPA is an extremely reliable element having a longer lifetime than the comparison light-emitting element 1.

As compared with CzPA, cgDBCzPA is highly stable to evaporation and can easily provide a light-emitting element having stable qualities.

As described above, with use of cgDBCzPA, a light-emitting element excellent in various characteristics can be provided.

EXAMPLE 3

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA), as a host material of a light-emitting layer using an emission substance which emits blue fluorescence and as a material of an electron-transport layer, which is a light-emitting element of one embodiment of the present invention.

Structural formulae and abbreviations of materials used in this example are shown below. The element structure was the same as that illustrated in FIG. 1A.

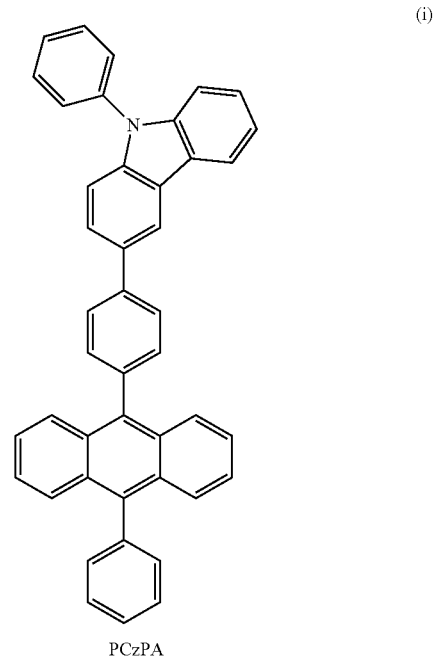

(i)

PCzPA

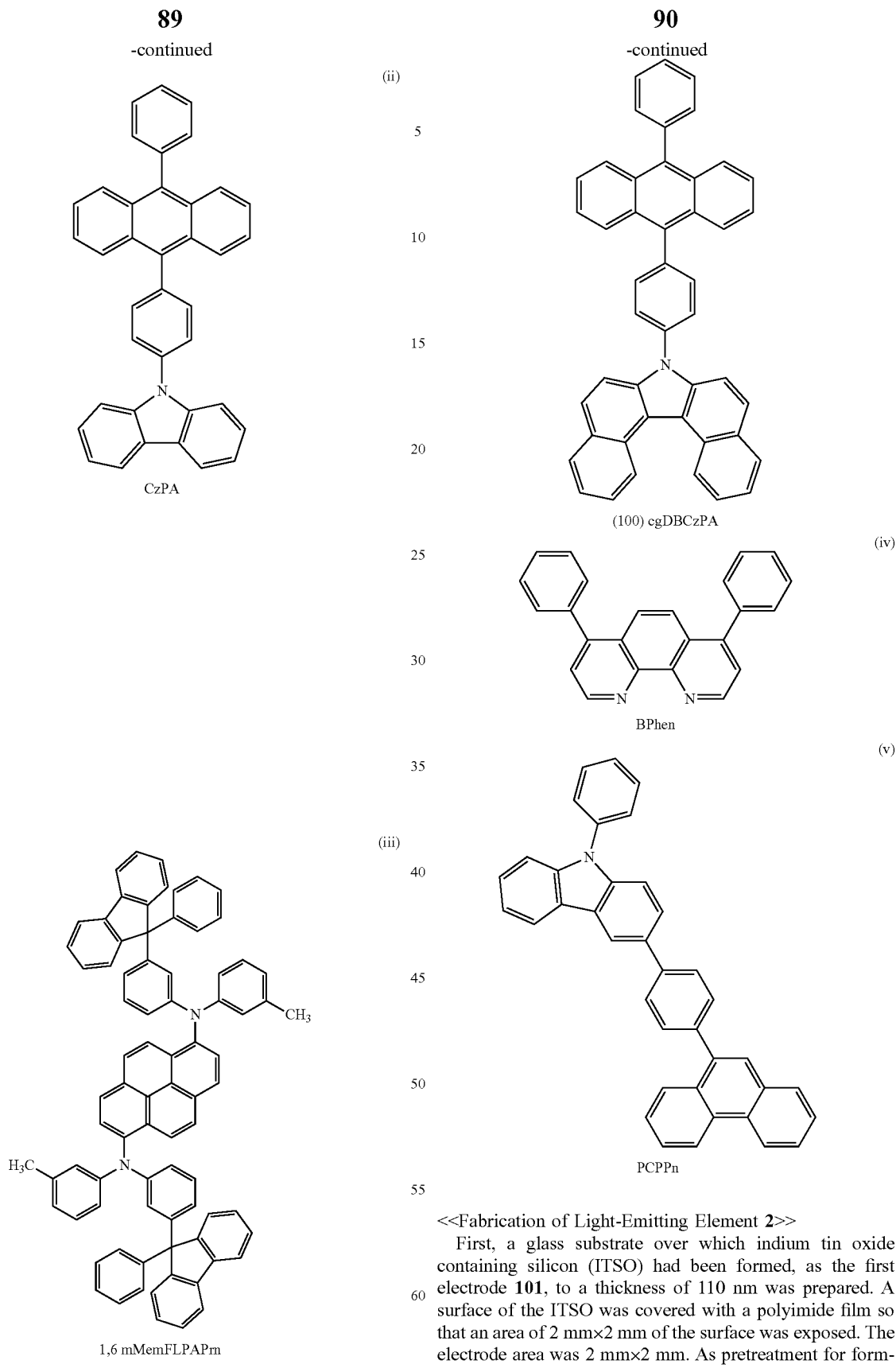

<<Fabrication of Light-Emitting Element 2>>

First, a glass substrate over which indium tin oxide containing silicon (ITSO) had been formed, as the first electrode 101, to a thickness of 110 nm was prepared. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) and molybdenum(VI) oxide were co-evaporated so that the ratio of PCzPA to molybdenum oxide was 2:1 (weight ratio), thereby forming the hole-injection layer 111. The thickness of the hole-injection layer 111 was set to 70 nm.

Next, 3-[4-(9-phenanthryl)-phenyl]-9-phenyl-9H-carbazole (abbreviation: PCPPn) represented by the above structural formula (v) was evaporated to a thickness of 30 nm, so that the hole-transport layer 112 was formed.

Further, over the hole-transport layer 112, cgDBCzPA) and N,N'-bis(3-methylphenye-NN'-bis[3-(9-phenyl-9H-fluoren-9-yl)phenyl]-pyrene-1,6-dia mine (abbreviation:1,6mMemFLPAPrn) represented by the above structural formula (iii) were co-evaporated to a thickness of 25 nm so that the ratio of cgDBCzPA to 1,6mMemFLPAPrn was 1:0.03 (weight ratio), thereby forming the light-emitting layer 113.

Next, cgDBCzPA was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 103 which serves as a cathode. Thus, the light-emitting element 2 was completed.

<<Fabrication of Comparison Light-Emitting Element 2>>

The comparison light-emitting element 2 (Reference Element 2) was formed like the light-emitting element 2, except for the light-emitting layer 113 and the electron-transport layer 114. As to the light-emitting layer 113, after the hole-transport layer 112 was formed, 9-[4-(10-phenyl-9-anthryl)phenyl]-9H-carbazole (abbreviation: CzPA) represented by the above structural formula (ii) and 1,6mMemFLPAPrn were co-evaporated to a thickness of 25 nm so that the ratio of CzPA to 1,6mMemFLPAPrn was 1:0.05 (weight ratio), thereby forming the light-emitting layer 113.

After the light-emitting layer 113 was formed, CzPA was evaporated to a thickness of 10 nm, and then BPhen was evaporated to a thickness of 15 nm, thereby forming the electron-transport layer 114.

The structure other than the light-emitting layer 113 and the electron-transport layer 114 is the same as that of the light-emitting element 2, and repetition of the explanation of the structure is avoided. Refer to the fabrication method of the light-emitting element 2.

Thus, the comparison light-emitting element 2 was completed.

<<Operation Characteristics of Light-Emitting Element 2 and Comparison Light-Emitting Element 2>>

The light-emitting element 2 and the comparison light-emitting element 2 obtained as described above were sealed as performed on the light-emitting element 1, and Then, the operating characteristics of the light-emitting elements were measured. Note that the measurements were carried out at room temperature (in an atmosphere in which the temperature was kept at 25° C.).

Figure 16:
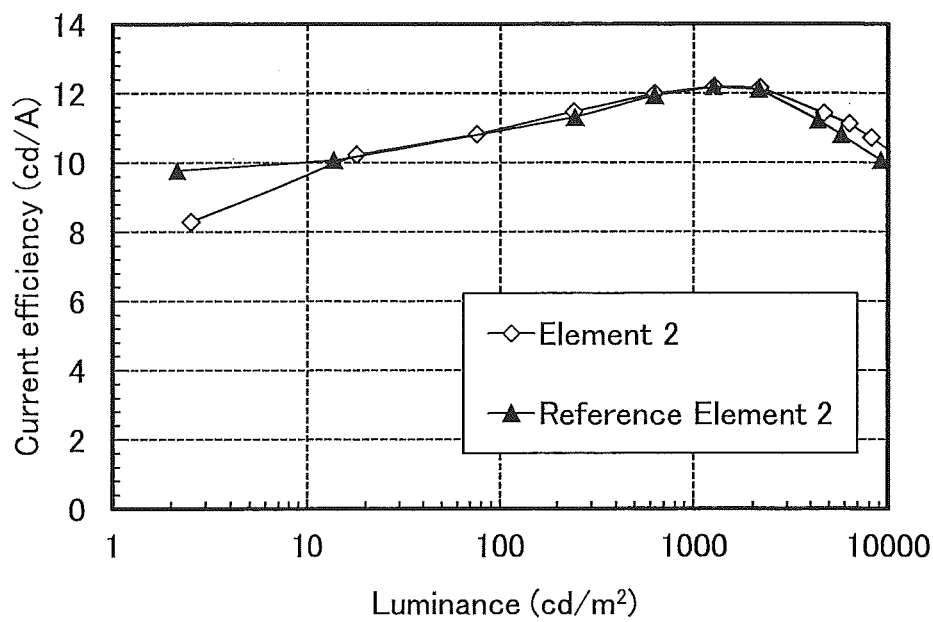
FIG. 16 shows luminance versus current efficiency characteristics of a light-emitting element 2 (Element 2) and a comparison light-emitting element 2 (Reference Element 2).
Figure 17:
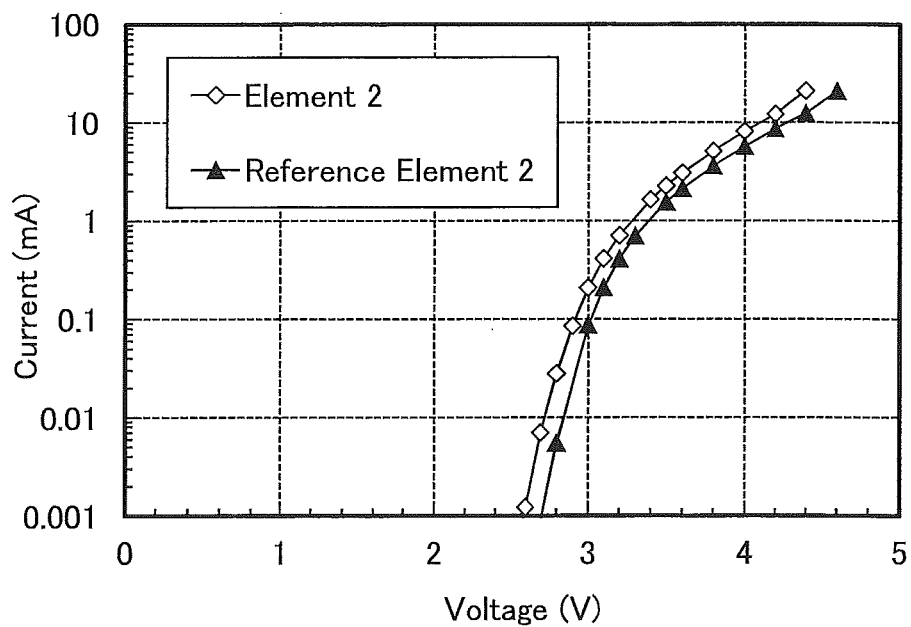
FIG. 17 shows voltage versus current characteristics of the light-emitting element 2 and the comparison light-emitting element 2.
Figure 18:
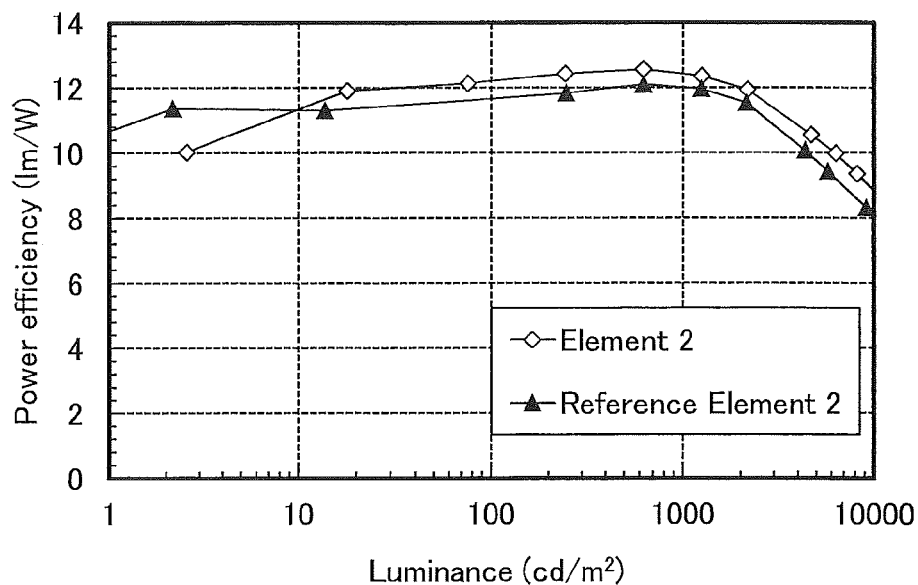
FIG. 18 shows luminance versus power efficiency characteristics of the light-emitting element 2 and the comparison light-emitting element 2.
Figure 19:
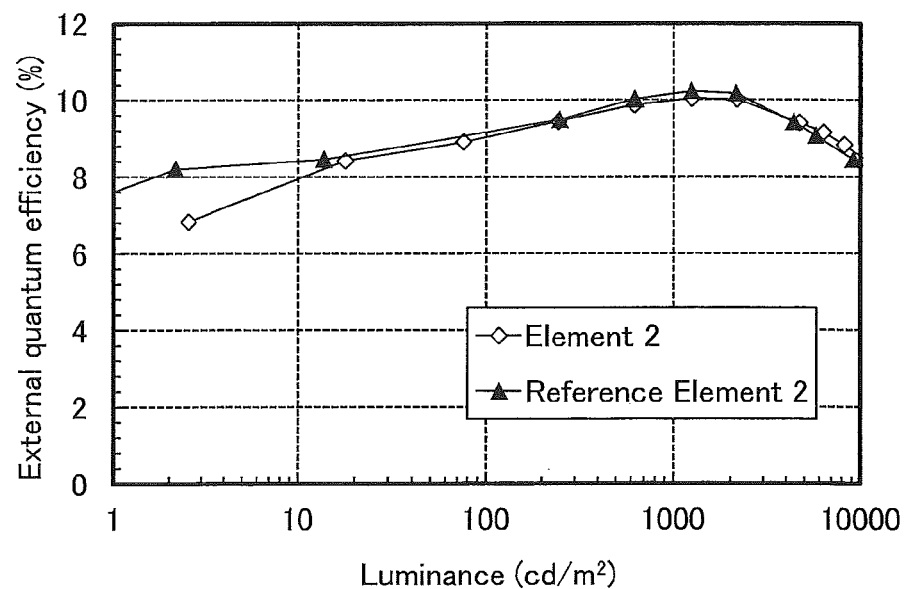
FIG. 19 shows luminance versus external quantum efficiency characteristics of the light-emitting element 2 and the comparison light-emitting element 2.

FIG. 16 shows luminance versus current efficiency characteristics of the light-emitting element 2 and the comparison light-emitting element 2, FIG. 17 shows voltage versus current characteristics, FIG. 18 shows luminance versus power efficiency characteristics, and FIG. 19 shows luminance versus external quantum efficiency characteristics. In FIG. 16, the vertical axis represents current efficiency (cd/A) and the horizontal axis represents luminance ($cd/m^2$). In FIG. 17, the vertical axis represents current (mA) and the horizontal axis represents voltage (V). In FIG. 18, the vertical axis represents power efficiency (lm/W) and the horizontal axis represents luminance ($cd/m^2$). In FIG. 19, the vertical axis represents external quantum efficiency (%) and the horizontal axis represents luminance ($cd/m^2$).

FIG. 16 shows that the light-emitting element 2 using cgDBCzPA that is a dibenzo[c,g]carbazole compound exhibits luminance-current efficiency characteristics similar to those of the comparison light-emitting element 2 using CzPA; accordingly, the light-emitting element 2 has high emission efficiency.

As can be seen from FIG. 17, the voltage versus current characteristics of the light-emitting element 2 are more favorable than those of the comparison light-emitting element 2, which indicates that the light-emitting element 2 is a light-emitting element having low driving voltage. This means that cgDBCzPA has an excellent carrier-transport property.

As can be seen from FIG. 18, the light-emitting element 2 exhibits very favorable luminance-power efficiency characteristics (which is better than the comparison light-emitting element 2), which indicates that the light-emitting element 2 has low power consumption. Accordingly, the light-emitting element 2 using cgDBCzPA has preferable characteristics such as low driving voltage and high emission efficiency.

As can be seen from FIG. 19, the luminance versus external quantum efficiency characteristics of the light-emitting element 2 are favorable and substantially equal to those of the comparison light-emitting element 2, which indicates that the light-emitting element 2 is a light-emitting element having extremely high emission efficiency.

Figure 20:
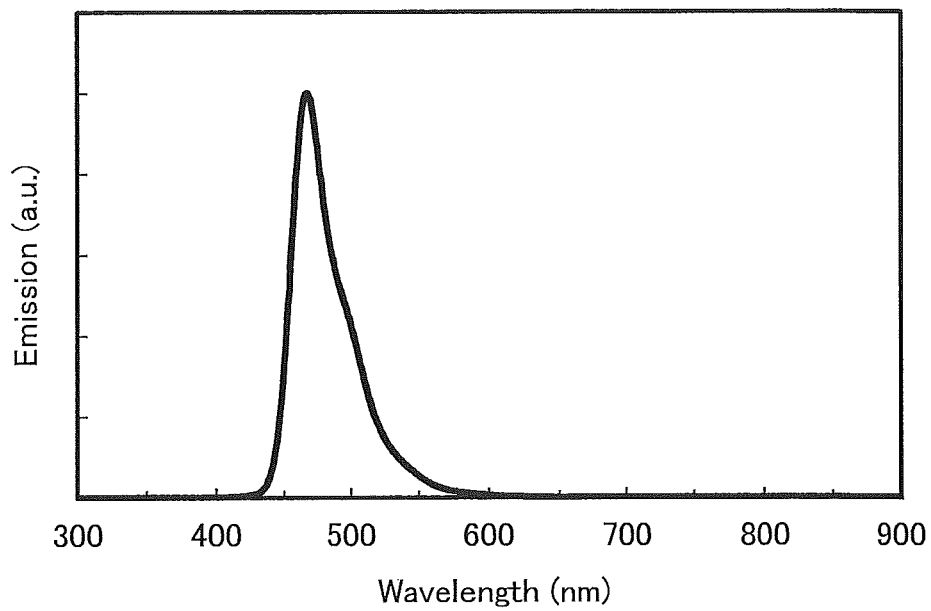
FIG. 20 shows emission spectra of the light-emitting element 2 and the comparison light-emitting element 2.

FIG. 20 shows normalized emission spectra obtained when a current of 0.1 mA was made to flow in the fabricated light-emitting element 2 and the comparison light-emitting element 2. In FIG. 20, the vertical axis represents emission intensity (arbitrary unit) and the horizontal axis represents wavelength (nm). FIG. 20 shows that the spectra of the light-emitting element 2 and the comparison light-emitting element 2 overlaps completely, which indicates that both the light-emitting element 2 and the comparison light-emitting element 2 emit blue light derived from 1,6mMemFLPAPrn, which was the emission substance.

Figure 21:
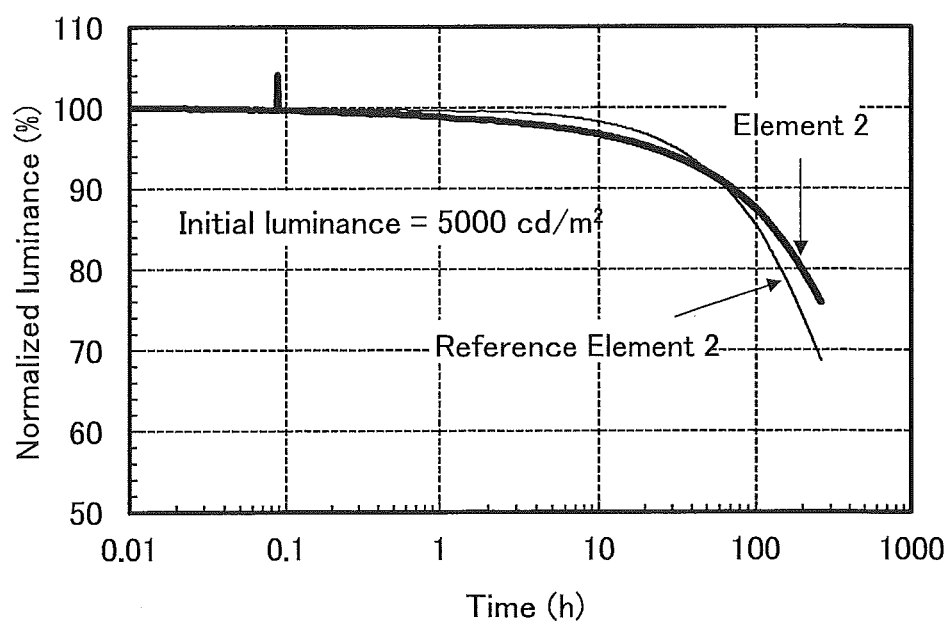
FIG. 21 shows normalized luminance versus time characteristics of the light-emitting element 2 and the comparison light-emitting element 2.

Next, with an initial luminance set to 5000 $cd/m^2$, the light-emitting element 2 and the comparison light-emitting element 2 were driven under a condition where the current density was constant, and changes in luminance relative to driving time were measured. FIG. 21 shows normalized luminance versus time characteristics. FIG. 21 indicates that, although the comparison light-emitting element 2 using CzPA is a light-emitting element having a long lifetime, the light-emitting element 2 using cgDBCzPA is an extremely reliable element having a longer lifetime than the comparison light-emitting element 2.

As compared with CzPA, cgDBCzPA is highly stable to evaporation and can easily provide a light-emitting element having stable qualities.

As described above, with use of cgDBCzPA, a light-emitting element excellent in various characteristics can be provided.

EXAMPLE 4

In this example is described a light-emitting element using a dibenzo[c,g]carbazole compound, 7-[4-(10-phenyl-9-anthryl)phenyl]-7H-dibenzo[c,g]carbazole (abbreviation: cgDBCzPA), as a host material of a light-emitting layer using an emission substance which emits blue fluorescence and as a material of an electron-transport layer, which is a light-emitting element of one embodiment of the present invention.

Structural formulae and abbreviations of materials used in this example are shown below. The element structure was the same as that illustrated in FIG. 1A.

(i)

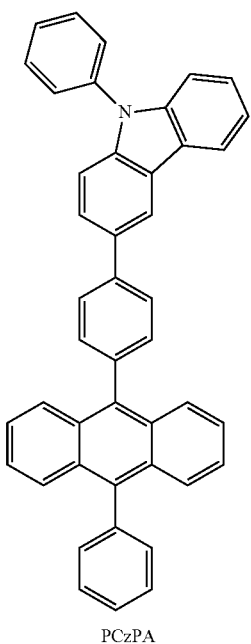

PCzPA (ii)

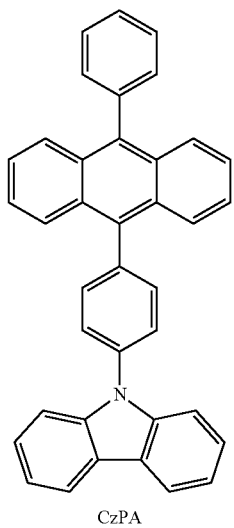

CzPA (iii)

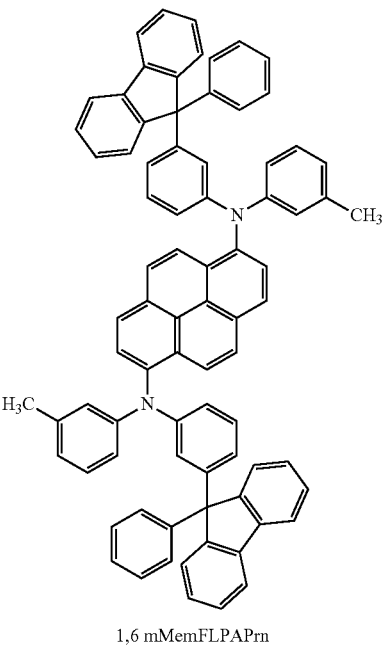

1,6 mMemFLPAPrn

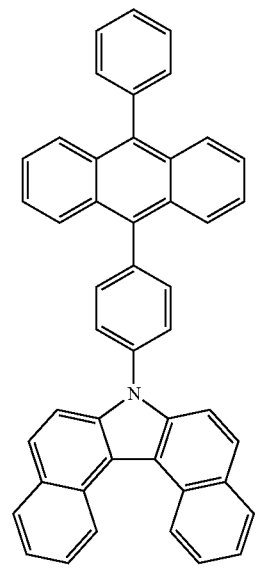

(100) cgDBCzPA (iv)

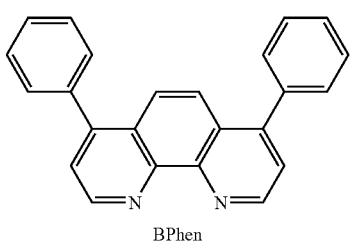

BPhen

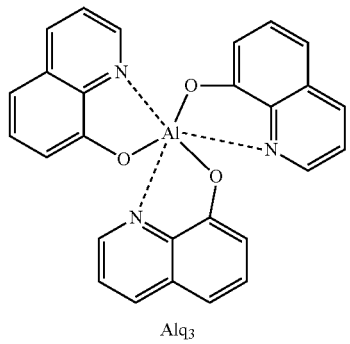

Alq₃

<<Fabrication of Light-Emitting Element 3>>

First, a glass substrate over which indium tin oxide containing silicon (ITSO) had been formed, as the first electrode 101, to a thickness of 110 nm was prepared. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITS( )film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum (VI) oxide were co-evaporated so that the ratio of PCzPA to molybdenum oxide was 2:1 (weight ratio), thereby forming the hole-injection layer 111. The thickness of the hole-injection layer 111 was set to 50 nm.

Next, PCzPA was evaporated to a thickness of 10 nm, so that the hole-transport layer 112 was formed.

Further, over the hole-transport layer 112, cgDBCzPA and N,N'-bis(3-methylphenye-N,N-bis [3-(9-phenyl-9H-fluoren-9-yl)phenyl]-pyrene-1,6-diamine (abbreviation:1,6mMemFLPAPrn) represented by the above structural formula (iii) were co-evaporated to a thickness of 30 nm so that the ratio of cgDBCzPA to 1,6mMemFLPAPrn was 1:0.05 (weight ratio), thereby forming the light-emitting layer 113.

Next, tris(8-quinolinolato)aluminum(III) (abbreviation: Alq) represented by the above structural fotinula (vi) was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 nm over the electron-transport layer 114, thereby forming the electron-injection layer. Lastly, aluminum was formed to a thickness of 200 nm as the second electrode 103 which serves as a cathode. Thus, the light-emitting element 3 (Element 3) was completed.

<<Fabrication of Comparison Light-Emitting Element 3>>

The comparison light-emitting element 3 (Reference Element 2) was formed like the light-emitting element 3, except for the light-emitting layer 113. As to the light-emitting layer 113 in the comparison light-emitting element 3, after the hole-transport layer 112 was formed, 9-[4-(10-phenyl-9-anthryl)phenyl]-9H-carbazole (abbreviation: CzPA) represented by the above structural formula (ii) and 1,6mMemFLPAPrn were co-evaporated to a thickness of 30 nm so that the ratio of CzPA to 1,6mMemFLPAPrn was 1:0.05 (weight ratio), thereby forming the light-emitting layer 113.

The structure other than the light-emitting layer 113 is the same as that of the light-emitting element 3, and repetition of the explanation of the structure is avoided. Refer to the fabrication method of the light-emitting element 3.

Thus, the comparison light-emitting element 3 was completed.

<<Operation Characteristics of Light-Emitting Element 3 and Comparison Light-Emitting Element 3>>

The light-emitting element 3 and the comparison light-emitting element 3 obtained as described above were sealed as performed on the light-emitting element 1, and then, the operating characteristics of the light-emitting elements were measured. Note that the measurements were carried out at room temperature (in an atmosphere in which the temperature was kept at 25° C.).

Figure 22:
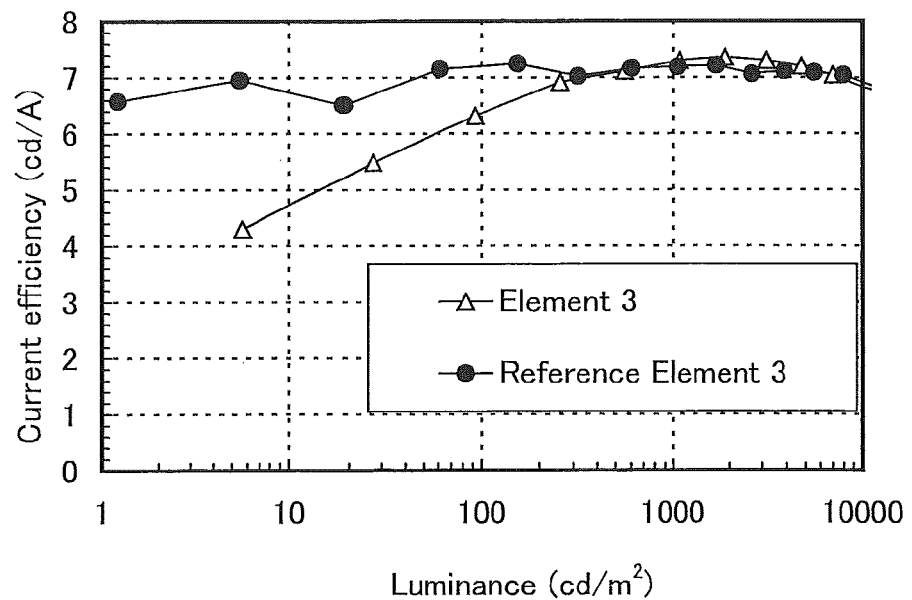
FIG. 22 shows luminance versus current efficiency characteristics of a light-emitting element 3 (Element 3) and a comparison light-emitting element 3 (Reference Element 3).
Figure 23:
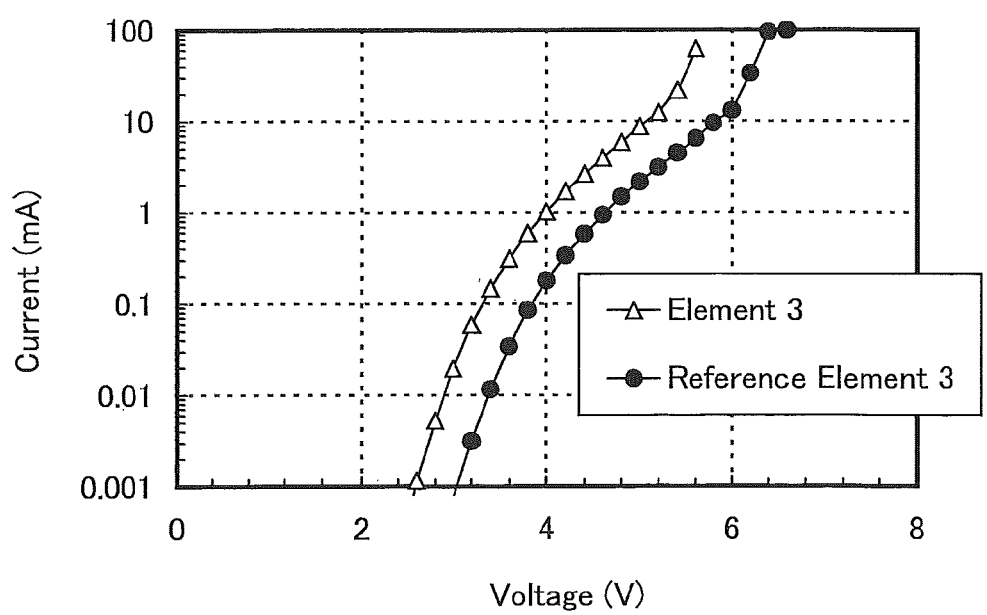
FIG. 23 shows voltage versus current characteristics of the light-emitting element 3 and the comparison light-emitting element 3.

FIG. 22 shows luminance versus current efficiency characteristics of the light-emitting element 3 and the comparison light-emitting element 3, FIG. 23 shows voltage versus current characteristics. In FIG. 22, the vertical axis represents current efficiency (cd/A) and the horizontal axis represents luminance (cd/m²). In FIG. 23, the vertical axis represents current (mA) and the horizontal axis represents voltage (V).

As can be seen from FIG. 22, the luminance versus current efficiency characteristics of the light-emitting element 3 that uses cgDBCzPA, which is a dibenzo[c,g]carbazole compound, are equal to those of the comparison light-emitting element 3 using CzPA like cgDBCzPA in the light-emitting element 3. Accordingly, the light-emitting element 3 has high emission efficiency.

As can be seen from FIG. 23, the voltage versus current characteristics of the light-emitting element 3 are much better than those of the comparison light-emitting element 3, which indicates that the light-emitting element 3 is a light-emitting element having low driving voltage. This means that cgDBCzPA has an excellent carrier-transport property.

Figure 24:
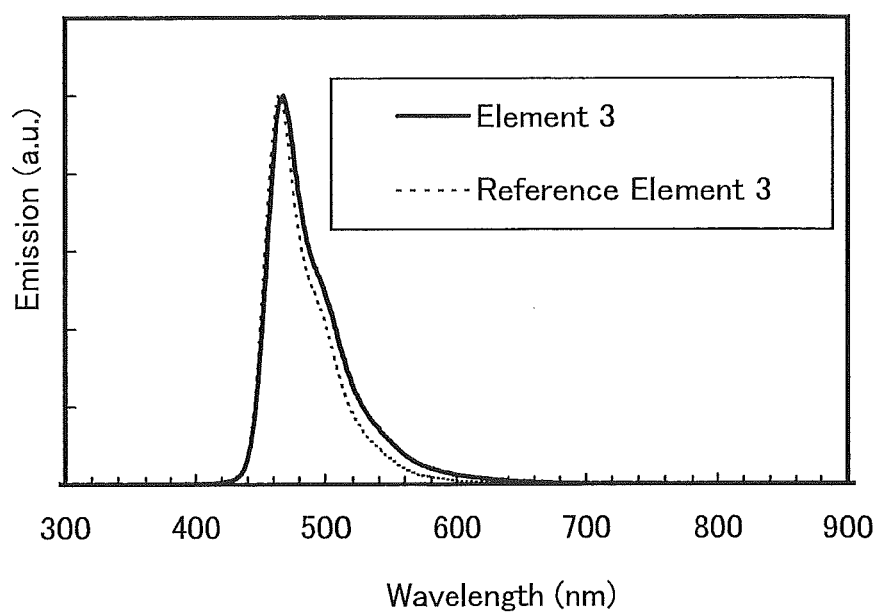
FIG. 24 shows emission spectra of the light-emitting element 3 and the comparison light-emitting element 3.

FIG. 24 shows normalized emission spectra obtained when a current of 0.1 mA was made to flow in the fabricated light-emitting element 3 and the comparison light-emitting element 3. In FIG. 24, the vertical axis represents emission intensity (arbitrary unit) and the horizontal axis represents wavelength (nm). FIG. 24 indicates that the spectra of the light-emitting element 3 and the comparison light-emitting element 3 have no great difference, and the light-emitting element 3 and the comparison light-emitting element 3 emit blue light derived from 1,6mMemFLPAPrn, which was the emission substance.

As compared with CzPA, cgDBCzPA is highly stable to evaporation and can easily provide a light-emitting element having stable qualities.

As described above, with use of cgDBCzPA, a light-emitting element excellent in various characteristics can be provided.

EXAMPLE 5

In this example is described a light-emitting element using a dibenzo[c,g]carbazole compound, 7-[4-(10-phenyl- 9-anthryl)phenyl]-7H-dibenzo[c,g]carbazole (abbreviation: cgDBCzPA), as a host material of a light-emitting layer using an emission substance which emits blue fluorescence and as a material of an electron-transport layer, which is a light-emitting element of one embodiment of the present invention.

Structural formulae and abbreviations of materials used in this example are shown below. The element structure was the same as that illustrated in FIG. 1A.

(i)

PCzPA (100) cgDBCzPA

-continued (iii)

1,6 mMemFLPAPrn (vii)

-continued (viii)

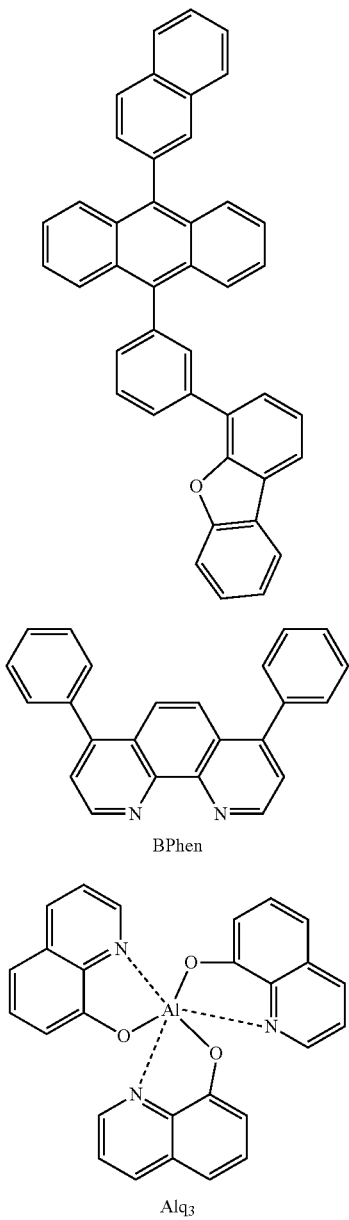

BPhen

Alq₃

<<Fabrication of Light-Emitting Element 4>>

First, a glass substrate over which indium tin oxide containing silicon (ITSO) had been formed, as the first electrode 101, to a thickness of 110 nm was prepared. A surface of the ITSO was covered with a polyimide film so that an area of 2 mm×2 mm of the surface was exposed. The electrode area was 2 mm×2 mm. As pretreatment for forming the light-emitting element over this substrate, UV ozone treatment was performed for 370 seconds after washing of a surface of the substrate with water and baking was performed at 200° C. for 1 hour. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate was fixed to a holder provided in the vacuum evaporation apparatus so that the surface of the substrate over which the ITSO film was formed faced downward.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) represented by the above structural formula (i) and molybdenum (VI) oxide were co-evaporated so that the ratio of PCzPA to molybdenum oxide was 2:1 (weight ratio), thereby forming the hole-injection layer 111. The thickness of the hole-injection layer 111 was set to 50 mn.

Next, PCzPA was evaporated to a thickness of 10 mn, so that the hole-transport layer 112 was formed.

Further, over the hole-transport layer 112, cgDBCzPA) and N,N'-bis(3-methylphenyl)-N,N-bis[3-(9-phenyl-9H-fluoren-9-yl)phenyl]-pyrene-1,6-dia mine (abbreviation:1,6mMemFLPAPrn) represented by the above structural formula (iii) were co-evaporated to a thickness of 25 nm so that the ratio of cgDBCzPA to 1,6mMemFLPAPrn was 1:0.03 (weight ratio), thereby forming the light-emitting layer 113.

Next, tris(8-quinolinolato)aluminum(III) (abbreviation: Alq) represented by the above structural formula (vi) was evaporated to a thickness of 10 nm, and then bathophenanthroline (abbreviation: BPhen) represented by the above structural formula (iv) was evaporated to a thickness of 15 nm, thereby forming the electron-transport layer 114.

Further, lithium fluoride was evaporated to a thickness of 1 mn over the electron-transport layer 114, thereby forming the electron-injection layer. Lastly, aluminum was formed to a thickness of 200 nm as the second electrode 103 which serves as a cathode. Thus, the light-emitting element 4 (Element 4) was completed.

<<Fabrication of Comparison Light-Emitting Element 4-1>>

The comparison light-emitting element 4-1 (Reference Element 4-1) was formed like the light-emitting element 4, except for the light-emitting layer 113. As to the comparison light-emitting element 4-1, after the hole-transport layer 112 was formed, a known anthracene derivative represented by the above structural formula (vii) and 1,6mMemFLPAPrn were co-evaporated to a thickness of 25 nm so that the ratio of the anthracene derivative to 1,6mMemFLPAPrn was 1:0.03 (weight ratio), thereby forming the light-emitting layer 113.

The structure other than the light-emitting layer 113 is the same as that of the light-emitting element 4, and repetition of the explanation of the structure is avoided. Refer to the fabrication method of the light-emitting element 4.

Thus, the comparison light-emitting element 4-1 was completed.

<<Fabrication of Comparison Light-Emitting Element 4-2>>

The comparison light-emitting element 4-2 (Reference Element 4-2) was formed like the light-emitting element 4, except for the light-emitting layer 113. As to the comparison light-emitting element 4-2, after the hole-transport layer 112 was formed, a known anthracene derivative represented by the above structural formula (viii) and 1,6mMemFLPAPrn were co-evaporated to a thickness of 25 nm so that the ratio of the anthracene derivative to 1,6mMemFLPAPrn was 1:0.03 (weight ratio), thereby forming the light-emitting layer 113.

The structure other than the light-emitting layer 113 is the same as that of the light-emitting element 4, and repetition of the explanation of the structure is avoided. Refer to the fabrication method of the light-emitting element 4.

Thus, the comparison light-emitting element 4-2 (Reference Element 4-2) was completed.

<<Operation Characteristics of Light-Emitting Element 4, Comparison Light-Emitting Element 4-1, and Comparison Light-Emitting Element 4-2>>

The light-emitting element 4 and the comparison light-emitting elements 4-1 and 4-2 obtained as described above were sealed as performed on the light-emitting element 1, and then, the operating characteristics of the light-emitting elements were measured. Note that the measurements were carried out at room temperature (in an atmosphere in which the temperature was kept at 25° C.).

Figure 25:
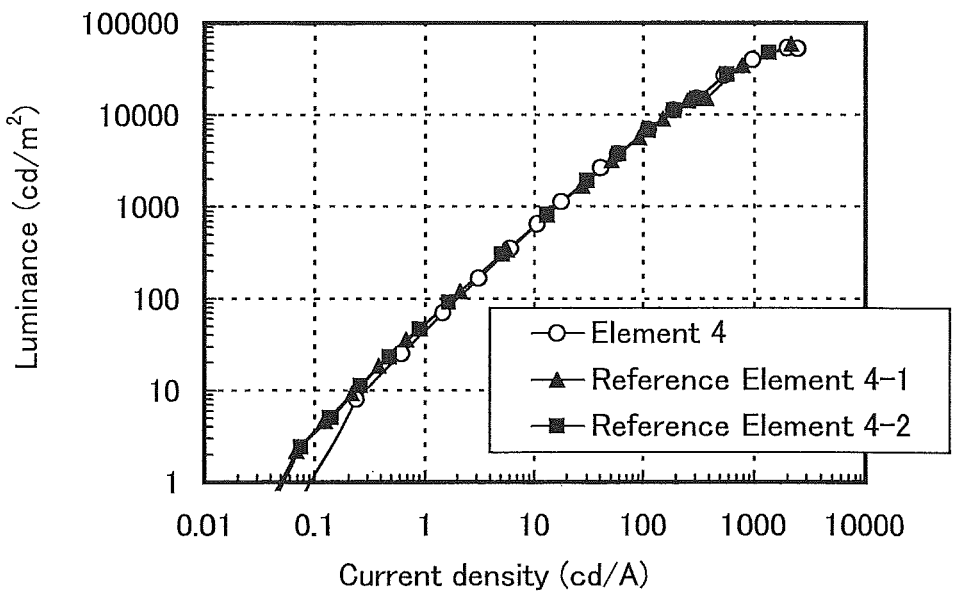
FIG. 25 shows current density versus luminance characteristics of a light-emitting element 4 (Element 4) and comparison light-emitting elements 4-1 (Reference Element 4-1) and 4-2 (Reference Element 4-2).
Figure 26:
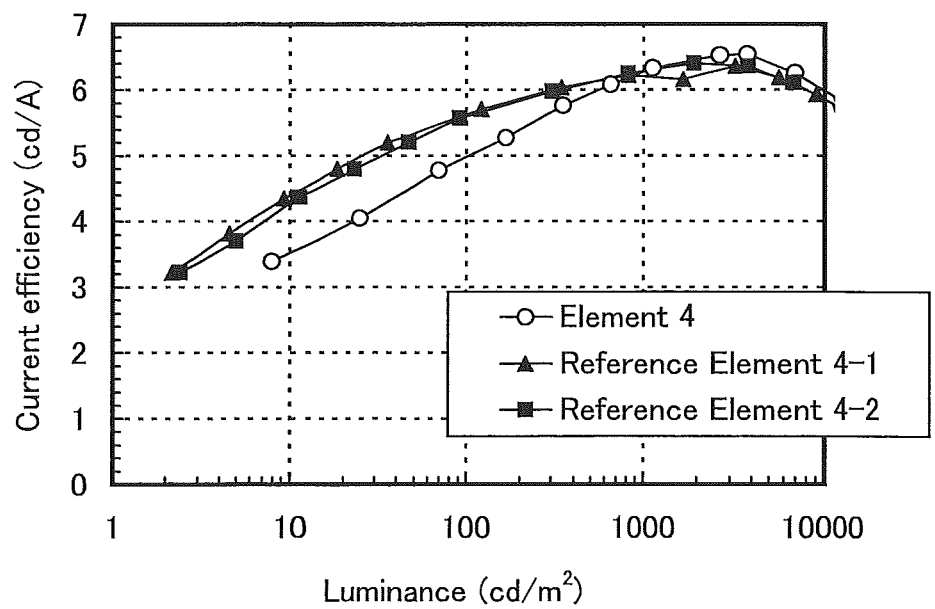
FIG. 26 shows luminance versus current efficiency characteristics of the light-emitting element 4 and the comparison light-emitting elements 4-1 and 4-2.
Figure 27:
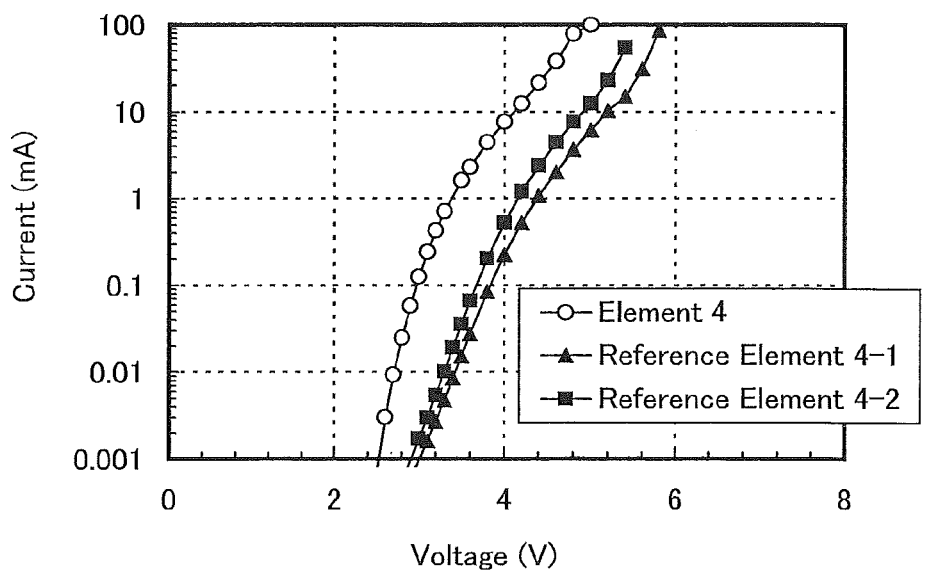
FIG. 27 shows voltage versus current characteristics of the light-emitting element 4 and the comparison light-emitting elements 4-1 and 4-2.
Figure 28:
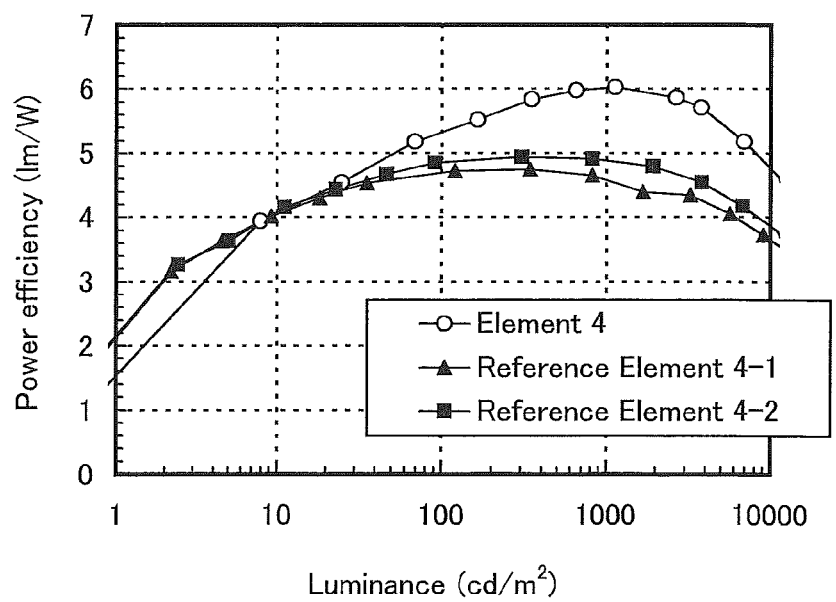
FIG. 28 shows luminance versus power efficiency characteristics of the light-emitting element 4 and the comparison light-emitting elements 4-1 and 4-2.
Figure 29:
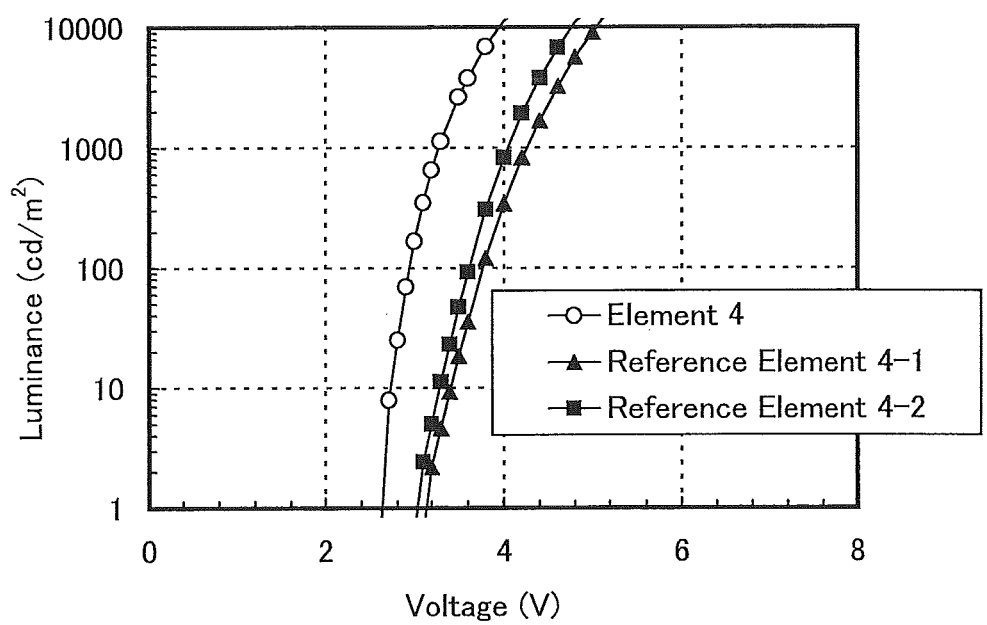
FIG. 29 shows voltage versus luminance characteristics of the light-emitting element 4 and the comparison light-emitting elements 4-1 and 4-2.

FIG. 25 shows current density versus luminance characteristics of the light-emitting element 4 and the comparison light-emitting elements 4-1 and 4-2, FIG. 26 shows luminance versus current efficiency characteristics, FIG. 27 shows voltage versus current characteristics, FIG. 28 shows luminance versus power efficiency characteristics, and FIG. 29 shows voltage versus luminance characteristics. In FIG. 25, the vertical axis represents luminance (cd/m$^2$) and the horizontal axis represents current density (mA/cm$^2$). In FIG. 26, the vertical axis represents current efficiency (cd/A) and the horizontal axis represents luminance (cd/m$^2$). In FIG. 27, the vertical axis represents current (mA) and the horizontal axis represents voltage (V). In FIG. 28, the vertical axis represents power efficiency (lm/W) and the horizontal axis represents luminance (cd/m$^2$). In FIG. 29, the vertical axis represents luminance (cd/m$^2$) and the horizontal axis represents voltage (V).

As can be seen from FIG. 25, the light-emitting element 4 and the comparison light-emitting elements 4-1 and 4-2 have substantially equal current density versus luminance characteristics. In addition, FIG. 26 reveals that the light-emitting element 4 and the comparison light-emitting elements 4-1 and 4-2 have substantially equal luminance versus current efficiency characteristics, at a luminance of at least 1000 cd/m$^2$ or more which is a practical luminance.

Furthermore, FIG. 27 reveals that the light-emitting element 4 exhibits much better voltage versus current characteristics than the comparison light-emitting elements 4-1 and 4-2. This indicates the favorable carrier-transport property of cgDBCzPA. Thus, also as seen from FIG. 28, the light-emitting element 4 is found to be an element having highly favorable luminance versus power efficiency characteristics. Note that FIG. 29 shows high driving voltage of the comparison light-emitting elements 4-1 and 4-2, and in order to achieve a luminance of 1000 cd/m$^2$, which is of practical use, a voltage of about 3.3 V needs to be applied to the light-emitting element 4 but a voltage of 4 V or more needs to be applied to each of the comparison light-emitting elements 4-1 and 4-2. The driving voltage of the comparison light-emitting element 4-1 is especially high.

Figure 30:
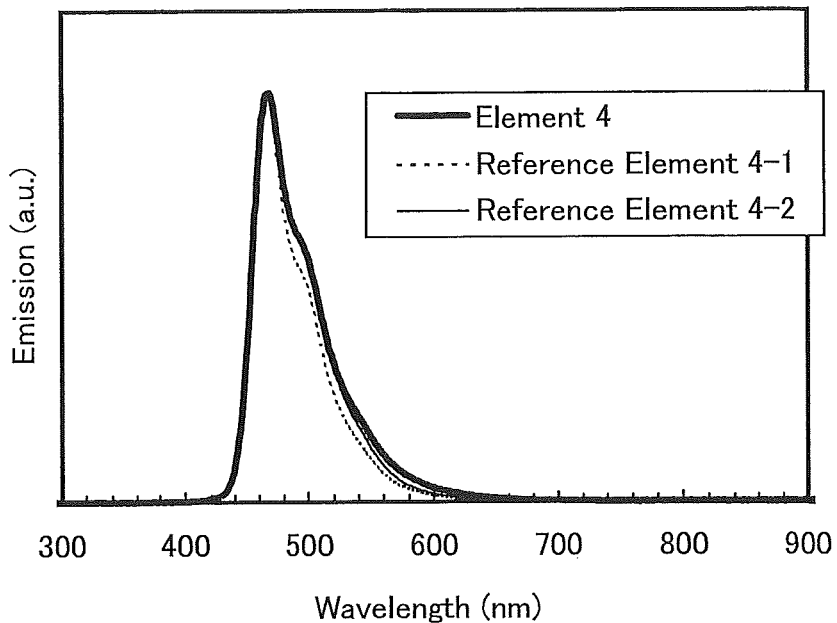
FIG. 30 shows emission spectra of the light-emitting element 4 and the comparison light-emitting elements 4-1 and 4-2.

FIG. 30 shows normalized emission spectra obtained when a current of 0.1 mA was made to flow in the fabricated light-emitting element 4 and the comparison light-emitting elements 4-1 and 4-2. In FIG. 30, the vertical axis represents emission intensity (arbitrary unit) and the horizontal axis represents wavelength (nm). FIG. 30 shows that the spectra of the light-emitting element 4 and the comparison light-emitting elements 4-1 and 4-2 are not greatly different, which indicates that both elements emit blue light derived from 1,6mMemFLPAPrn, which was the emission substance.

Figure 31:
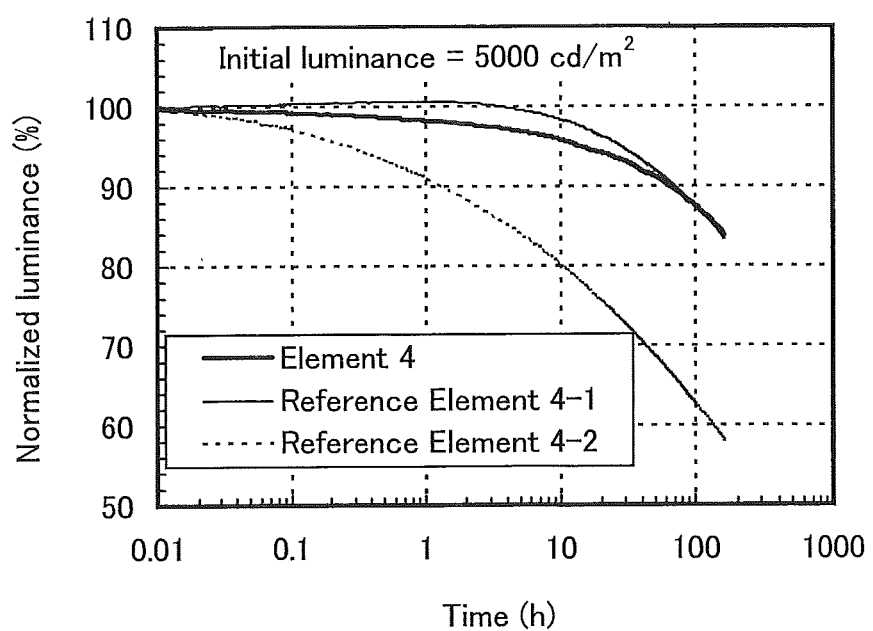
FIG. 31 shows normalized luminance versus time characteristics of the light-emitting element 4 and the comparison light-emitting elements 4-1 and 4-2.

Next, with an initial luminance set to 5000 cd/m$^2$, the light-emitting element 4 and the comparison light-emitting elements 4-1 and 4-2 were driven under a condition where the current density was constant, and changes in luminance relative to driving time were measured. FIG. 31 shows normalized luminance versus time characteristics. FIG. 31 shows that the comparison light-emitting element 4-2 using the substance represented by the above structural formula (viii) has a shorter lifetime than the other elements. In addition, although the comparison light-emitting element 4-1 using the substance represented by the above structural formula (vii) instead of cgDBCzPA has a lifetime equal to that of the light-emitting element 4 at a glance, the comparison light-emitting element 4-1 exhibits not only a rise in luminance at an initial stage but also an increase in deterioration rate after a certain period; consequently, the half life of the comparison light-emitting element 4-1 is estimated at about a half of that of the light-emitting element 4.

Thus, the comparison light-emitting element 4-1 has a drawback in driving voltage and the comparison light-emitting element 4-2 has drawbacks in both driving voltage and lifetime, and it is difficult for each element to have excellent characteristics in various aspects. In contrast, it is found that by using cgDBCzPA, a high-performance light-emitting element which is excellent in various characteristics in terms of efficiency, driving voltage, and lifetime can be fabricated. What is remarkable is the driving voltage, which enables a light-emitting element having very high power efficiency to be provided.

As described above, with use of cgDBCzPA, a light-emitting element excellent in various characteristics can be provided.

This application is based on Japanese Patent Application serial no. 2012-270021 filed with Japan Patent Office on Dec. 11, 2012, the entire contents of which are hereby incorporated by reference.

What is claimed is:

1. A solution comprising:
a compound; and
a solvent;
wherein the compound gives a first peak at a mass-to-charge ratio of 266.10 in a mass spectrum.

2. The solution according to claim 1, wherein the mass spectrum is obtained by liquid chromatography/mass spectrometry.

3. The solution according to claim 1, wherein the solvent is toluene.

4. The solution according to claim 1, wherein the solution further gives a second peak at a mass-to-charge ratio of 330.14 in the mass spectrum.

5. The solution according to claim 1, wherein the solution further gives a third peak at a mass-to-charge ratio of 252.09 in the mass spectrum.

6. The solution according to claim 1, an intensity of the first peak is largest in the mass spectrum.

7. The solution according to claim 1,
wherein the compound is represented by a formula (G1):

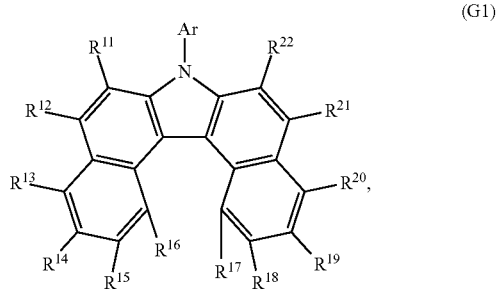

(G1)

and
wherein:
Ar represents a substituted or unsubstituted aryl group having 14 to 30 carbon atoms and including a substituted or unsubstituted anthracene skeleton;
$R^{11}$ to $R^{22}$ each independently represent any of hydrogen, an alkyl group having 1 to 4 carbon atoms, and an aryl group having 6 to 12 carbon atoms; and
wherein the substituent of the anthracene skeleton is an alkyl group having 1 to 4 carbon atoms or an aryl group having 6 to 10 carbon atoms.

8. The solution according to claim 7, wherein the compound is represented by a formula (G2):

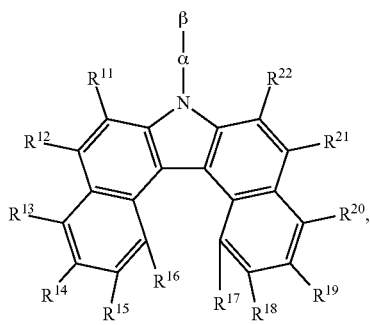

(G2)

and
wherein:
α represents a substituted or unsubstituted arylene group;
β represents a substituted or unsubstituted anthryl group;
$R^{11}$ to $R^{22}$ each independently represent any of hydrogen, an alkyl group having 1 to 4 carbon atoms, and an aryl group having 6 to 12 carbon atoms; and
wherein the substituent of the anthracene skeleton is an alkyl group having 1 to 4 carbon atoms or an aryl group having 6 to 10 carbon atoms.

9. The solution according to claim 8, wherein the arylene group is a phenylene group or a naphthylene group.

10. The solution according to claim 1, wherein the compound is represented by a formula (G3):

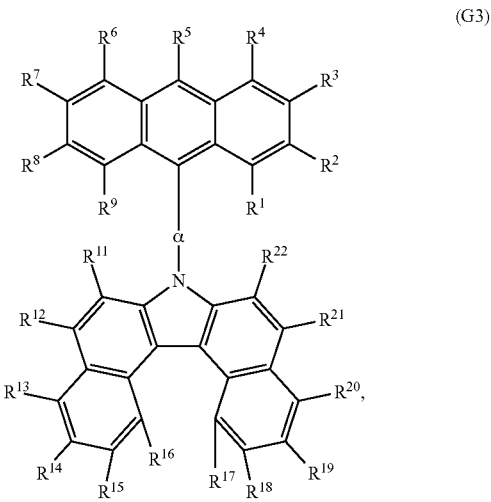

(G3)

and
wherein:
$R^1$ to $R^4$ and $R^6$ to $R^9$ each independently represent any of hydrogen or an alkyl group having 1 to 4 carbon atoms;
$R^5$ represents any of hydrogen, an alkyl group having 1 to 4 carbon atoms, and an aryl group having 6 to 10 carbon atoms; and
$R^{11}$ to $R^{22}$ each independently represent any of hydrogen, an alkyl group having 1 to 4 carbon atoms, and an aryl group having 6 to 12 carbon atoms.

11. A light-emitting element comprising the solution according to claim 1.

12. A light-emitting device comprising the light-emitting element according to claim 11.

13. A lighting device comprising the light-emitting device according to claim 12.

14. An electronic device comprising the light-emitting device according to claim 12.

* * * * *